US012582763B2

(12) United States Patent (10) Patent No.: US 12,582,763 B2
Elder et al. (45) Date of Patent: Mar. 24, 2026

(54) COMMUNICATION SYSTEMS AND METHODS FOR NEGATIVE PRESSURE WOUND THERAPY DEVICES

(71) Applicant: T.J.Smith and Nephew, Limited, Hull (GB)

(72) Inventors: David Michael Elder, Hull (GB); Felix Clarence Quintanar, Hull (GB)

(73) Assignee: T.J.Smith and Nephew, Limited, Hull (GB)

( * ) Notice: Subject to any disclaimer, the term of this patent is extended or adjusted under 35 U.S.C. 154(b) by 145 days.

(21) Appl. No.: 18/287,856

(22) PCT Filed: Apr. 20, 2022

(86) PCT No.: PCT/EP2022/060464
§ 371 (c)(1),
(2) Date: Oct. 20, 2023

(87) PCT Pub. No.: WO2022/223646
PCT Pub. Date: Oct. 27, 2022

(65) Prior Publication Data
US 2024/0189501 A1      Jun. 13, 2024

Related U.S. Application Data

(60) Provisional application No. 63/177,800, filed on Apr. 21, 2021.

(51) Int. Cl.
A61M 1/00 (2006.01)
(52) U.S. Cl.
CPC ......... A61M 1/982 (2021.05); A61M 2205/14 (2013.01); A61M 2205/3569 (2013.01);
(Continued)

(58) Field of Classification Search
CPC ........... A61M 1/98; A61M 2205/3331; A61M 1/982; A61M 2205/18; A61M 2205/3317;
(Continued)

(56) References Cited

U.S. PATENT DOCUMENTS 695,270 A      3/1902  Beringer
3,194,239 A    7/1965  Sullivan et al.
(Continued)

FOREIGN PATENT DOCUMENTS

CN      102961815 A     3/2013
CN      104721892 A     6/2015
(Continued)

OTHER PUBLICATIONS

Cinterion., "Cinterion PHS8-P 3G HSPA+," retrieved from http://www.cinterion.com/tl_files/cinterion/downloads/cinterion_datasheet_PHSS_web.pdf, 2012, 2 pages.
(Continued)

*Primary Examiner* — Guy K Townsend
*Assistant Examiner* — Alessandro R Del Priore
(74) *Attorney, Agent, or Firm* — Knobbe, Martens, Olson & Bear, LLP

(57) ABSTRACT

A negative pressure wound therapy device can include one or more antennas and communication circuitry. Various communication protocols can be supported, including short, medium, and long range communication protocols. Depending on the environment and application, various data related to the status of the negative pressure wound therapy device or any of the accessories can be transmitted using the one or more communication protocols.

13 Claims, 19 Drawing Sheets

(52) U.S. Cl.
CPC ............... *A61M 2205/3584* (2013.01); *A61M 2205/6027* (2013.01)

(58) Field of Classification Search
CPC .. A61M 2205/3382; A61M 2205/3569; A61M 1/90; A61M 1/60; A61M 27/00; A61M 2205/14; A61M 2205/3584; A61M 2205/6027; A61M 2205/3553; A61M 2205/3561; A61M 2205/3576; A61M 1/966; H04L 63/166; H04L 63/18; H04W 4/02; H04W 12/63; H04W 12/50
See application file for complete search history.

(56) References Cited

U.S. PATENT DOCUMENTS

| | | | |
|---|---|---|---|
| 4,832,299 A | 5/1989 | Gorton et al. | |
| 5,219,428 A | 6/1993 | Stern | |
| 5,473,536 A | 12/1995 | Wimmer | |
| 5,960,403 A | 9/1999 | Brown | |
| 6,055,506 A | 4/2000 | Frasca et al. | |
| 6,336,900 B1 | 1/2002 | Alleckson et al. | |
| 6,353,445 B1 | 3/2002 | Babula et al. | |
| 6,375,614 B1 | 4/2002 | Braun et al. | |
| 6,385,622 B2 | 5/2002 | Bouve et al. | |
| 6,406,426 B1 | 6/2002 | Reuss et al. | |
| 6,434,572 B2 | 8/2002 | Derzay et al. | |
| 6,460,041 B2 | 10/2002 | Lloyd | |
| 6,505,054 B1 * | 1/2003 | Douglas | H01Q 1/405 |
| | | | 455/552.1 |
| 6,529,139 B1 * | 3/2003 | Behun | A63H 30/04 |
| | | | 340/12.5 |
| 6,574,518 B1 | 6/2003 | Lounsberry et al. | |
| 6,640,145 B2 | 10/2003 | Hoffberg et al. | |
| 6,640,246 B1 | 10/2003 | Gary et al. | |
| 6,675,131 B2 | 1/2004 | Hahn | |
| 6,681,003 B2 | 1/2004 | Linder et al. | |
| 6,723,046 B2 | 4/2004 | Lichtenstein et al. | |
| 6,730,024 B2 | 5/2004 | Freyre et al. | |
| 6,747,556 B2 | 6/2004 | Medema et al. | |
| 6,779,024 B2 | 8/2004 | DeLaHuerga | |
| 6,782,285 B2 | 8/2004 | Birkenbach et al. | |
| 6,856,825 B2 | 2/2005 | Hahn | |
| 6,868,528 B2 | 3/2005 | Roberts | |
| 6,871,211 B2 | 3/2005 | Labounty et al. | |
| 6,909,974 B2 | 6/2005 | Yung et al. | |
| 6,912,481 B2 | 6/2005 | Breunissen et al. | |
| 6,961,731 B2 | 11/2005 | Holbrook | |
| 7,004,915 B2 | 2/2006 | Boynton et al. | |
| 7,022,113 B2 | 4/2006 | Lockwood et al. | |
| 7,051,012 B2 | 5/2006 | Cole et al. | |
| 7,062,251 B2 | 6/2006 | Birkett et al. | |
| 7,066,883 B2 | 6/2006 | Schmidt et al. | |
| 7,103,578 B2 | 9/2006 | Beck et al. | |
| 7,108,683 B2 | 9/2006 | Zamierowski | |
| 7,120,488 B2 | 10/2006 | Nova et al. | |
| 7,133,869 B2 | 11/2006 | Bryan et al. | |
| 7,167,858 B2 | 1/2007 | Naeymi-Rad et al. | |
| 7,212,829 B1 | 5/2007 | Lau et al. | |
| 7,264,591 B2 | 9/2007 | Brown | |
| 7,300,418 B2 | 11/2007 | Zaleski | |
| 7,304,573 B2 | 12/2007 | Postma | |
| 7,311,665 B2 | 12/2007 | Hawthorne et al. | |
| 7,333,002 B2 | 2/2008 | Bixler et al. | |
| 7,353,179 B2 | 4/2008 | Ott et al. | |
| 7,384,267 B1 | 6/2008 | Franks et al. | |
| 7,430,598 B2 | 9/2008 | Raden et al. | |
| 7,430,608 B2 | 9/2008 | Noonan et al. | |
| 7,451,002 B2 | 11/2008 | Choubey | |
| 7,457,804 B2 | 11/2008 | Uber et al. | |
| 7,460,872 B2 | 12/2008 | Millard et al. | |
| 7,534,240 B1 | 5/2009 | Johnson | |
| 7,598,855 B2 | 10/2009 | Scalisi et al. | |
| 7,608,066 B2 | 10/2009 | Vogel | |
| 7,627,334 B2 | 12/2009 | Cohen et al. | |
| 7,649,449 B2 | 1/2010 | Fenske et al. | |
| 7,671,733 B2 | 3/2010 | McNeal et al. | |
| 7,684,999 B2 | 3/2010 | Brown | |
| 7,698,156 B2 | 4/2010 | Martucci et al. | |
| 7,734,764 B2 | 6/2010 | Weiner et al. | |
| 7,749,164 B2 | 7/2010 | Davis | |
| 7,758,555 B2 | 7/2010 | Kelch et al. | |
| 7,779,153 B2 | 8/2010 | Van Den Heuvel et al. | |
| 7,789,828 B2 | 9/2010 | Clapp | |
| 7,794,438 B2 | 9/2010 | Henley et al. | |
| 7,827,148 B2 | 11/2010 | Mori et al. | |
| 7,865,375 B2 | 1/2011 | Lancaster et al. | |
| 7,889,069 B2 | 2/2011 | Fifolt et al. | |
| 7,890,887 B1 | 2/2011 | Linardos et al. | |
| 7,912,823 B2 | 3/2011 | Ferrari et al. | |
| 7,925,603 B1 | 4/2011 | Laidig et al. | |
| 7,933,817 B2 | 4/2011 | Radl et al. | |
| 7,976,519 B2 | 7/2011 | Bubb et al. | |
| 7,981,098 B2 | 7/2011 | Boehringer et al. | |
| 7,988,850 B2 | 8/2011 | Roncadi et al. | |
| 8,015,443 B2 | 9/2011 | Adachi | |
| 8,015,972 B2 | 9/2011 | Pirzada | |
| 8,019,618 B2 | 9/2011 | Brown | |
| 8,036,925 B2 | 10/2011 | Choubey | |
| 8,054,950 B1 | 11/2011 | Hung et al. | |
| 8,069,057 B2 | 11/2011 | Choubey et al. | |
| 8,094,009 B2 | 1/2012 | Allen et al. | |
| 8,126,735 B2 | 2/2012 | Dicks et al. | |
| 8,130,095 B2 | 3/2012 | Allen et al. | |
| 8,131,472 B2 | 3/2012 | Chow et al. | |
| 8,157,792 B2 | 4/2012 | Dolliver et al. | |
| 8,180,750 B2 | 5/2012 | Wilmering et al. | |
| 8,190,445 B2 | 5/2012 | Kuth et al. | |
| 8,190,448 B2 | 5/2012 | Bajars et al. | |
| 8,228,188 B2 | 7/2012 | Key et al. | |
| 8,246,606 B2 | 8/2012 | Stevenson et al. | |
| 8,249,894 B2 | 8/2012 | Brown | |
| 8,255,241 B2 | 8/2012 | Cafer | |
| 8,260,630 B2 | 9/2012 | Brown | |
| 8,280,682 B2 | 10/2012 | Vock et al. | |
| 8,284,046 B2 | 10/2012 | Allen et al. | |
| 8,290,792 B2 | 10/2012 | Sekura | |
| 8,291,337 B2 | 10/2012 | Gannin et al. | |
| 8,332,233 B2 | 12/2012 | Ott et al. | |
| 8,332,236 B2 | 12/2012 | Yurko et al. | |
| 8,334,768 B2 | 12/2012 | Eaton et al. | |
| 8,337,482 B2 | 12/2012 | Wood et al. | |
| 8,360,975 B1 | 1/2013 | Schwieterman et al. | |
| 8,400,295 B1 | 3/2013 | Khaira | |
| 8,422,377 B2 | 4/2013 | Weiner et al. | |
| 8,424,517 B2 | 4/2013 | Sutherland et al. | |
| 8,436,871 B2 | 5/2013 | Alberte | |
| 8,439,882 B2 | 5/2013 | Kelch | |
| 8,457,740 B2 | 6/2013 | Osche | |
| 8,480,641 B2 | 7/2013 | Jacobs | |
| 8,515,776 B2 | 8/2013 | Schoenberg | |
| 8,532,764 B2 | 9/2013 | Duke | |
| 8,540,688 B2 | 9/2013 | Eckstein et al. | |
| 8,545,483 B2 | 10/2013 | Schwabe et al. | |
| 8,554,195 B2 | 10/2013 | Rao | |
| 8,554,902 B2 | 10/2013 | Ebert et al. | |
| 8,558,964 B2 | 10/2013 | Bedingfield | |
| 8,560,082 B2 | 10/2013 | Wei | |
| 8,577,694 B2 | 11/2013 | Kanaan | |
| 8,595,553 B2 | 11/2013 | Goertler et al. | |
| 8,600,777 B2 | 12/2013 | Schoenberg et al. | |
| 8,626,342 B2 | 1/2014 | Williams et al. | |
| 8,626,526 B2 | 1/2014 | Lemke et al. | |
| 8,630,660 B2 | 1/2014 | Ray et al. | |
| 8,632,485 B2 | 1/2014 | Schlaeper et al. | |
| 8,641,693 B2 | 2/2014 | Locke et al. | |
| 8,659,420 B2 | 2/2014 | Salvat et al. | |
| 8,676,597 B2 | 3/2014 | Buehler et al. | |
| 8,689,008 B2 | 4/2014 | Rangadass et al. | |
| 8,694,600 B2 | 4/2014 | Gaines et al. | |
| 8,706,537 B1 | 4/2014 | Young et al. | |
| 8,725,528 B2 | 5/2014 | Locke et al. | |
| 8,756,078 B2 | 6/2014 | Collins, Jr. et al. | |
| 8,757,485 B2 | 6/2014 | Drees et al. | |

(56) References Cited

U.S. PATENT DOCUMENTS

| | | |
|---|---|---|
| 8,758,315 B2 | 6/2014 | Chen et al. |
| 8,768,441 B2 | 7/2014 | De Zwart et al. |
| 8,769,625 B2 | 7/2014 | Wang et al. |
| 8,781,847 B2 | 7/2014 | Simms et al. |
| 8,795,171 B2 | 8/2014 | Adamczyk |
| 8,795,244 B2 | 8/2014 | Randolph et al. |
| 8,838,136 B2 | 9/2014 | Carnes et al. |
| 8,858,517 B2 | 10/2014 | Pan et al. |
| 8,862,393 B2 | 10/2014 | Zhou et al. |
| 8,868,794 B2 | 10/2014 | Masoud et al. |
| 8,874,035 B2 | 10/2014 | Sherman et al. |
| 8,887,100 B1 | 11/2014 | Cook et al. |
| 8,890,656 B2 | 11/2014 | Pendse |
| 8,897,198 B2 | 11/2014 | Gaines et al. |
| 8,902,278 B2 | 12/2014 | Pinter et al. |
| 8,905,959 B2 | 12/2014 | Basaglia |
| 8,909,595 B2 | 12/2014 | Gandy et al. |
| 8,912,897 B2 | 12/2014 | Carnes |
| 8,922,377 B2 | 12/2014 | Carnes |
| 8,945,073 B2 | 2/2015 | Croizat et al. |
| 8,947,237 B2 | 2/2015 | Margon et al. |
| 8,978,026 B2 | 3/2015 | Charlton et al. |
| 8,996,393 B2 | 3/2015 | Sobie |
| 9,047,648 B1 | 6/2015 | Lekutai et al. |
| 9,058,634 B2 | 6/2015 | Buan et al. |
| 9,081,885 B2 | 7/2015 | Bangera et al. |
| 9,087,141 B2 | 7/2015 | Huang et al. |
| 9,092,705 B2 | 7/2015 | Zhuang |
| 9,098,114 B2 | 8/2015 | Potter et al. |
| 9,105,006 B2 | 8/2015 | Williamson |
| 9,114,054 B2 | 8/2015 | Bennett |
| 9,117,012 B2 | 8/2015 | Basaglia |
| 9,135,398 B2 | 9/2015 | Kaib et al. |
| 9,141,270 B1 | 9/2015 | Stuart et al. |
| 9,159,148 B2 | 10/2015 | Boyer et al. |
| 9,215,516 B2 | 12/2015 | Carnes et al. |
| 9,215,581 B2 | 12/2015 | Julian et al. |
| 9,230,420 B2 | 1/2016 | Lee et al. |
| 9,268,827 B2 | 2/2016 | Fernandez |
| 9,286,443 B2 | 3/2016 | Ford et al. |
| 9,323,893 B2 | 4/2016 | Berry et al. |
| 9,332,363 B2 | 5/2016 | Jain et al. |
| 9,338,819 B2 | 5/2016 | Meng et al. |
| 9,427,159 B2 | 8/2016 | Chang |
| 9,436,645 B2 | 9/2016 | Al-Ali et al. |
| 9,436,800 B2 | 9/2016 | Forrester |
| 9,439,584 B1 | 9/2016 | De Vries et al. |
| 9,460,431 B2 | 10/2016 | Curry |
| 9,474,679 B2 | 10/2016 | Locke et al. |
| 9,483,614 B2 | 11/2016 | Ash et al. |
| 9,539,373 B2 | 1/2017 | Jones et al. |
| 9,558,331 B2 | 1/2017 | Orona et al. |
| 9,585,565 B2 | 3/2017 | Carnes |
| 9,589,247 B2 | 3/2017 | Bolene et al. |
| 9,602,952 B2 | 3/2017 | Kang et al. |
| 9,629,986 B2 | 4/2017 | Patel et al. |
| 9,658,066 B2 | 5/2017 | Yuen et al. |
| 9,662,438 B2 | 5/2017 | Kamen et al. |
| 9,687,618 B2 | 6/2017 | Steinhauer et al. |
| 9,693,691 B2 | 7/2017 | Johnson |
| 9,700,462 B2 | 7/2017 | DeBusk et al. |
| 9,716,757 B2 | 7/2017 | Fernandes |
| 9,740,825 B2 | 8/2017 | Sansale et al. |
| 9,741,084 B2 | 8/2017 | Holmes et al. |
| 9,787,842 B1 | 10/2017 | Brooksby et al. |
| 9,792,660 B2 | 10/2017 | Cannon et al. |
| 9,817,948 B2 | 11/2017 | Swank |
| 9,818,164 B2 | 11/2017 | Nolte et al. |
| 9,838,645 B2 | 12/2017 | Hyde et al. |
| 9,864,066 B2 | 1/2018 | Park et al. |
| 9,871,866 B2 | 1/2018 | Borges et al. |
| 9,878,081 B2 | 1/2018 | Leiendecker et al. |
| 9,905,123 B2 | 2/2018 | Lawhorn |
| 9,928,478 B2 | 3/2018 | Ragusky et al. |
| 9,974,492 B1 | 5/2018 | Dicks et al. |
| 9,990,466 B2 | 6/2018 | DeBusk et al. |
| 9,996,681 B2 | 6/2018 | Suarez et al. |
| 10,049,346 B2 | 8/2018 | Jensen et al. |
| 10,061,894 B2 | 8/2018 | Sethumadhavan et al. |
| 10,095,649 B2 | 10/2018 | Joshua et al. |
| 10,127,357 B2 | 11/2018 | Whiting et al. |
| 10,152,575 B2 | 12/2018 | Sexton et al. |
| 10,173,008 B2 | 1/2019 | Simpson et al. |
| 10,185,834 B2 | 1/2019 | Adam et al. |
| 10,207,031 B2 | 2/2019 | Toth |
| 10,328,188 B2 | 6/2019 | Deutsch et al. |
| 11,376,357 B2 | 7/2022 | Aarestad et al. |
| 11,478,383 B2 | 10/2022 | Severns et al. |
| 11,614,170 B2 | 3/2023 | Tumey et al. |
| 2002/0087360 A1 | 7/2002 | Pettit |
| 2002/0128804 A1 | 9/2002 | Geva |
| 2002/0128869 A1 | 9/2002 | Kuth |
| 2002/0135336 A1 | 9/2002 | Zhou et al. |
| 2002/0177757 A1 | 11/2002 | Britton |
| 2002/0184055 A1 | 12/2002 | Naghavi et al. |
| 2003/0009244 A1 | 1/2003 | Engleson et al. |
| 2003/0014022 A1* | 1/2003 | Lockwood ............ A61M 1/732 |
| | | 604/315 |
| 2003/0018736 A1 | 1/2003 | Christ et al. |
| 2003/0105649 A1 | 6/2003 | Sheiner et al. |
| 2003/0182158 A1 | 9/2003 | Son |
| 2003/0221687 A1 | 12/2003 | Kaigler |
| 2003/0229518 A1 | 12/2003 | Abraham-Fuchs et al. |
| 2004/0006492 A1 | 1/2004 | Watanabe |
| 2004/0054775 A1 | 3/2004 | Poliac et al. |
| 2004/0078223 A1 | 4/2004 | Sacco et al. |
| 2004/0143458 A1 | 7/2004 | Pulkkinen et al. |
| 2004/0167802 A1 | 8/2004 | Takada et al. |
| 2004/0167804 A1 | 8/2004 | Simpson et al. |
| 2004/0172301 A1 | 9/2004 | Mihai et al. |
| 2004/0181433 A1 | 9/2004 | Blair |
| 2004/0193449 A1 | 9/2004 | Wildman et al. |
| 2004/0204962 A1 | 10/2004 | Howser et al. |
| 2005/0033124 A1 | 2/2005 | Kelly et al. |
| 2005/0055225 A1 | 3/2005 | Mehl |
| 2005/0055242 A1 | 3/2005 | Bello et al. |
| 2005/0055244 A1 | 3/2005 | Mullan et al. |
| 2005/0060211 A1 | 3/2005 | Xiao et al. |
| 2005/0065817 A1 | 3/2005 | Mihai et al. |
| 2005/0097200 A1 | 5/2005 | Denning et al. |
| 2005/0102167 A1 | 5/2005 | Kapoor |
| 2005/0108046 A1 | 5/2005 | Craft |
| 2005/0108057 A1 | 5/2005 | Cohen et al. |
| 2005/0114176 A1 | 5/2005 | Dominick et al. |
| 2005/0119914 A1 | 6/2005 | Batch |
| 2005/0222873 A1 | 10/2005 | Nephin et al. |
| 2005/0240111 A1 | 10/2005 | Chung |
| 2005/0283382 A1 | 12/2005 | Donoghue et al. |
| 2006/0004604 A1 | 1/2006 | White |
| 2006/0064323 A1 | 3/2006 | Alleckson et al. |
| 2006/0085393 A1 | 4/2006 | Modesitt |
| 2006/0089539 A1 | 4/2006 | Miodownik et al. |
| 2006/0095853 A1 | 5/2006 | Amyot et al. |
| 2006/0155584 A1 | 7/2006 | Aggarwal |
| 2006/0161460 A1 | 7/2006 | Smitherman et al. |
| 2006/0190130 A1 | 8/2006 | Fedor et al. |
| 2006/0195843 A1 | 8/2006 | Hall |
| 2006/0246922 A1 | 11/2006 | Gasbarro et al. |
| 2007/0136099 A1 | 6/2007 | Neligh et al. |
| 2007/0156456 A1 | 7/2007 | McGillin et al. |
| 2007/0197881 A1 | 8/2007 | Wolf et al. |
| 2007/0219826 A1 | 9/2007 | Brodsky et al. |
| 2007/0255116 A1 | 11/2007 | Mehta et al. |
| 2007/0271298 A1 | 11/2007 | Juang et al. |
| 2008/0009681 A1 | 1/2008 | Al Hussiny |
| 2008/0086357 A1 | 4/2008 | Choubey et al. |
| 2008/0091659 A1 | 4/2008 | McFaul |
| 2008/0119705 A1 | 5/2008 | Patel et al. |
| 2008/0126126 A1 | 5/2008 | Ballai |
| 2008/0140160 A1 | 6/2008 | Goetz et al. |
| 2008/0167534 A1 | 7/2008 | Young et al. |
| 2008/0177579 A1 | 7/2008 | DeHaan |
| 2008/0221396 A1 | 9/2008 | Garces et al. |
| 2008/0242945 A1 | 10/2008 | Gugliotti et al. |

(56) References Cited

U.S. PATENT DOCUMENTS

| | | |
|---|---|---|
| 2008/0312953 A1 | 12/2008 | Claus |
| 2009/0037220 A1 | 2/2009 | Chambers et al. |
| 2009/0048492 A1 | 2/2009 | Rantala et al. |
| 2009/0048865 A1 | 2/2009 | Breazeale, Jr. |
| 2009/0097623 A1 | 4/2009 | Bharadwaj |
| 2009/0099867 A1 | 4/2009 | Newman |
| 2009/0115663 A1 | 5/2009 | Brown et al. |
| 2009/0118591 A1 | 5/2009 | Kim et al. |
| 2009/0125331 A1 | 5/2009 | Pamsgaard et al. |
| 2009/0136909 A1 | 5/2009 | Asukai et al. |
| 2009/0144091 A1 | 6/2009 | Rago |
| 2009/0157429 A1 | 6/2009 | Lee et al. |
| 2009/0163774 A1 | 6/2009 | Thatha et al. |
| 2009/0171166 A1 | 7/2009 | Amundson et al. |
| 2009/0177495 A1 | 7/2009 | Abousy et al. |
| 2009/0187424 A1 | 7/2009 | Grabowski |
| 2009/0204434 A1 | 8/2009 | Breazeale, Jr. |
| 2009/0204435 A1 | 8/2009 | Gale |
| 2009/0205042 A1 | 8/2009 | Zhou et al. |
| 2009/0224889 A1 | 9/2009 | Aggarwal et al. |
| 2009/0240218 A1* | 9/2009 | Braga .................. A61M 1/984 |
| | | 604/313 |
| 2009/0270833 A1 | 10/2009 | DeBelser et al. |
| 2009/0281822 A1 | 11/2009 | Warner et al. |
| 2009/0281830 A1 | 11/2009 | McNames et al. |
| 2009/0281867 A1 | 11/2009 | Sievenpiper et al. |
| 2009/0326339 A1 | 12/2009 | Horvitz |
| 2009/0327102 A1 | 12/2009 | Maniar et al. |
| 2010/0001838 A1 | 1/2010 | Miodownik et al. |
| 2010/0017471 A1 | 1/2010 | Brown et al. |
| 2010/0022848 A1 | 1/2010 | Lee et al. |
| 2010/0022990 A1 | 1/2010 | Karpowicz et al. |
| 2010/0030302 A1 | 2/2010 | Blowers et al. |
| 2010/0036333 A1 | 2/2010 | Schenk, III et al. |
| 2010/0090004 A1 | 4/2010 | Sands et al. |
| 2010/0106528 A1 | 4/2010 | Brackett et al. |
| 2010/0113908 A1 | 5/2010 | Vargas et al. |
| 2010/0145161 A1 | 6/2010 | Niyato et al. |
| 2010/0222645 A1 | 9/2010 | Nadler et al. |
| 2010/0234708 A1 | 9/2010 | Buck et al. |
| 2010/0255876 A1 | 10/2010 | Jordan et al. |
| 2011/0004188 A1 | 1/2011 | Shekalim |
| 2011/0066110 A1 | 3/2011 | Fathallah et al. |
| 2011/0071844 A1 | 3/2011 | Cannon et al. |
| 2011/0073107 A1 | 3/2011 | Rodman et al. |
| 2011/0077605 A1 | 3/2011 | Karpowicz et al. |
| 2011/0106561 A1 | 5/2011 | Eaton, Jr. et al. |
| 2011/0137759 A1 | 6/2011 | Wellington et al. |
| 2011/0145018 A1 | 6/2011 | Fotsch et al. |
| 2011/0173028 A1 | 7/2011 | Bond |
| 2011/0184754 A1 | 7/2011 | Park et al. |
| 2011/0225008 A1 | 9/2011 | Elkouh et al. |
| 2011/0246219 A1 | 10/2011 | Smith et al. |
| 2011/0275353 A1 | 11/2011 | Liu |
| 2011/0288878 A1 | 11/2011 | Blair |
| 2012/0029312 A1 | 2/2012 | Beaudry et al. |
| 2012/0029313 A1 | 2/2012 | Burdett et al. |
| 2012/0032819 A1 | 2/2012 | Chae et al. |
| 2012/0035427 A1 | 2/2012 | Friedman et al. |
| 2012/0077605 A1 | 3/2012 | Nakagaito et al. |
| 2012/0081225 A1 | 4/2012 | Waugh et al. |
| 2012/0089369 A1 | 4/2012 | Abuzeni et al. |
| 2012/0123323 A1 | 5/2012 | Kagan et al. |
| 2012/0123796 A1 | 5/2012 | McFaul |
| 2012/0157889 A1 | 6/2012 | Tanis et al. |
| 2012/0181405 A1 | 7/2012 | Zlatic et al. |
| 2012/0182143 A1 | 7/2012 | Gaines et al. |
| 2012/0191475 A1 | 7/2012 | Pandey |
| 2012/0212455 A1 | 8/2012 | Kloeffel |
| 2012/0215455 A1 | 8/2012 | Patil et al. |
| 2012/0259651 A1 | 10/2012 | Mallon et al. |
| 2012/0264450 A1* | 10/2012 | Kangas .................. H04W 4/02 |
| | | 455/456.1 |
| 2012/0271256 A1 | 10/2012 | Locke et al. |
| 2012/0290217 A1 | 11/2012 | Shoval et al. |
| 2012/0295566 A1 | 11/2012 | Collins et al. |
| 2012/0310205 A1 | 12/2012 | Lee et al. |
| 2013/0018355 A1 | 1/2013 | Brand et al. |
| 2013/0035615 A1 | 2/2013 | Hsieh |
| 2013/0045764 A1 | 2/2013 | Vik et al. |
| 2013/0073303 A1 | 3/2013 | Hsu |
| 2013/0076528 A1 | 3/2013 | Boettner et al. |
| 2013/0087609 A1 | 4/2013 | Nichol et al. |
| 2013/0090949 A1 | 4/2013 | Tibebu |
| 2013/0103419 A1 | 4/2013 | Beaudry |
| 2013/0124227 A1 | 5/2013 | Ellis |
| 2013/0132855 A1 | 5/2013 | Manicka et al. |
| 2013/0150686 A1 | 6/2013 | Fronterhouse et al. |
| 2013/0150698 A1 | 6/2013 | Hsu et al. |
| 2013/0151274 A1 | 6/2013 | Bage et al. |
| 2013/0157571 A1 | 6/2013 | Wondka et al. |
| 2013/0159456 A1 | 6/2013 | Daoud et al. |
| 2013/0160082 A1 | 6/2013 | Miller |
| 2013/0186405 A1 | 7/2013 | Krzyzanowski et al. |
| 2013/0190903 A1 | 7/2013 | Balakrishnan et al. |
| 2013/0191513 A1 | 7/2013 | Kamen et al. |
| 2013/0196703 A1 | 8/2013 | Masoud et al. |
| 2013/0204106 A1 | 8/2013 | Bennett |
| 2013/0211854 A1 | 8/2013 | Wagstaff |
| 2013/0212168 A1 | 8/2013 | Bonasera et al. |
| 2013/0214925 A1 | 8/2013 | Weiss |
| 2013/0218053 A1 | 8/2013 | Kaiser et al. |
| 2013/0226607 A1 | 8/2013 | Woody et al. |
| 2013/0227128 A1 | 8/2013 | Wagstaff |
| 2013/0231596 A1 | 9/2013 | Hornbach et al. |
| 2013/0245387 A1 | 9/2013 | Patel |
| 2013/0253952 A1 | 9/2013 | Burke et al. |
| 2013/0255681 A1 | 10/2013 | Batch et al. |
| 2013/0267919 A1 | 10/2013 | Caso et al. |
| 2013/0268283 A1 | 10/2013 | Vann et al. |
| 2013/0271556 A1 | 10/2013 | Ross et al. |
| 2013/0282395 A1 | 10/2013 | Rustgi et al. |
| 2013/0285837 A1 | 10/2013 | Uchida |
| 2013/0297350 A1 | 11/2013 | Gross et al. |
| 2013/0304489 A1 | 11/2013 | Miller |
| 2013/0310630 A1 | 11/2013 | Smith et al. |
| 2013/0310726 A1 | 11/2013 | Miller et al. |
| 2013/0317753 A1 | 11/2013 | Kamen et al. |
| 2013/0325508 A1 | 12/2013 | Johnson et al. |
| 2013/0331748 A1 | 12/2013 | Wright et al. |
| 2013/0332197 A1 | 12/2013 | Hinkel |
| 2013/0335233 A1 | 12/2013 | Kamar et al. |
| 2013/0339049 A1 | 12/2013 | Blumberg, Jr. et al. |
| 2013/0345524 A1 | 12/2013 | Meyer et al. |
| 2014/0002234 A1 | 1/2014 | Alwan |
| 2014/0028464 A1 | 1/2014 | Garibaldi |
| 2014/0031884 A1 | 1/2014 | Elghazzawi |
| 2014/0032231 A1 | 1/2014 | Semen et al. |
| 2014/0058714 A1 | 2/2014 | Boyer |
| 2014/0087762 A1 | 3/2014 | Galvin et al. |
| 2014/0108033 A1 | 4/2014 | Akbay et al. |
| 2014/0108034 A1 | 4/2014 | Akbay et al. |
| 2014/0108035 A1 | 4/2014 | Akbay et al. |
| 2014/0129250 A1 | 5/2014 | Daniel et al. |
| 2014/0148138 A1 | 5/2014 | Chou |
| 2014/0171753 A1 | 6/2014 | Montejo et al. |
| 2014/0187888 A1 | 7/2014 | Hatziantoniou |
| 2014/0207090 A1 | 7/2014 | Jian |
| 2014/0221788 A1 | 8/2014 | Teller et al. |
| 2014/0222446 A1 | 8/2014 | Ash et al. |
| 2014/0235975 A1 | 8/2014 | Carnes |
| 2014/0244285 A1 | 8/2014 | Hinkle et al. |
| 2014/0244301 A1 | 8/2014 | Lee et al. |
| 2014/0244307 A1 | 8/2014 | Shutko et al. |
| 2014/0266713 A1 | 9/2014 | Sehgal et al. |
| 2014/0275876 A1 | 9/2014 | Hansen et al. |
| 2014/0278502 A1 | 9/2014 | Laskin |
| 2014/0280882 A1 | 9/2014 | Lacerte et al. |
| 2014/0297299 A1 | 10/2014 | Lester, IV |
| 2014/0316819 A1 | 10/2014 | Dunsirn et al. |
| 2014/0350966 A1 | 11/2014 | Khatana et al. |
| 2014/0366878 A1 | 12/2014 | Baron |
| 2014/0372147 A1 | 12/2014 | White |
| 2014/0372522 A1 | 12/2014 | Orona et al. |

(56) References Cited

U.S. PATENT DOCUMENTS

| | | |
|---|---|---|
| 2014/0375470 A1 | 12/2014 | Malveaux |
| 2014/0378895 A1 | 12/2014 | Barack |
| 2015/0012290 A1 | 1/2015 | Inciardi et al. |
| 2015/0019237 A1 | 1/2015 | Doyle et al. |
| 2015/0019257 A1 | 1/2015 | Doyle et al. |
| 2015/0025486 A1 | 1/2015 | Hu et al. |
| 2015/0046137 A1 | 2/2015 | Zeilinger |
| 2015/0066531 A1 | 3/2015 | Jacobson et al. |
| 2015/0072613 A1 | 3/2015 | Swanson |
| 2015/0094830 A1 | 4/2015 | Lipoma et al. |
| 2015/0095059 A1 | 4/2015 | Yegge et al. |
| 2015/0100340 A1 | 4/2015 | Folsom et al. |
| 2015/0112707 A1 | 4/2015 | Manice et al. |
| 2015/0118662 A1 | 4/2015 | Ellison et al. |
| 2015/0119652 A1 | 4/2015 | Hyde et al. |
| 2015/0120318 A1 | 4/2015 | Toyama |
| 2015/0143300 A1 | 5/2015 | Zhang et al. |
| 2015/0164323 A1 | 6/2015 | Holtzclaw |
| 2015/0164376 A1 | 6/2015 | Huang |
| 2015/0186615 A1 | 7/2015 | Armor et al. |
| 2015/0189001 A1 | 7/2015 | Lee et al. |
| 2015/0228043 A1 | 8/2015 | Ryan et al. |
| 2015/0234557 A1 | 8/2015 | Dorn |
| 2015/0234995 A1 | 8/2015 | Casady et al. |
| 2015/0242578 A1 | 8/2015 | Siemon |
| 2015/0242583 A1 | 8/2015 | Edson |
| 2015/0254403 A1 | 9/2015 | Laperna |
| 2015/0257643 A1 | 9/2015 | Watson et al. |
| 2015/0261920 A1 | 9/2015 | Blick |
| 2015/0269323 A1 | 9/2015 | Ginsburg |
| 2015/0286970 A1 | 10/2015 | Dickerson et al. |
| 2015/0304478 A1 | 10/2015 | Kim et al. |
| 2015/0310182 A1 | 10/2015 | Henze et al. |
| 2015/0324943 A1 | 11/2015 | Han et al. |
| 2015/0339445 A1 | 11/2015 | Gruby et al. |
| 2015/0363058 A1 | 12/2015 | Chung et al. |
| 2015/0370984 A1 | 12/2015 | Russell et al. |
| 2015/0370997 A1 | 12/2015 | Krongrad et al. |
| 2015/0379441 A1 | 12/2015 | Syed et al. |
| 2016/0004824 A1 | 1/2016 | Stanton et al. |
| 2016/0018963 A1 | 1/2016 | Robbins et al. |
| 2016/0042154 A1 | 2/2016 | Goldberg et al. |
| 2016/0044141 A1 | 2/2016 | Pfutzenreuter et al. |
| 2016/0055310 A1 | 2/2016 | Bentley et al. |
| 2016/0058286 A1 | 3/2016 | Joshua et al. |
| 2016/0063210 A1 | 3/2016 | Bardi et al. |
| 2016/0066864 A1 | 3/2016 | Frieder et al. |
| 2016/0080365 A1 | 3/2016 | Baker et al. |
| 2016/0085415 A1 | 3/2016 | Humphrys et al. |
| 2016/0098524 A1 | 4/2016 | Himmelstein |
| 2016/0110507 A1 | 4/2016 | Abbo |
| 2016/0128571 A1 | 5/2016 | Adler |
| 2016/0129186 A1 | 5/2016 | Douglas et al. |
| 2016/0135752 A1 | 5/2016 | Beaumont |
| 2016/0142443 A1 | 5/2016 | Ting et al. |
| 2016/0151015 A1 | 6/2016 | Condurso et al. |
| 2016/0154936 A1 | 6/2016 | Kalathil |
| 2016/0154943 A1 | 6/2016 | Cho et al. |
| 2016/0171866 A1 | 6/2016 | Dupasquier et al. |
| 2016/0180031 A1 | 6/2016 | Slater |
| 2016/0184497 A1 | 6/2016 | Phillips et al. |
| 2016/0196399 A1 | 7/2016 | Bonhomme |
| 2016/0203275 A1 | 7/2016 | Benjamin et al. |
| 2016/0203283 A1 | 7/2016 | Baruah et al. |
| 2016/0209837 A1 | 7/2016 | Kim |
| 2016/0212577 A1 | 7/2016 | Dor et al. |
| 2016/0217433 A1 | 7/2016 | Walton et al. |
| 2016/0246943 A1 | 8/2016 | Lake et al. |
| 2016/0260035 A1 | 9/2016 | Crooks et al. |
| 2016/0287189 A1 | 10/2016 | Modai et al. |
| 2016/0308969 A1 | 10/2016 | Aihara et al. |
| 2016/0321404 A1 | 11/2016 | Ginsburg |
| 2016/0321422 A1 | 11/2016 | Albright |
| 2017/0007494 A1 | 1/2017 | Rock et al. |
| 2017/0014028 A1 | 1/2017 | Clear, Jr. |
| 2017/0017765 A1 | 1/2017 | Yegge et al. |
| 2017/0032648 A1 | 2/2017 | McClain et al. |
| 2017/0046503 A1 | 2/2017 | Cho et al. |
| 2017/0053073 A1 | 2/2017 | Allen et al. |
| 2017/0055205 A1 | 2/2017 | Morris et al. |
| 2017/0068781 A1 | 3/2017 | Zasowski et al. |
| 2017/0074717 A1 | 3/2017 | Pilkington et al. |
| 2017/0078396 A1 | 3/2017 | Haas et al. |
| 2017/0116373 A1 | 4/2017 | Ginsburg et al. |
| 2017/0140120 A1 | 5/2017 | Thrower |
| 2017/0150939 A1 | 6/2017 | Shah |
| 2017/0193181 A1 | 7/2017 | Carter et al. |
| 2017/0212995 A1 | 7/2017 | Ingmanson |
| 2017/0220755 A1 | 8/2017 | Fowler et al. |
| 2017/0257682 A1 | 9/2017 | Shtalryd |
| 2017/0270533 A1 | 9/2017 | Barton et al. |
| 2017/0273116 A1 | 9/2017 | Elghazzawi |
| 2017/0327371 A1 | 11/2017 | Bai et al. |
| 2017/0372010 A1 | 12/2017 | Doherty et al. |
| 2018/0004908 A1 | 1/2018 | Barrus et al. |
| 2018/0052454 A1 | 2/2018 | Magno et al. |
| 2018/0121629 A1 | 5/2018 | Dyer et al. |
| 2018/0139572 A1 | 5/2018 | Hansen |
| 2018/0144817 A1 | 5/2018 | Lofgren et al. |
| 2018/0158545 A1 | 6/2018 | Blomquist |
| 2018/0160907 A1 | 6/2018 | Verma |
| 2018/0181714 A1 | 6/2018 | Pillarisetty et al. |
| 2018/0233016 A1 | 8/2018 | Daniel et al. |
| 2018/0233221 A1 | 8/2018 | Blomquist |
| 2018/0279880 A1 | 10/2018 | Bacchi |
| 2018/0286502 A1 | 10/2018 | Lane et al. |
| 2018/0308569 A1 | 10/2018 | Luellen |
| 2018/0308573 A1 | 10/2018 | Hochrein et al. |
| 2018/0315492 A1 | 11/2018 | Bishop et al. |
| 2018/0316388 A1* | 11/2018 | Lee .................... H04W 4/02 |
| 2018/0322944 A1 | 11/2018 | Valdizan |
| 2019/0231946 A1 | 8/2019 | Gregory et al. |
| 2020/0246194 A1 | 8/2020 | Gonzalez et al. |
| 2021/0001019 A1 | 1/2021 | Elder et al. |
| 2021/0030932 A1 | 2/2021 | Brar et al. |
| 2022/0001100 A1 | 1/2022 | Pratt et al. |
| 2022/0072294 A1* | 3/2022 | Locke ................... A61M 39/10 |
| 2022/0116784 A1* | 4/2022 | Da Silva ............... H04W 12/63 |

FOREIGN PATENT DOCUMENTS

| | | |
|---|---|---|
| DE | 102010036405 A1 | 1/2012 |
| EP | 0980227 A1 | 2/2000 |
| EP | 0566381 B1 | 7/2002 |
| EP | 1231965 A2 | 8/2002 |
| EP | 1291802 A2 | 3/2003 |
| EP | 0814864 B1 | 12/2003 |
| EP | 1407624 A2 | 4/2004 |
| EP | 1011420 B1 | 12/2004 |
| EP | 1495713 A1 | 1/2005 |
| EP | 1524619 A2 | 4/2005 |
| EP | 1540557 A2 | 6/2005 |
| EP | 1579367 A2 | 9/2005 |
| EP | 1587017 A2 | 10/2005 |
| EP | 1788503 A2 | 5/2007 |
| EP | 1839244 A1 | 10/2007 |
| EP | 1839615 A1 | 10/2007 |
| EP | 1857950 A2 | 11/2007 |
| EP | 1870068 A1 | 12/2007 |
| EP | 1904964 A1 | 4/2008 |
| EP | 1934852 A1 | 6/2008 |
| EP | 1975828 A2 | 10/2008 |
| EP | 1993435 A2 | 11/2008 |
| EP | 2038786 A2 | 3/2009 |
| EP | 2040604 A2 | 4/2009 |
| EP | 2092470 A2 | 8/2009 |
| EP | 2146297 A1 | 1/2010 |
| EP | 2172859 A1 | 4/2010 |
| EP | 2214552 A1 | 8/2010 |
| EP | 2218478 A1 | 8/2010 |
| EP | 1404213 B1 | 3/2011 |
| EP | 1247229 B1 | 4/2011 |
| EP | 1406540 B1 | 6/2011 |
| EP | 1812094 B1 | 8/2011 |

(56) References Cited

FOREIGN PATENT DOCUMENTS

| EP | 2384472 A1 | 11/2011 |
| EP | 2226002 B1 | 1/2012 |
| EP | 1610494 B1 | 3/2012 |
| EP | 1248660 B1 | 4/2012 |
| EP | 2023800 B1 | 4/2012 |
| EP | 2451513 A1 | 5/2012 |
| EP | 1248661 B1 | 8/2012 |
| EP | 2488977 A1 | 8/2012 |
| EP | 2562665 A2 | 2/2013 |
| EP | 2619723 A2 | 7/2013 |
| EP | 1881784 B1 | 10/2013 |
| EP | 2664194 A2 | 11/2013 |
| EP | 2743850 A2 | 6/2014 |
| EP | 2745204 A1 | 6/2014 |
| EP | 1684146 B1 | 7/2014 |
| EP | 2841895 A1 | 3/2015 |
| EP | 2850771 A1 | 3/2015 |
| EP | 2876567 A1 | 5/2015 |
| EP | 2891999 A2 | 7/2015 |
| EP | 2894581 A1 | 7/2015 |
| EP | 2906101 A2 | 8/2015 |
| EP | 2945084 A1 | 11/2015 |
| EP | 2962266 A1 | 1/2016 |
| EP | 2968829 A1 | 1/2016 |
| EP | 2973089 A1 | 1/2016 |
| EP | 3000082 A1 | 3/2016 |
| EP | 3010398 A1 | 4/2016 |
| EP | 3054389 A2 | 8/2016 |
| EP | 3070628 A1 | 9/2016 |
| EP | 3078010 A1 | 10/2016 |
| EP | 3096113 A1 | 11/2016 |
| EP | 2563437 B1 | 3/2017 |
| EP | 2773393 B1 | 3/2017 |
| EP | 3134854 A1 | 3/2017 |
| EP | 3027242 B1 | 4/2017 |
| EP | 2556650 B1 | 5/2017 |
| EP | 3174569 A1 | 6/2017 |
| EP | 2632407 B1 | 8/2017 |
| EP | 3209358 A1 | 8/2017 |
| EP | 3041571 B1 | 9/2017 |
| EP | 2856767 B1 | 11/2017 |
| EP | 3252635 A1 | 12/2017 |
| EP | 2320971 B1 | 5/2018 |
| EP | 2335173 B1 | 5/2018 |
| EP | 3100188 B1 | 6/2018 |
| EP | 3330973 A1 | 6/2018 |
| EP | 3352174 A1 | 7/2018 |
| EP | 2440112 B1 | 10/2018 |
| EP | 3400549 A1 | 11/2018 |
| EP | 2992500 B1 | 12/2018 |
| EP | 2597584 B1 | 1/2019 |
| EP | 3219340 B1 | 1/2019 |
| EP | 2890456 B1 | 2/2019 |
| EP | 3377130 B1 | 4/2019 |
| EP | 2881875 B1 | 5/2019 |
| EP | 2866851 B1 | 9/2019 |
| GB | 2409951 A | 7/2005 |
| GB | 2436160 A | 9/2007 |
| GB | 2449400 A | 11/2008 |
| GB | 2456708 A | 7/2009 |
| GB | 2423178 B | 5/2010 |
| GB | 2475091 A | 5/2011 |
| GB | 2488904 A | 9/2012 |
| GB | 2446923 B | 5/2013 |
| GB | 2499986 A | 9/2013 |
| GB | 2491946 B | 8/2014 |
| GB | 2499873 B | 5/2016 |
| GB | 2533910 A | 7/2016 |
| GB | 2541286 A | 2/2017 |
| GB | 2550576 B | 6/2018 |
| WO | WO-9627163 A1 | 9/1996 |
| WO | WO-9744745 A1 | 11/1997 |
| WO | WO-9924927 A1 | 5/1999 |
| WO | WO-9963886 A1 | 12/1999 |
| WO | WO-0032088 A1 | 6/2000 |
| WO | WO-0060522 A2 | 10/2000 |
| WO | WO-0133457 A1 | 5/2001 |
| WO | WO-0181829 A1 | 11/2001 |
| WO | WO-0217075 A2 | 2/2002 |
| WO | WO-0233577 A1 | 4/2002 |
| WO | WO-02078594 A2 | 10/2002 |
| WO | WO-02101713 A1 | 12/2002 |
| WO | WO-03054668 A2 | 7/2003 |
| WO | WO-2004057514 A2 | 7/2004 |
| WO | WO-2004074457 A2 | 9/2004 |
| WO | WO-2005022349 A1 | 3/2005 |
| WO | WO-2005031632 A2 | 4/2005 |
| WO | WO-2005036447 A2 | 4/2005 |
| WO | WO-2005045461 A1 | 5/2005 |
| WO | WO-2005053793 A1 | 6/2005 |
| WO | WO-2005057466 A2 | 6/2005 |
| WO | WO-2005083619 A2 | 9/2005 |
| WO | WO-2005101282 A2 | 10/2005 |
| WO | WO-2005109297 A2 | 11/2005 |
| WO | WO-2005120097 A2 | 12/2005 |
| WO | WO-2006021154 A1 | 3/2006 |
| WO | WO-2006066583 A1 | 6/2006 |
| WO | WO-2006066585 A2 | 6/2006 |
| WO | WO-2006071711 A2 | 7/2006 |
| WO | WO-2006099120 A2 | 9/2006 |
| WO | WO-2006108304 A1 | 10/2006 |
| WO | WO-2006108858 A1 | 10/2006 |
| WO | WO-2006111109 A1 | 10/2006 |
| WO | WO-2007027490 A2 | 3/2007 |
| WO | WO-2007035646 A2 | 3/2007 |
| WO | WO-2007127879 A2 | 11/2007 |
| WO | WO-2007133478 A2 | 11/2007 |
| WO | WO-2007137869 A2 | 12/2007 |
| WO | WO-2008010012 A2 | 1/2008 |
| WO | WO-2008036344 A1 | 3/2008 |
| WO | WO-2008062382 A2 | 5/2008 |
| WO | WO-2008116295 A1 | 10/2008 |
| WO | WO-2008150633 A2 | 12/2008 |
| WO | WO-2009140669 A2 | 11/2009 |
| WO | WO-2010017484 A2 | 2/2010 |
| WO | WO-2010025166 A1 | 3/2010 |
| WO | WO-2010025467 A1 | 3/2010 |
| WO | WO-2010078558 A1 | 7/2010 |
| WO | WO-2010085033 A2 | 7/2010 |
| WO | WO-2010132617 A2 | 11/2010 |
| WO | WO-2010145780 A1 | 12/2010 |
| WO | WO-2011005633 A2 | 1/2011 |
| WO | WO-2011023384 A1 | 3/2011 |
| WO | WO-2011039676 A2 | 4/2011 |
| WO | WO-2011046860 A2 | 4/2011 |
| WO | WO-2011047334 A1 | 4/2011 |
| WO | WO-2011137230 A1 | 11/2011 |
| WO | WO-2012127281 A1 | 9/2012 |
| WO | WO-2013026999 A1 | 2/2013 |
| WO | WO-2013036853 A2 | 3/2013 |
| WO | WO-2013061887 A1 | 5/2013 |
| WO | WO-2013102855 A1 | 7/2013 |
| WO | WO-2013109517 A1 | 7/2013 |
| WO | WO-2013138182 A1 | 9/2013 |
| WO | WO-2013141870 A1 | 9/2013 |
| WO | WO-2013155193 A1 | 10/2013 |
| WO | WO-2013175076 A1 | 11/2013 |
| WO | WO-2014015215 A2 | 1/2014 |
| WO | WO-2014018786 A2 | 1/2014 |
| WO | WO-2014075494 A1 | 5/2014 |
| WO | WO-2014089086 A1 | 6/2014 |
| WO | WO-2014100036 A1 | 6/2014 |
| WO | WO-2014106056 A2 | 7/2014 |
| WO | WO-2014123846 A1 | 8/2014 |
| WO | WO-2014133822 A2 | 9/2014 |
| WO | WO-2014141221 A2 | 9/2014 |
| WO | WO-2014145496 A1 | 9/2014 |
| WO | WO-2014150255 A2 | 9/2014 |
| WO | WO-2014152963 A1 | 9/2014 |
| WO | WO-2014189070 A1 | 11/2014 |
| WO | WO-2014009876 A3 | 12/2014 |
| WO | WO-2015019273 A2 | 2/2015 |
| WO | WO-2015025482 A1 | 2/2015 |
| WO | WO-2015026387 A1 | 2/2015 |

(56) References Cited

FOREIGN PATENT DOCUMENTS

| | | | |
|----|----------------|----|---------|
| WO | WO-2015050816 | A1 | 4/2015 |
| WO | WO-2015078112 | A1 | 6/2015 |
| WO | WO-2015085249 | A1 | 6/2015 |
| WO | WO-2015091070 | A1 | 6/2015 |
| WO | WO-2015124670 | A1 | 8/2015 |
| WO | WO-2015132528 | A1 | 9/2015 |
| WO | WO-2015140801 | A2 | 9/2015 |
| WO | WO-2015143099 | A2 | 9/2015 |
| WO | WO-2015145455 | A1 | 10/2015 |
| WO | WO-2015156143 | A1 | 10/2015 |
| WO | WO-2015164787 | A1 | 10/2015 |
| WO | WO-2015179915 | A1 | 12/2015 |
| WO | WO-2015179916 | A1 | 12/2015 |
| WO | WO-2015179917 | A1 | 12/2015 |
| WO | WO-2015181836 | A2 | 12/2015 |
| WO | WO-2015187480 | A1 | 12/2015 |
| WO | WO-2016001088 | A1 | 1/2016 |
| WO | WO-2016006536 | A1 | 1/2016 |
| WO | WO-2016075656 | A1 | 5/2016 |
| WO | WO-2016108163 | A1 | 7/2016 |
| WO | WO-2016118318 | A1 | 7/2016 |
| WO | WO-2016120820 | A2 | 8/2016 |
| WO | WO-2016136694 | A1 | 9/2016 |
| WO | WO-2016141799 | A1 | 9/2016 |
| WO | WO-2016151364 | A1 | 9/2016 |
| WO | WO-2016160849 | A1 | 10/2016 |
| WO | WO-2016175649 | A1 | 11/2016 |
| WO | WO-2016178936 | A1 | 11/2016 |
| WO | WO-2016190978 | A1 | 12/2016 |
| WO | WO-2017001848 | A1 | 1/2017 |
| WO | WO-2017004423 | A1 | 1/2017 |
| WO | WO-2017027729 | A2 | 2/2017 |
| WO | WO-2017035024 | A1 | 3/2017 |

| | | | | | |
|----|----------------|------|---------|---|-----------|
| WO | WO-2017053384 | A1 | 3/2017 | | |
| WO | WO-2017062042 | A1 | 4/2017 | | |
| WO | WO-2017142100 | A1 | 8/2017 | | |
| WO | WO-2017165895 | A1 | 9/2017 | | |
| WO | WO-2017192673 | A1 | 11/2017 | | |
| WO | WO-2018007100 | A1 | 1/2018 | | |
| WO | WO-2018013666 | A1 | 1/2018 | | |
| WO | WO-2018033819 | A1 | 2/2018 | | |
| WO | WO-2018044894 | A1 | 3/2018 | | |
| WO | WO-2018064234 | A1 | 4/2018 | | |
| WO | WO-2018067593 | A2 | 4/2018 | | |
| WO | WO-2018082813 | A1 | 5/2018 | | |
| WO | WO-2018091492 | A1 | 5/2018 | | |
| WO | WO-2018096390 | A1 | 5/2018 | | |
| WO | WO-2018145880 | A1 | 8/2018 | | |
| WO | WO-2018165049 | A1 * | 9/2018 | ............. | H01Q 1/38 |
| WO | WO-2019096828 | A1 | 5/2019 | | |
| WO | WO-2020018328 | A1 | 1/2020 | | |
| WO | WO-2020061334 | A1 | 3/2020 | | |
| WO | WO-2020176331 | A1 | 9/2020 | | |
| WO | WO-2020263508 | A1 | 12/2020 | | |
| WO | WO-2021028494 | A2 | 2/2021 | | |
| WO | WO-2021028773 | A1 | 2/2021 | | |
| WO | WO-2021059209 | A1 | 4/2021 | | |
| WO | WO-2021074052 | A1 | 4/2021 | | |
| WO | WO-2023094915 | A1 | 6/2023 | | |

OTHER PUBLICATIONS

International Preliminary Report on Patentability for Application No. PCT/EP2022/060464, mailed on Nov. 2, 2023, 15 pages.
International Search Report and Written Opinion for Application No. PCT/EP2022/060464, mailed on Oct. 4, 2022, 23 pages.

* cited by examiner

100'

334

110'

108'

106

104

332

102

100

110

132    104

108

130

106

146    140

134

142

170

180

182

186

174

174

174

172

184

188

222

256

222

256

257

222

256          269

222

BLUETOOTH          NFC 268          257

700

710

Mount Brackets
This Side

820

GND
812

Antenna Connection
822

750

1010

1010

750

COMMUNICATION SYSTEMS AND METHODS FOR NEGATIVE PRESSURE WOUND THERAPY DEVICES

CROSS-REFERENCE TO RELATED APPLICATIONS

This application is a U.S. national stage application of International Patent Application No. PCT/EP2022/060464, filed Apr. 20, 2022 and published as WO 2022/223646, which claims priority to U.S. Provisional Application No. 63/177,800, filed Apr. 21, 2021, the entirety of which is hereby incorporated by reference.

TECHNICAL FIELD

Embodiments described herein relate to apparatuses, systems, and methods for the treatment of wounds, for example using dressings in combination with negative pressure wound therapy.

DESCRIPTION OF THE RELATED ART

Many different types of wound dressings are known for aiding in the healing process of a human or animal. These different types of wound dressings include many different types of materials and layers, for example, gauze, pads, foam pads or multi-layer wound dressings. Topical negative pressure (TNP) therapy, sometimes referred to as vacuum assisted closure, negative pressure wound therapy, or reduced pressure wound therapy, is widely recognized as a beneficial mechanism for improving the healing rate of a wound. Such therapy is applicable to a broad range of wounds such as incisional wounds, open wounds, and abdominal wounds or the like. TNP therapy assists in the closure and healing of wounds by reducing tissue edema, encouraging blood flow, stimulating the formation of granulation tissue, removing excess exudates and may reduce bacterial load. Thus, reducing infection to the wound. Furthermore, TNP therapy permits less outside disturbance of the wound and promotes more rapid healing.

SUMMARY

A negative pressure wound therapy device can include a housing. The device can include a negative pressure source supported by the housing. The negative pressure source can be configured to provide negative pressure to a wound covered by a wound dressing. The device can include an electronic control circuitry supported by the housing. The electronic control circuitry can be configured to operate the negative pressure source. The electronic control circuitry can include a first antenna positioned in a top portion of the housing or a side portion of the housing. The first antenna can be configured to facilitate wireless communications using a first communication protocol. The electronic circuitry can include a second antenna positioned in a different location from the first antenna. The second antenna can be configured to facilitate wireless communications using the first communication protocol. The electronic circuitry can include a third antenna configured to facilitate wireless communications using a second communication protocol that is different from the first communication protocol.

The negative pressure wound therapy device of any of the preceding paragraphs and/or any of the devices, systems, or apparatuses disclosed herein can include one or more of the following features. The electronic control circuitry can be configured to transmit, using the first antenna, to a remote computing device pairing information for pairing the remote computing device with the negative pressure wound therapy device to allow exchange of data between the remote computing device and the negative pressure wound therapy device using the second communication protocol. The second communication protocol can permit communication over a longer distance than the first communication protocol. The first communication protocol can include a near-field protocol. The second communication protocol can include Bluetooth or Bluetooth low energy (BLE) protocol. The electronic control circuitry can be configured to non-simultaneously transmit or receive data using the first or second antenna. The second antenna can be configured to obtain canister data from a canister removably attached to the housing. The canister data can include one or more of fill status of the canister, an indication that the canister is full, identification data, configuration data, date of manufacture of the canister, or date of first use of the canister. The electronic control circuitry can be configured to determine that the canister is connected to housing responsive to receiving the canister data. The electronic control circuitry can be configured to disallow activation of the negative pressure source responsive to determining that the canister is not connected to the housing.

The negative pressure wound therapy device of any of the preceding paragraphs and/or any of the devices, systems, or apparatuses disclosed herein can include one or more of the following features. The electronic control circuitry can include a first transceiver connected to the first and third antennas and a second transceiver connected to the second antenna. The electronic control circuitry can include a first matching circuitry interposed between the first transceiver and the first antenna. The first matching circuitry can be configured to match impedance of the first antenna with a first input impedance of the first transceiver. The electronic control circuitry can include a second matching circuitry interposed between the first transceiver and the second antenna. The second matching circuitry can be configured to match impedance of the second antenna with a second input impedance of the first transceiver. The electronic control circuitry can include a third matching circuitry interposed between the second transceiver and the third antenna. The third matching circuitry can be configured to match impedance of the third antenna with an input impedance of the second transceiver. The first matching circuitry can include at least one capacitor and at least one resistor. The third matching circuitry can include at least one capacitor, at least one inductor, and at least one resistor. The first antenna can be positioned in the top portion of the housing, and the second antenna can be positioned in a bottom portion of the housing. The canister can be configured to be removably supported by the bottom portion of the housing. The third antenna can be positioned in the top portion of the housing proximate to the first antenna. The first and third antennas can be positioned on a circuit board. The third antenna can include a planar inverted-F antenna.

A negative pressure wound therapy device can include a housing. The device can include a negative pressure source supported by the housing. The negative pressure source can be configured to provide negative pressure to a wound covered by a wound dressing. The device can include an electronic control circuitry supported by the housing. The electronic control circuitry can be configured to operate the negative pressure source. The electronic control circuitry can include a cellular antenna configured to facilitate wireless communications using long term evolution (LTE) communication protocol. The electronic control circuitry can include a global positioning system (GPS) antenna. The electronic control circuitry can include a transceiver configured to transmit or receive data using the cellular antenna and the GPS antenna. The electronic control circuitry can include a matching circuitry interposed between the cellular antenna and the transceiver. The matching circuitry can be configured to match impedance of the cellular antenna with an input impedance of the transceiver.

The negative pressure wound therapy device of any of the preceding paragraphs and/or any of the devices, systems, or apparatuses disclosed herein can include one or more of the following features. The matching circuitry can include a x-network or an L-network with a plurality of capacitors. The cellular antenna can be located in a bottom portion of the housing. The GPS antenna can be positioned in a top portion of the housing or a side portion of the housing. The transceiver is supported by a first printed circuit board (PCB) supported by the housing. The cellular antenna can be supported by a second PCB mounted to the first PCB. The second PCB can be electrically connected to the first PCB by a single connector of the first PCB. The single connector can provide mechanical support for the second PCB.

The negative pressure wound therapy device of any of the preceding paragraphs and/or any of the devices, systems, or apparatuses disclosed herein can include one or more of the following features. The device can include a first power source configured to provide power at least to the negative pressure source and a second power source configured to provide power at least to the transceiver. The transceiver can be configured to transmit location information using LTE or 5G communication protocol. The transceiver can be configured to transmit location information using the LTE or 5G communication protocol when the first power source does not provide power to the negative pressure source or any other component of the negative pressure wound therapy device. The transceiver can be configured to transmit location information using the LTE communication protocol that includes LTE Cat M1. The electronic control circuitry can be configured to disable the cellular antenna responsive to detecting that the negative pressure wound therapy device is being carried on an aircraft. The electronic control circuitry can be configured to detect that the negative pressure wound therapy device is being carried on an aircraft based on monitoring at least one of an altitude or vibration.

The negative pressure wound therapy device of any of the preceding paragraphs and/or any of the devices, systems, or apparatuses disclosed herein can include one or more of the following features. The GPS antenna can include an amplifier. The electronic control circuitry can include circuitry configured to provide power to the amplifier using the same connection of the GPS antenna on which data is communicated to the transceiver.

Disclosed herein are methods of operating a negative pressure wound therapy device of any of the preceding paragraphs and/or any of the devices, apparatuses, or systems disclosed herein.

Disclosed herein are kits that include the negative pressure wound therapy device of any of the preceding paragraphs and/or any of the devices, apparatuses, or systems disclosed herein and a canister and/or one or more wound dressings.

Any of the features, components, or details of any of the arrangements or embodiments disclosed in this application, including without limitation any of the apparatus embodiments and any of the negative pressure wound therapy embodiments disclosed herein, are interchangeably combinable with any other features, components, or details of any of the arrangements or embodiments disclosed herein to form new arrangements and embodiments.

DETAILED DESCRIPTION

Figure 1A:
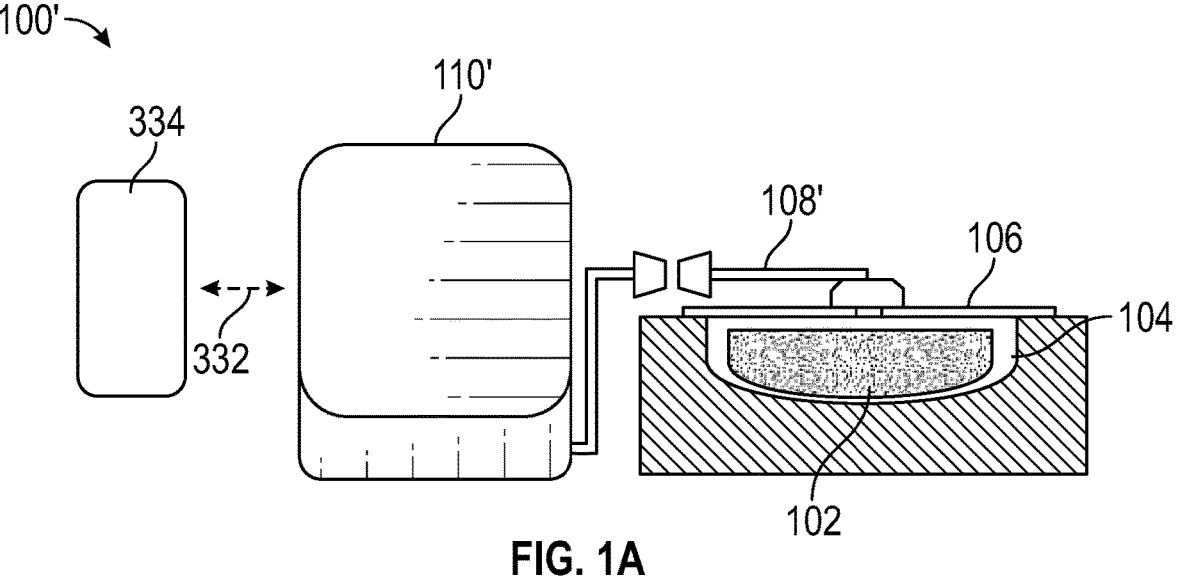
FIG. 1A illustrates a negative pressure wound therapy system.

Embodiments disclosed herein relate to systems and methods of treating and/or monitoring a wound. Some embodiments of the negative pressure wound therapy devices disclosed herein can include a negative pressure source configured to be connected and/or fluidically coupled, via a fluid flow path, to a wound covered by a wound dressing and provide negative pressure to a wound.

Throughout this specification reference is made to a wound. The term wound is to be broadly construed and encompasses open and closed wounds in which skin is torn, cut or punctured or where trauma causes a contusion, or any other superficial or other conditions or imperfections on the skin of a patient or otherwise that benefit from pressure treatment. A wound is thus broadly defined as any damaged region of tissue where fluid may or may not be produced. Examples of such wounds include, but are not limited to, abdominal wounds or other large or incisional wounds, either as a result of surgery, trauma, sternotomies, fasciotomies, or other conditions, dehisced wounds, acute wounds, chronic wounds, subacute and dehisced wounds, traumatic wounds, flaps and skin grafts, lacerations, abrasions, contusions, burns, diabetic ulcers, pressure ulcers, stoma, surgical wounds, trauma and venous ulcers or the like.

Embodiments of systems and methods disclosed herein can be used with topical negative pressure ("TNP") or reduced pressure therapy systems. Briefly, negative pressure wound therapy assists in the closure and healing of many forms of "hard to heal" wounds by reducing tissue oedema, encouraging blood flow and granular tissue formation, or removing excess exudate and can reduce bacterial load (and thus infection risk). In addition, the therapy allows for less disturbance of a wound leading to more rapid healing. TNP therapy systems can also assist in the healing of surgically closed wounds by removing fluid. TNP therapy can help to stabilize the tissue in the apposed position of closure. A further beneficial use of TNP therapy can be found in grafts and flaps where removal of excess fluid is important and close proximity of the graft to tissue is required in order to ensure tissue viability.

As used herein, reduced or negative pressure levels, such as –X mmHg, represent pressure levels relative to normal ambient atmospheric pressure, which can correspond to 760 mmHg (or 1 atm, 29.93 inHg, 101.325 kPa, 14.696 psi, etc.). Accordingly, a negative pressure value of –X mmHg reflects pressure that is X mmHg below 760 mmHg or, in other words, a pressure of (760–X) mmHg. In addition, negative pressure that is "less" or "smaller" than X mmHg corresponds to pressure that is closer to atmospheric pressure (for example, –40 mmHg is less than –60 mmHg). Negative pressure that is "more" or "greater" than –X mmHg corresponds to pressure that is further from atmospheric pressure (for example, –80 mmHg is more than –60 mmHg). In some cases, local ambient atmospheric pressure is used as a reference point, and such local atmospheric pressure may not necessarily be, for example, 760 mmHg.

Systems and methods disclosed herein can be used with other types of treatment in addition to or instead of reduced pressure therapy, such as irrigation, ultrasound, heat or cold, neuro stimulation, or the like. In some cases, disclosed systems and methods can be used for wound monitoring without application of additional therapy. Systems and methods disclosed herein can be used in conjunction with a dressing, including with compression dressing, reduced pressure dressing, or the like.

A healthcare provider, such as a clinician, nurse, or the like, can provide a TNP prescription specifying, for example, the pressure level or time of application. However, the healing process is different for each patient and the prescription may affect the healing process in a way the clinician or healthcare provider did not expect at the time of devising the prescription. A healthcare provider may try to adjust the prescription as the wound heals (or does not heal), but such process may require various appointments that can be time consuming and repetitive. Embodiments disclosed herein provide systems, devices, or methods of efficiently adjusting TNP prescriptions and delivering effective TNP therapy.

Wound Therapy System

FIG. 1A schematically illustrates a negative pressure wound treatment system 100' (sometimes referred to as a reduced or negative pressure wound therapy system, a TNP system, or a wound treatment system). In any implementations disclosed herein, though not required, the negative pressure wound treatment system 100' can include a wound filler 102 placed on or inside a wound 104 (which may be a cavity). The wound 104 can be sealed by a wound cover 106, which can be a drape, such that the wound cover 106 can be in fluidic communication with the wound 104. The wound filler 102 in combination with the wound cover 106 can be referred to as a wound dressing. A tube or conduit 108' (also referred to herein as a flexible suction adapter or a fluidic connector) can be used to connect the wound cover 106 with a wound therapy device 110' (sometimes as a whole or partially referred to as a "pump assembly") configured to supply reduced or negative pressure. The conduit 108' can be a single or multi lumen tube. A connector can be used to removably and selectively couple a conduit or tube of the device 110' with the conduit 108'.

In any of the systems disclosed herein, a wound therapy device can be canisterless, wherein, for example and without limitation, wound exudate is collected in the wound dressing or is transferred via a conduit for collection at another location. However, any of the wound therapy devices disclosed herein can include or support a canister.

Additionally, with any of the wound therapy systems disclosed herein, any of the wound therapy devices can be mounted to or supported by the wound dressing or adjacent to the wound dressing. The wound filler 102 can be any suitable type, such as hydrophilic or hydrophobic foam, gauze, inflatable bag, and so on. The wound filler 102 can be conformable to the wound 104 such that the wound filler 102 substantially fills the cavity of the wound 104. The wound cover 106 can provide a substantially fluid impermeable seal over the wound 104. The wound cover 106 can have a top side and a bottom side. The bottom side can adhesively (or in any other suitable manner) seal with the wound 104, for example by sealing with the skin around the wound 104. The conduit 108' or any other conduit disclosed herein can be formed from polyurethane, PVC, nylon, polyethylene, silicone, or any other suitable material.

The wound cover 106 can have a port (not shown) configured to receive an end of the conduit 108'. In some cases, the conduit 108' can otherwise pass through or under the wound cover 106 to supply reduced pressure to the wound 104 so as to maintain a desired level of reduced pressure in the wound 104. The conduit 108' can be any suitable article configured to provide at least a substantially sealed fluid flow pathway or path between the wound therapy device 110' and the wound cover 106, so as to supply the reduced pressure provided by the wound therapy device 110' to wound 104.

The wound cover 106 and the wound filler 102 can be provided as a single article or an integrated single unit. In some cases, no wound filler is provided and the wound cover by itself may be considered the wound dressing. The wound dressing can then be connected, via the conduit 108', to a source of negative pressure of the wound therapy device 110'. In some cases, though not required, the wound therapy device 110' can be miniaturized and portable, although larger conventional negative pressure sources (or pumps) can also be used.

The wound cover 106 can be located over a wound site to be treated. The wound cover 106 can form a substantially sealed cavity or enclosure over the wound. The wound cover 106 can have a film having a high water vapour permeability to enable the evaporation of surplus fluid, and can have a superabsorbing material contained therein to safely absorb wound exudate. In some cases, the components of the TNP systems described herein can be particularly suited for incisional wounds that exude a small amount of wound exudate.

The wound therapy device 110' can operate with or without the use of an exudate canister. In some cases, as is illustrated, the wound therapy device 110' can include an exudate canister. In some cases, configuring the wound therapy device 110' and conduit 108' so that the conduit 108' can be quickly and easily removed from the wound therapy device 110' can facilitate or improve the process of wound dressing or pump changes, if necessary. Any of the pump assemblies disclosed herein can have any suitable connection between the conduit 108' and the pump.

The wound therapy device 110' can deliver negative pressure of approximately −80 mmHg, or between about −20 mmHg and −200 mmHg. Note that these pressures are relative to normal ambient atmospheric pressure thus, −200 mmHg would be about 560 mmHg in practical terms. In some cases, the pressure range can be between about −40 mmHg and −150 mmHg. Alternatively, a pressure range of up to −75 mmHg, up to −80 mmHg or over −80 mmHg can be used. Also in some cases a pressure range of below −75 mmHg can be used. Alternatively, a pressure range of over approximately −100 mmHg, or even −150 mmHg, can be supplied by the wound therapy device 110'.

As will be described in greater detail below, the negative pressure wound treatment system 100' can be configured to provide a connection 332 to a separate or remote computing device 334. The connection 332 can be wired or wireless (such as, Bluetooth, Bluetooth low energy (BLE). Near-Field Communication (NFC), WiFi, or cellular). The remote computing device 334 can be a smartphone, a tablet, a laptop or another standalone computer, a server (such as, a cloud server), another pump device, or the like.

Figure 1B:
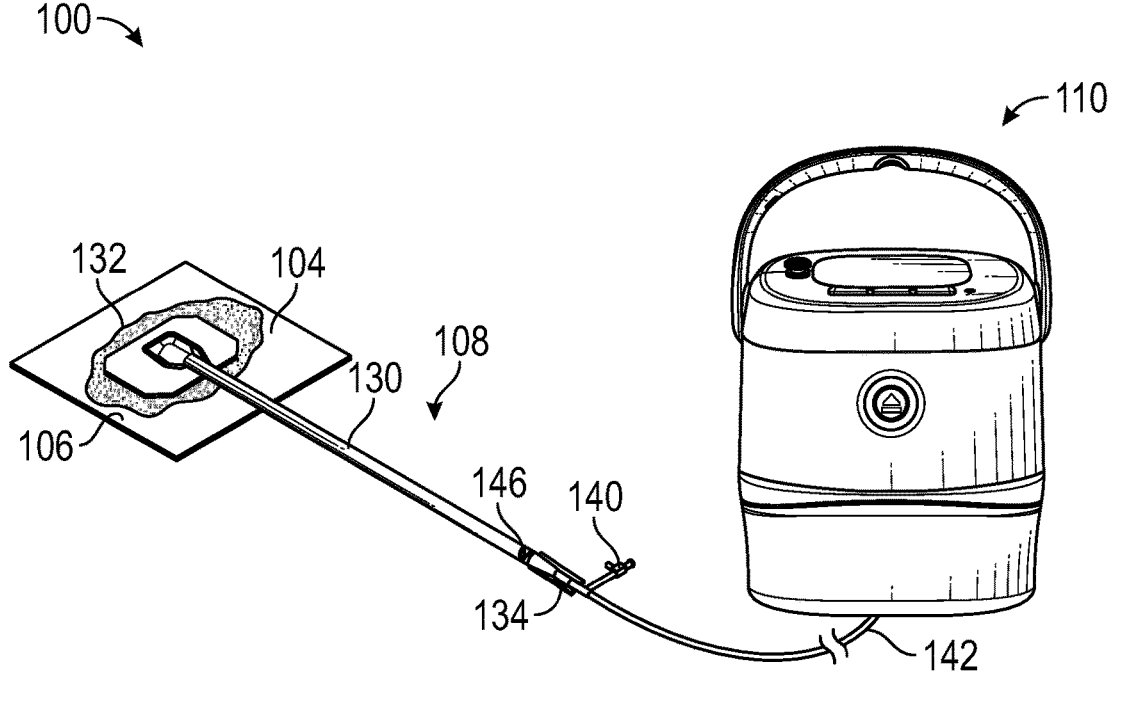
FIG. 1B illustrates another negative pressure wound therapy system.

FIG. 1B illustrates another negative pressure wound treatment system 100. The negative pressure wound treatment system 100 can have any of the components, features, or other details of any of the other negative pressure wound treatment system disclosed herein, including without limitation the negative pressure wound treatment system 100' illustrated in FIG. 1A or the negative pressure wound treatment system 400 illustrated in FIG. 4, in combination with or in place of any of the components, features, or other details of the negative pressure wound treatment system 100 shown in FIG. 1B and/or described herein. The negative pressure wound treatment system 100 can have a wound cover 106 over a wound 104 that can seal the wound 104. A conduit 108, such as a single or multi lumen tube can be used to connect the wound cover 106 with a wound therapy device 110 (sometimes as a whole or partially referred to as a "pump assembly") configured to supply reduced or negative pressure. The wound cover 106 can be in fluidic communication with the wound 104.

With reference to FIG. 1B, the conduit 108 can have a bridge portion 130 that can have a proximal end portion and a distal end portion (the distal end portion being closer to the wound 104 than the proximal end portion, and an applicator 132 at the distal end of the bridge portion 130 forming the flexible suction adapter (or conduit) 108. A connector 134 can be disposed at the proximal end of the bridge portion 130, so as to connect to at least one of the channels that can extend along a length of the bridge portion 130 of the conduit 108 shown in FIG. 1B. A cap 140 can be coupled with a portion of the conduit 108 and can, in some cases, as illustrated, be attached to the connector 134. The cap 140 can be useful in preventing fluids from leaking out of the proximal end of the bridge portion 130. The conduit 108 can be a Soft Port manufactured by Smith & Nephew. As mentioned, the negative pressure wound treatment system 100 can include a source of negative pressure, such as the device 110, capable of supplying negative pressure to the wound 104 through the conduit 108. Though not required, the device 110 can also include a canister or other container for the storage of wound exudates and other fluids that can be removed from the wound.

The device 110 can be connected to the connector 134 via a conduit or tube 142. In use, the applicator 132 can be placed over an aperture formed in a cover 106 that is placed over a suitably-prepared wound or wound 104. Subsequently, with the wound therapy device 110 connected via the tube 142 to the connector 134, the wound therapy device 110 can be activated to supply negative pressure to the wound. Application of negative pressure can be applied until a desired level of healing of the wound is achieved.

The bridge portion 130 can comprise an upper channel material or layer positioned between an upper layer and an intermediate layer, with a lower channel material or layer positioned between the intermediate layer and a bottom layer. The upper, intermediate, and lower layers can have elongate portions extending between proximal and distal ends and can include a material that is fluid-impermeable, for example polymers such as polyurethane. It will of course be appreciated that the upper, intermediate, and lower layers can each be constructed from different materials, including semi-permeable materials. In some cases, one or more of the upper, intermediate, and lower layers can be at least partially transparent. In some instances, the upper and lower layers can be curved, rounded or outwardly convex over a majority of their lengths.

The upper and lower channel layers can be elongate layers extending from the proximal end to the distal end of the bridge 130 and can each preferably comprise a porous material, including for example open-celled foams such as polyethylene or polyurethane. In some cases, one or more of the upper and lower channel layers can be comprised of a fabric, for example a knitted or woven spacer fabric (such as a knitted polyester 3D fabric, Baltex 7970®, or Gehring 879®) or a nonwoven material, or terry-woven or loop-pile materials. The fibers may not necessarily be woven, and can include felted and flocked (including materials such as Flotex®) fibrous materials. The materials selected are preferably suited to channeling wound exudate away from the wound and for transmitting negative pressure or vented air to the wound site, and can also confer a degree of kinking or occlusion resistance to the channel layers. In one example, the upper channel layer can include an open-celled foam such as polyurethane, and the lower channel layer can include a fabric. In another example, the upper channel layer is optional, and the system can instead be provided with an open upper channel. The upper channel layer can have a curved, rounded or upwardly convex upper surface and a substantially flat lower surface, and the lower channel layer can have a curved, rounded or downwardly convex lower surface and a substantially flat upper surface.

The fabric or material of any components of the bridge 130 can have a three-dimensional (3D) structure, where one or more types of fibers form a structure where the fibers extend in all three dimensions. Such a fabric can in some cases aid in wicking, transporting fluid or transmitting negative pressure. In some cases, the fabric or materials of the channels can include several layers of material stacked or layered over each other, which can in some cases be useful in preventing the channel from collapsing under the application of negative pressure. The materials used in some implementations of the conduit 108 can be conformable and pliable, which can, in some cases, help to avoid pressure ulcers and other complications which can result from a wound treatment system being pressed against the skin of a patient.

The distal ends of the upper, intermediate, and lower layers and the channel layers can be enlarged at their distal ends (to be placed over a wound site), and can form a "teardrop" or other enlarged shape. The distal ends of at least the upper, intermediate, and lower layers and the channel layers can also be provided with at least one through aperture. This aperture can be useful not only for the drainage of wound exudate and for applying negative pressure to the wound, but also during manufacturing of the device, as these apertures can be used to align these respective layers appropriately.

In some implementations, a controlled gas leak 146 (sometimes referred to as gas leak, air leak, or controlled air leak) can be disposed on the bridge portion 130, for example at the proximal end thereof. This air leak 146 can comprise an opening or channel extending through the upper layer of the bridge portion 130, such that the air leak 146 is in fluidic communication with the upper channel of the bridge portion 130. Upon the application of suction to the conduit 108, gas (such, as air) can enter through the gas leak 146 and move from the proximal end of the bridge portion 130 to the distal end of the bridge portion along the upper channel of the bridge portion 130. The gas can then be suctioned into the lower channel of the bridge portion 130 by passing through the apertures through the distal ends of the upper, intermediate, and lower layers.

The air leak 146 can include a filter. Preferably, the air leak 146 is located at the proximal end of the bridge portion 130 so as to minimize the likelihood of wound exudate or other fluids coming into contact and possibly occluding or interfering with the air leak 146 or the filter. In some instances, the filter can be a microporous membrane capable of excluding microorganisms and bacteria, and which may be able to filter out particles larger than 45 µm. Preferably, the filter can exclude particles larger than 1.0 µm, and more preferably, particles larger than 0.2 µm. Advantageously, some implementations can provide for a filter that is at least partially chemically-resistant, for example to water, common household liquids such as shampoos, and other surfactants. In some cases, reapplication of vacuum to the suction adapter or wiping of the exposed outer portion of the filter may be sufficient to clear any foreign substance occluding the filter. The filter can be composed of a suitably-resistant polymer such as acrylic, polyethersulfone, or polytetrafluoroethylene, and can be oleophobic or hydrophobic. In some cases, the gas leak 146 can supply a relatively constant gas flow that does not appreciably increase as additional negative pressure is applied to the conduit 108. In instances of the negative pressure wound treatment system 100 where the gas flow through the gas leak 146 increases as additional negative pressure is applied, preferably this increased gas flow will be minimized and not increase in proportion to the negative pressure applied thereto. Further description of such bridges, conduits, air leaks, and other components, features, and details that can be used with any implementations of the negative pressure wound treatment systems disclosed herein are found in U.S. Pat. No. 8,801,685, which is incorporated by reference in its entirety as if fully set forth herein.

Any of the wound therapy devices (such as, the device 110 or 110') disclosed herein can provide continuous or intermittent negative pressure therapy. Continuous therapy can be delivered at above 0 mmHg, −25 mmHg, −40 mmHg, −50 mmHg, −60 mmHg, −70 mmHg, −80 mmHg, −90 mmHg, −100 mmHg, −120 mmHg, −125 mmHg, −140 mmHg, −160 mmHg, −180 mmHg, −200 mmHg, or below −200 mmHg. Intermittent therapy can be delivered between low and high negative pressure set points (sometimes referred to as setpoint). Low set point can be set at above 0 mmHg, −25 mmHg, −40 mmHg, −50 mmHg, −60 mmHg, −70 mmHg, −80 mmHg, −90 mmHg, −100 mmHg, −120 mmHg, −125 mmHg, −140 mmHg, −160 mmHg, −180 mmHg, or below −180 mmHg. High set point can be set at above −25 mmHg, −40 mmHg, −50 mmHg, −60 mmHg, −70 mmHg, −80 mmHg, −90 mmHg, −100 mmHg, −120 mmHg, −125 mmHg, −140 mmHg, −160 mmHg, −180 mmHg, −200 mmHg, or below −200 mmHg. During intermittent therapy, negative pressure at low set point can be delivered for a first time duration, and upon expiration of the first time duration, negative pressure at high set point can be delivered for a second time duration. Upon expiration of the second time duration, negative pressure at low set point can be delivered. The first and second time durations can be same or different values.

In operation, the wound filler 102 can be inserted into the cavity of the wound 104, and wound cover 106 can be placed so as to seal the wound 104. The wound therapy device 110' can provide negative pressure to the wound cover 106, which can be transmitted to the wound 104 via the wound filler 102. Fluid (such as, wound exudate) can be drawn through the conduit 108' and stored in a canister. In some cases, fluid is absorbed by the wound filler 102 or one or more absorbent layers (not shown).

Wound dressings that can be utilized with the pump assembly and systems of the present application include Renasys-F, Renasys-G, Renasys AB, and Pico Dressings available from Smith & Nephew. Further description of such wound dressings and other components of a negative pressure wound therapy system that can be used with the pump assembly and systems of the present application are found in U.S. Patent Publication Nos. 2012/0116334, 2011/0213287, 2011/0282309, 2012/0136325, U.S. Pat. No. 9,084,845, and International App. No. PCT/EP2020/078376, each of which is incorporated by reference in its entirety as if fully set forth herein. In some cases, other suitable wound dressings can be utilized.

Figure 2A:
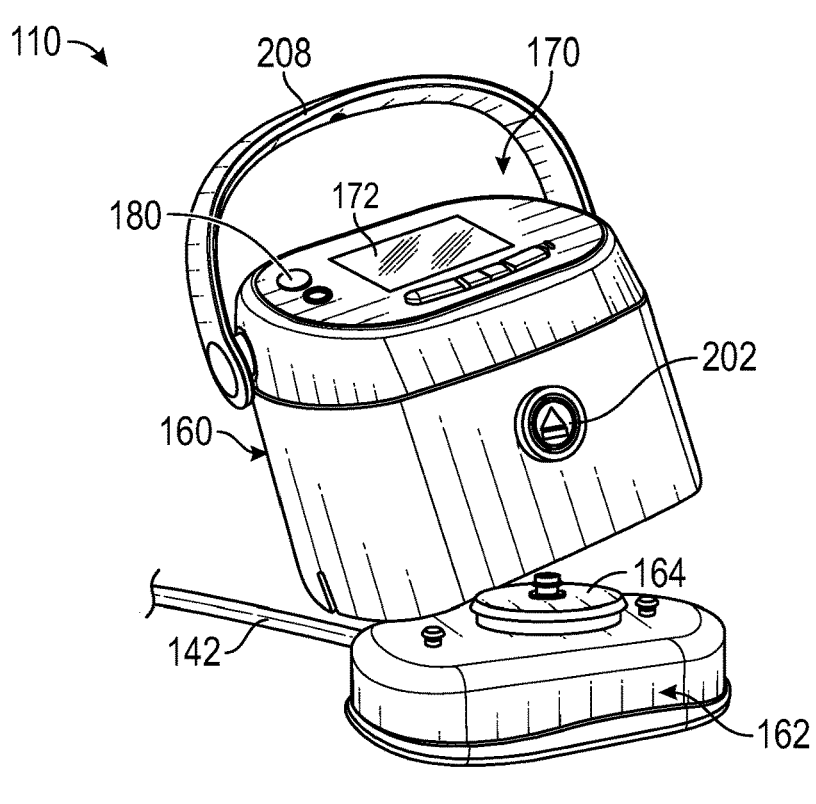
FIG. 2A is an isometric view of a negative pressure wound therapy device and canister, showing the canister detached from the pump assembly of the device.
Figure 2B:
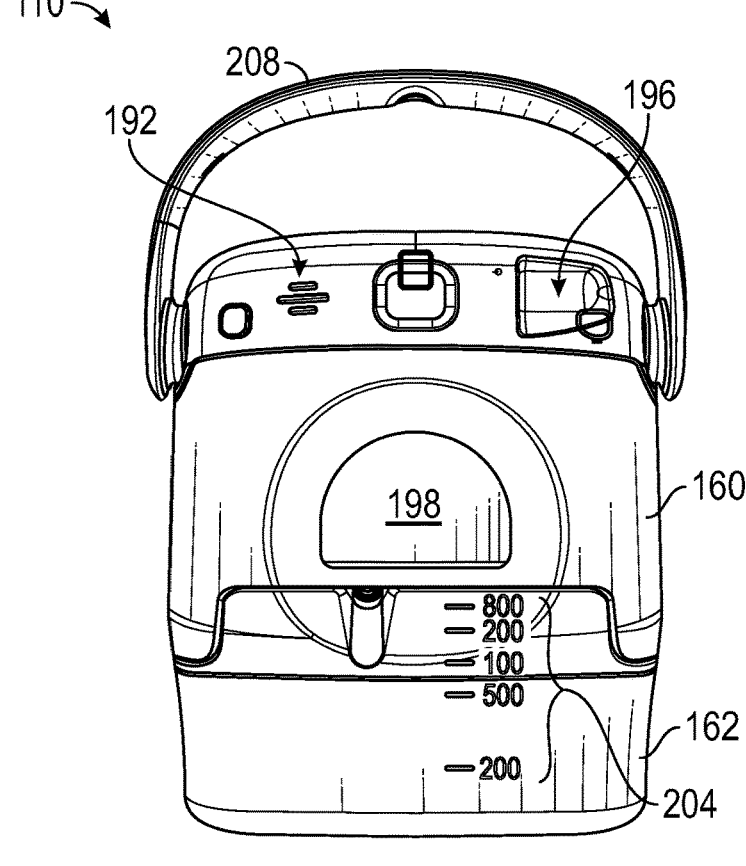
FIG. 2B is a back view of the negative pressure wound therapy device shown in FIG. 2A.
Figure 2C:
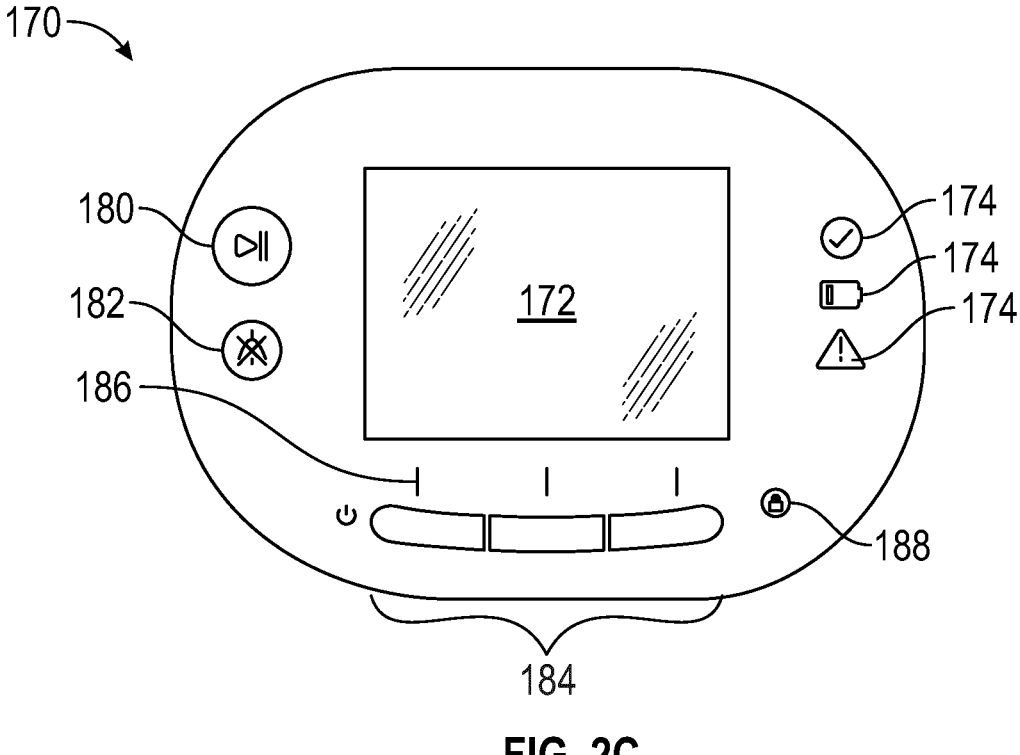
FIG. 2C illustrates a top surface of the negative pressure wound therapy device shown in FIG. 2A, showing a user interface.

FIGS. 2A-2C show the negative pressure wound therapy device 110. As illustrated, a pump assembly 160 and canister 162 can be connected, thereby forming the wound therapy device 110. With reference to FIG. 2C, the pump assembly 160 can include an interface panel 170 having a display 172, one or more indicators 174, or one or more controls or buttons, including, for example and without limitation, a therapy start and pause button 180 or an alarm/alert mute button 182. The interface panel 170 can have one or more input controls or buttons 184 (three being shown) that can be used to control any functions of the pump assembly 160 or the interface panel 170. For example and without limitation, one or more of the buttons 184 can be used to turn the pump assembly 160 on or off, to start or pause therapy, to operate and monitor the operation of the pump assembly 160, to scroll through menus displayed on the display 172, or to control or perform other functions. In some cases, the command buttons 184 can be programmable, and can be made from a tactile, soft rubber.

Additionally, the interface panel 170 can have visual indicators 186 that can indicate which of the one or more buttons 184 is active. The interface panel 170 can also have a lock/unlock control or button 188 that can be configured to selectively lock or unlock the functionality of the various buttons (e.g., buttons 184) or the display 172. For example, therapy setting adjustment can be locked/unlocked via the lock/unlock control 188. When the lock/unlock button 188 is in the locked state, depressing one or more of the various other buttons or the display will not cause the pump assembly 160 to change any display functions or performance functions of the device. This way, the interface panel 170 will be protected from inadvertent bumping or touching of the various buttons or display. The interface panel 170 can be located on an upper portion of the pump assembly 160, for example and without limitation on an upward facing surface of the pump assembly 160.

The display 172, which can be a screen such as an LCD screen, can be mounted in a middle portion of the interface panel 170. The display 172 can be a touch screen display. The display 172 can support playback of audiovisual (AV) content, such as instructional videos, and render a number of screens or graphical user interfaces (GUIs) for configuring, controlling, and monitoring the operation of the pump assembly 160.

The one or more indicators 174 can be lights (such as, LEDs) and can be configured to provide a visual indication of alarm conditions and or a status of the pump. For example and without limitation, the one or more indicators 174 can be configured to provide a visual indication of a status of the pump assembly 160 or other components of the negative pressure wound treatment system 100, including without limitation the conduit 108 or the wound cover 106 (such as, to provide an indication of normal operation, low battery, a leak, canister full, blockage, overpressure, or the like). Any one or more suitable indicators can be additionally or alternatively used, such as visual, audio, tactile indicator, and so on.

FIG. 2B shows a back or rear view of the wound therapy device 110 shown in the FIG. 2A. As shown, the pump assembly 160 can include a speaker 192 for producing sound. For example and without limitation, the speaker 192 can generate an acoustic alarm in response to deviations in therapy delivery, non-compliance with therapy delivery, or any other similar or suitable conditions or combinations thereof. The speaker 192 can provide audio to accompany one or more instructional videos that can be displayed on the display 172.

The pump assembly 160 can be configured to provide easy access (such as, an access door on the casing of the pump assembly) to one or more filters of the pump assembly 160, such as antibacterial filters. This can enable a user (such as, a healthcare provider or patient) to more easily access, inspect or replace such filters. The pump assembly 160 can also include a power jack (or socket) 196 for providing power to the pump assembly 160 or for charging and recharging an internal power source (such as, a battery). Some implementations of the pump assembly 160 can include a disposable or renewable power source, such as one or more batteries, so that no power jack is needed. The pump assembly 160 can have a recess 198 formed therein to facilitate gripping of the pump assembly 160.

The canister 162 can hold fluid aspirated from the wound 104. For example, the canister 162 can have an 800 mL (or approximately 800 mL) capacity, or from a 300 mL or less capacity to a 1000 mL or more capacity, or any capacity level in this range. The canister 162 can include a tubing for connecting to the conduit 108 in order to form a fluid flow path. The canister 162 can be replaced with another canister, such as when the canister 162 has been filled with fluid. With reference to FIG. 2A, the wound therapy device 110 can include a canister inlet tube 142 (also referred to herein as a dressing port connector) in fluid communication with the canister 162. For example and without limitation, the canister inlet tube 142 can be used to connect with the conduit 108.

The canister 162 can be selectively coupleable and removable from the pump assembly 160. With reference to FIG. 2A, in some cases, a canister release button 202 can be configured to selectively release the canister 162 from the pump assembly 160. With reference to FIG. 2B, the canister 162 can have one or more fill lines or graduations 204 to indicate to the user and amount of fluid or exudate stored within the canister 162.

The wound therapy device 110 can have a handle 208 that can be used to lift or carry the wound therapy device 110. The handle 208 can be coupled with the pump assembly 160 and can be rotatable relative to the wound therapy device 110 so that the handle can be rotated upward for lifting or carrying the wound therapy device 110 or the pump assembly 160, or rotated into a lower profile in a more compact position when the handle is not being used. In some cases, the handle 208 can be coupled with the pump assembly 160 in a fixed position. The handle 208 can be coupled with an upper portion of the pump assembly 160 or can be removable from the wound therapy device 110.

Figure 3:
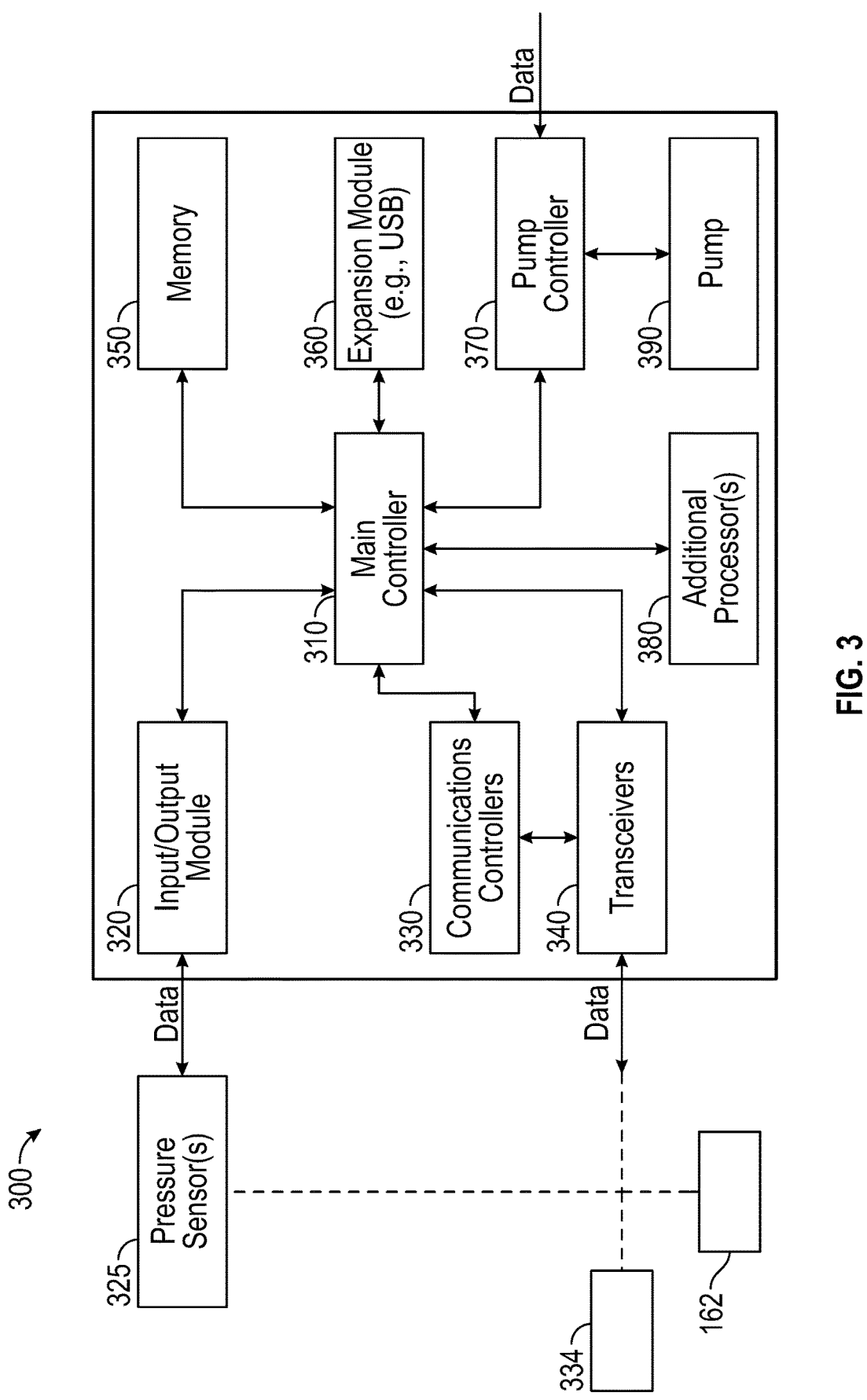
FIG. 3 illustrates a schematic of a control system of a negative pressure wound therapy device.

FIG. 3 illustrates a schematic of a control system 300 that can be employed in any of the wound therapy devices described herein, such as in the wound therapy device 110. Electrical components can operate to accept user input, provide output to the user, operate the pressure source, provide connectivity, and so on. A first processor (such as, a main controller 310) can be responsible for user activity, and a second processor (such as, a pump controller 370) can be responsible for controlling another device, such as a pump 390.

An input/output (I/O) module 320 can be used to control an input and/or output to another component or device, such as the pump 390, one or more sensors (for example, one or more pressure sensors 325 configured to monitor pressure in one or more locations of the fluid flow path), or the like. For example, the I/O module can receive data from one or more sensors through one or more ports, such as serial (for example, I2C), parallel, hybrid ports, and the like. Any of the pressure sensors can be part of the wound therapy device or the canister. In some cases, any of the pressure sensors 325 can be remote to the wound therapy device, such as positioned at or near the wound (for example, in the dressing or the conduit connecting the dressing to the wound therapy device). In such implementations, any of the remote pressure sensors can communicate with the I/O module over a wired connection or with one or more transceivers 340 over a wireless connection.

The main controller 310 can receive data from and provide data to one or more expansion modules 360, such as one or more USB ports, SD ports, Compact Disc (CD) drives, DVD drives, FireWire ports, Thunderbolt ports, PCI Express ports, and the like. The main controller 310, along with other controllers or processors, can store data in memory 350 (such as one or more memory modules), which can be internal or external to the main controller 310. Any suitable type of memory can be used, including volatile or non-volatile memory, such as RAM, ROM, magnetic memory, solid-state memory, Magnetoresistive random-access memory (MRAM), and the like.

The main controller 310 can be a general purpose controller, such as a low-power processor or an application specific processor. The main controller 310 can be configured as a "central" processor in the electronic architecture of the control system 300, and the main controller 310 can coordinate the activity of other processors, such as the pump controller 370, one or more communications controllers 330, and one or more additional processors 380. The main controller 310 can run a suitable operating system, such as a Linux, Windows CE, VxWorks, etc.

The pump controller 370 can control the operation of a pump 390, which can generate negative or reduced pressure. The pump 390 can be a suitable pump, such as a diaphragm pump, peristaltic pump, rotary pump, rotary vane pump, scroll pump, screw pump, liquid ring pump, diaphragm pump operated by a piezoelectric transducer, voice coil pump, and the like. The pump controller 370 can measure pressure in a fluid flow path, using data received from one or more pressure sensors 325, calculate the rate of fluid flow, and control the pump. The pump controller 370 can control the pump actuator (such as, a motor) so that a desired level of negative pressure is achieved in the wound 104. The desired level of negative pressure can be pressure set or selected by the user. The pump controller 370 can control the pump (for example, pump motor) using pulse-width modulation (PWM) or pulsed control. A control signal for driving the pump can be a 0-100% duty cycle PWM signal. The pump controller 370 can perform flow rate calculations and detect alarms. The pump controller 370 can communicate information to the main controller 310. The pump controller 370 can be a low-power processor.

Any of the one or more communications controllers 330 can provide connectivity (such as, a wired or wireless connection 332). The one or more communications controllers 330 can utilize one or more transceivers 340 for sending and receiving data. The one or more transceivers 340 can include one or more antennas, optical sensors, optical transmitters, vibration motors or transducers, vibration sensors, acoustic sensors, ultrasound sensors, or the like. Any of the one or more transceivers 340 can function as a communications controller. In such case, the one or more communications controllers 330 can be omitted. Any of the one or more transceivers 340 can be connected to one or more antennas that facilitate wireless communication. The one or more communications controllers 330 can provide one or more of the following types of connections: Global Positioning System (GPS), cellular connectivity (for example, 2G, 3G, LTE, 4G, 5G, or the like), NFC, Bluetooth (or BLE) connectivity, radio frequency identification (RFID), wireless local area network (WLAN), wireless personal area network (WPAN), WiFi connectivity, Internet connectivity, optical connectivity (for example, using infrared light, barcodes, such as QR codes, etc.), acoustic connectivity, ultrasound connectivity, or the like. Connectivity can be used for various activities, such as pump assembly location tracking, asset tracking, compliance monitoring, remote selection, uploading of logs, alarms, and other operational data, and adjustment of therapy settings, upgrading of software or firmware, pairing, and the like.

Any of the one or more communications controllers 330 can provide dual GPS/cellular functionality. Cellular functionality can, for example, be 3G, 4G, or 5G functionality. The one or more communications controllers 330 can communicate information to the main controller 310. Any of the one or more communications controllers 330 can include internal memory or can utilize memory 350. Any of the one or more communications controllers 330 can be a low-power processor.

The control system 300 can store data, such as GPS data, therapy data, device data, and event data. This data can be stored, for example, in memory 350. This data can include patient data collected by one or more sensors. The control system 300 can track and log therapy and other operational data. Such data can be stored, for example, in the memory 350.

Using the connectivity provided by the one or more communications controllers 330, the control system 300 can upload any of the data stored, maintained, or tracked by the control system 300 to a remote computing device, such as the device 334. The control system 300 can also download various operational data, such as therapy selection and parameters, firmware and software patches and upgrades, and the like (for example, via the connection to the device

334). The one or more additional processors 380, such as processor for controlling one or more user interfaces (such as, one or more displays), can be utilized. In some cases, any of the illustrated or described components of the control system 300 can be omitted depending on an embodiment of a wound monitoring or treatment system in which the control system 300 is used.

Using connectivity provided by the one or more communications controllers 330, the control system 330 can communicate with a canister, such as the canister 162. The canister 162 can report operating status to the control system 330, such as, whether the canister is full, level of fluid stored in the canister, or the like.

Any of the negative pressure wound therapy devices described herein can include one or more features disclosed in U.S. Pat. No. 9,737,649 or U.S. Patent Publication No. 2017/0216501, each of which is incorporated by reference in its entirety.

Multiple Dressing Negative Wound Therapy

Figure 4:
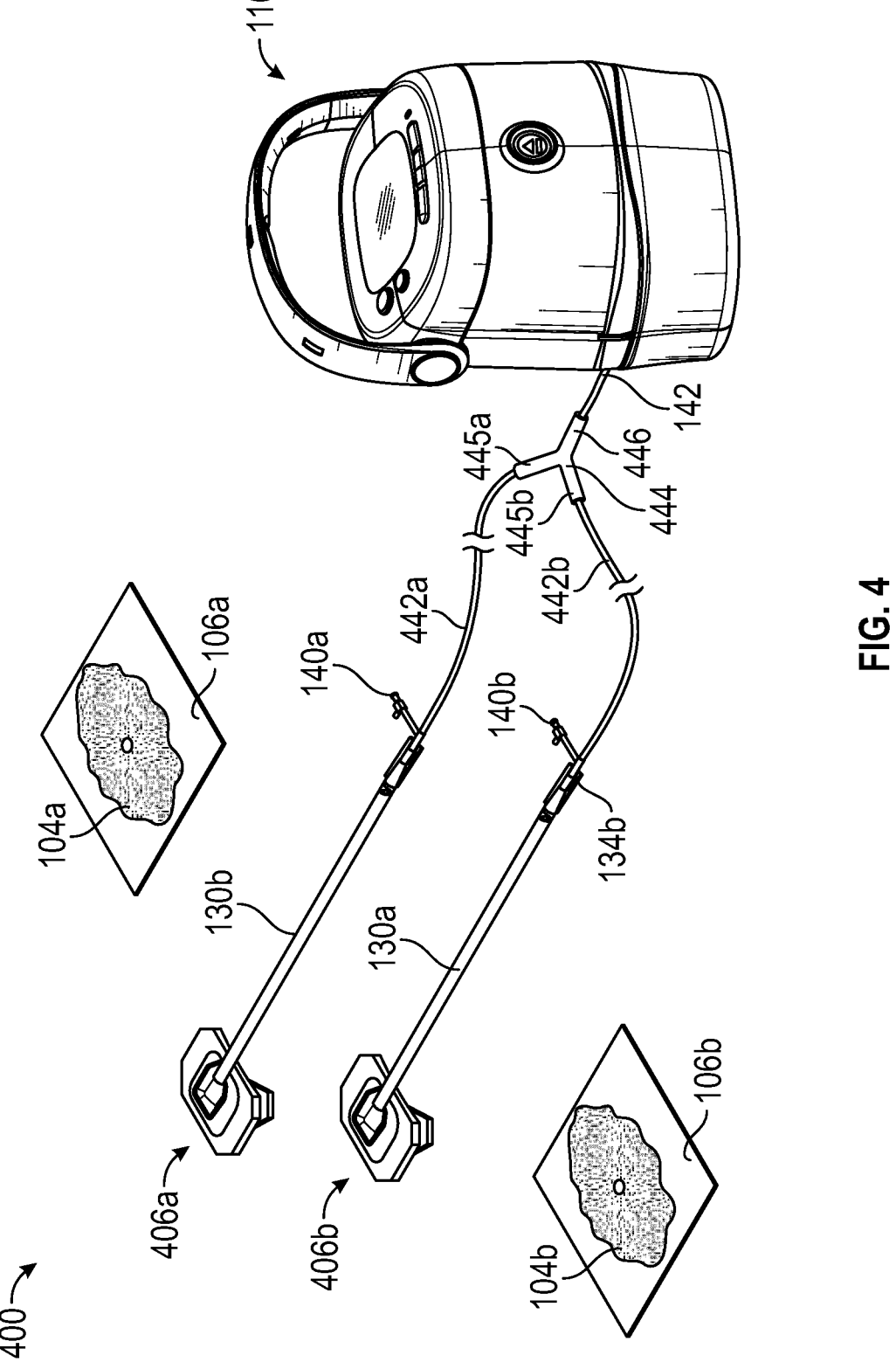
FIG. 4 illustrates another negative pressure wound therapy system.

FIG. 4 illustrates another negative pressure wound treatment system 400. The system 400 can include a wound therapy device capable of supplying negative pressure to the wound site or sites, such as wound therapy device 110. The wound therapy device 110 can be in fluidic communication with one or more wound dressings 406a, 406b (collectively referred to as 406) so as to supply negative pressure to one or more wounds, such as the wounds 104a and 104b. A first fluid flow path can include components providing fluidic connection from the wound therapy device 110 to the first wound dressing 406a. As a non-limiting example, the first fluid flow path can include the path from the wound dressing 406a to the wound therapy device 110 or the path from the first wound dressing 406a to an inlet 446 of a branching attachment (or connector) 444 in fluidic connection with the wound therapy device 110. Similarly, a second fluid flow path can include components providing fluidic connection from the wound therapy device 110 to the second wound dressing 406b.

The system 400 can be similar to the system 100 with the exception that multiple wounds 104a and 140b are being treated by the system 400. The system 400 can include any one or more of the components of the system 100, which are illustrated in FIG. 4 with appended letter "a" or "b" to distinguish between the first and second wounds (such as, the wounds 104a and 104b, the covers 106a and 106b). As illustrated, the system 400 can include a plurality of wound dressings 406a, 406b (and corresponding fluid flow paths) in fluidic communication with the wound therapy device 110 via a plurality of suction adapters, such as the adapter 108. The suction adapters can include any one or more of the components of the adapter 108, which are illustrated in FIG. 4 with appended letter "a" or "b" to distinguish between the first and second wounds (such as, the bridge portions 130a and 130b, the connectors 134a and 134b, and the caps 140a and 140b).

The wound therapy device 110 can be fluidically coupled via the tube 142 with the inlet 446 of the connector 444. The connector 444 can be fluidically coupled via branches 445a, 445b and tubes or conduits 442a, 442b with the connectors 134a, 134b, which can be fluidically coupled with the tubes or conduits 130a, 130b. The tubes or conduits 130a, 130b can be fluidically coupled with the dressings 406a, 406b. Once all conduits and dressing components are coupled and operably positioned, the wound therapy device 110 can be activated, thereby supplying negative pressure via the fluid flow paths to the wounds 430a, 430b. Application of negative pressure can be applied until a desired level of healing of the wounds 430 is achieved. Although two wounds and wound dressing are illustrated in FIG. 4, some implementations of the wound therapy device 110 can provide treatment to a single wound (for instance, by closing the unused branch 445a or 445b of the connector 444) or to more than two wounds (for instance, by adding branches to the connector 444).

The system 400 can include one or more features disclosed in U.S. Patent Publication No. 2020/0069850 or International Publication No. WO2018/167199, each of which is incorporated by reference in its entirety.

Multiple Communications Modes

A negative pressure wound therapy device, such as the pump assembly 160, can communicate with multiple devices or components. The communicated data can include operational data related to the provision of TNP therapy. Communication of data by the pump assembly 16 can, for instance, facilitate remote monitoring and troubleshooting, which can improve effectiveness of TNP therapy.

For example, as described herein, the pump assembly 160 can communicate with the remote computing device 334 over the connection 332. The connection 332 can be a wireless connection, such as Bluetooth (or BLE), WiFi, etc. The pump assembly 160 can communicate with the canister 162, as described herein. Same or different communication protocols can be implemented by the pump assembly 160 for communicating with multiple devices or negative pressure wound therapy system components.

Figure 5A:
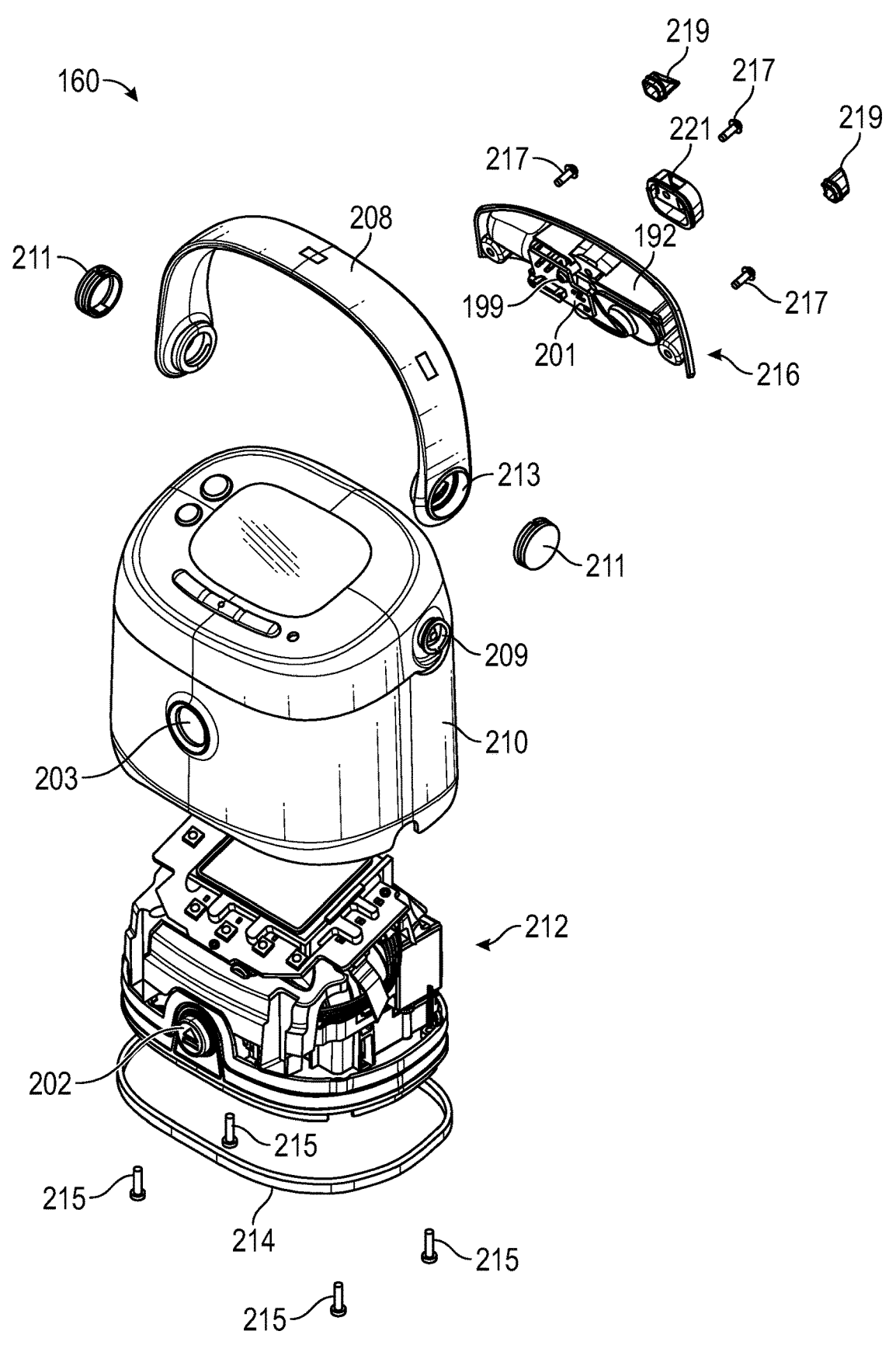
FIGS. 5A-5I illustrate exploded views of the negative pressure wound therapy device of FIG. 2A.

FIG. 5A illustrates an exploded view of the pump assembly 160. Some arrangements of the pump assembly 160 have been designed to facilitate the ease with which components and sub-components of the pump assembly 160 can be removed from the pump assembly 160 for cleaning, servicing, replacing, or otherwise. Some arrangements of the pump assembly 160 are designed such that the various components and/or sub-assemblies are arranged and assembled in the pump assembly 160 in a modular fashion to make the various components and sub-assemblies easier to remove, clean, and/or service. In some arrangements, the pump assembly 160 can have a housing 210 which is sized and configured to enclose at least a core assembly 212. The housing 210 can be made from acrylonitrile butadiene styrene, or any other desirable or suitable materials.

A core base seal 214 can be used to seal the core assembly 212 to the housing 210 of the pump assembly 160. A plurality of screws or other fasteners 215 can be used to couple a core assembly 212 with the housing 210. A rear trim assembly 216 can be coupled with the housing 210 using one or more fasteners 217 that can have one or more screw or fastener covers 219. Some arrangements of the rear trim assembly 216 can have a USB port 199 or other wired connection ports coupled with a printed circuit board (PCB) 201 that can be included in the rear trim assembly 216. The rear trim assembly 216 can include the speaker 192 and can have other components or connectors, buttons, switches, or inputs. A USB cover 221 can be removably coupled with the USB port. A power cord (not shown) can be removably connected to the power jack 196 and extend through the rear trim assembly 216 and be electrically coupled with electrical components of the rear trim assembly 216. Connecting the power cord to the rear trim assembly 216 through the power jack 196 can, in some arrangements, make it easier to remove and replace a damaged power cord as compared to models in which the power cord is connected directly to the internal electronic components within the pump, which can require that the service technician disassemble the pump to replace the power cord. Such arrangement can make it easier to remove and replace a damaged power jack 196. In some arrangements of the pump assembly 160, the service technician need only remove and replace the rear trim assembly 216 to replace the power jack 196.

The handle 208 can be coupled with posts 209 of the housing 210 configured to pivot relative to the housing 210. In some arrangements, the handle can be made from a thermoplastic elastomer or any other suitable or desired material. In some arrangements, the handle can be configured to simply clip or snap onto the housing 210. In some arrangements, the handle 208 can be configured to rotate relative to the housing 210, or can be rigidly (nonrotatably) attached to the housing 210. The handle 208 can include one or more detents to facilitate retaining the handle in the upright position. In some arrangements, two or more handle caps 211 can be used to couple the handle 208 with the posts 209 of the housing 210 or can be used to cover the depressions or recesses 213 in the handle 208. The canister release button 202 can extend through an opening 203 in the housing 210.

As described herein, the pump assembly 160 can communicate with the remote computing device 334. The communication can be performed over the connection 332 using a communication protocol, such as Bluetooth (or BLE), WiFi, etc. For security and integrity, including protection of patient medical data, ensuring that correct remote computing device is connected to correct pump assembly (as there may be many remote computing devices in a vicinity of a pump assembly and vice versa), or the like, it can be advantageous to pair or bond a remote computing device with the pump assembly. Pairing can be performed before or as part of establishing the connection to the remote computing device.

In some cases, pairing can be performed using "just works" approach by which a known key (for example, 0 or another suitable value) is exchanged between the pump assembly and the remote computing device. The temporary key can then be used to establish the remote communication, encrypt the remote communication, or the like. While this approach may not require user interaction, it may not be secure and/or facilitate connection between the correct devices, or the like. These shortcoming may be due to the key being known.

In some cases, pairing can be performed using "passkey" approach by which a key is passed between the remote computing device and the pump assembly by the user. For example, a random key can be generated and displayed on the pump assembly (or on the remote computing device). The user can enter the key into the remote computing device (or into the pump assembly). The key can then be used to establish the remote communication, encrypt the remote communication, or the like. While this approach may facilitate security, connection between the correct devices, or the like, it may undesirably require user interaction.

In some cases, pairing can be performed by exchanging pairing data between the remote computing device and the pump assembly device using a communication protocol that is different from that used by the connection 332. For example, a key can be generated and exchanged between the remote computing device and the pump assembly using inductive coupling, NFC (for instance, passive NFC), RFID (for example, passive RFID), optical communication, or the like. As another example, an IP address (and/or credentials) can be exchanged to establish a WiFi connection, which may be used to then establish a Bluetooth (or BLE) connection. This can be performed when the remote computing device is positioned in physical contact with or within a threshold distance of one or more regions of the pump assembly. The key (or IP address) can be randomly generated. The key (or IP address) can be used to establish the remote communication, encrypt the remote communication, or the like. The remote communication can utilize Bluetooth (or BLE), WiFi, or the like. Advantageously, this approach can facilitate security, connection between the correct devices, etc. while not requiring any user interaction or requiring minimal user interaction.

In some cases, the user may be requested to authorize or confirm the pairing. This can be done by pressing a button of the pump assembly 160, such as any of buttons 184, touching the display 172, or the like. Alternatively or additionally, the user can authorize the pairing on the remote computing device. Additional approaches for exchanging pairing data are disclosed in International Patent Application No. PCT/EP2020/078551, which is incorporated by reference in its entirety.

Figure 5B:
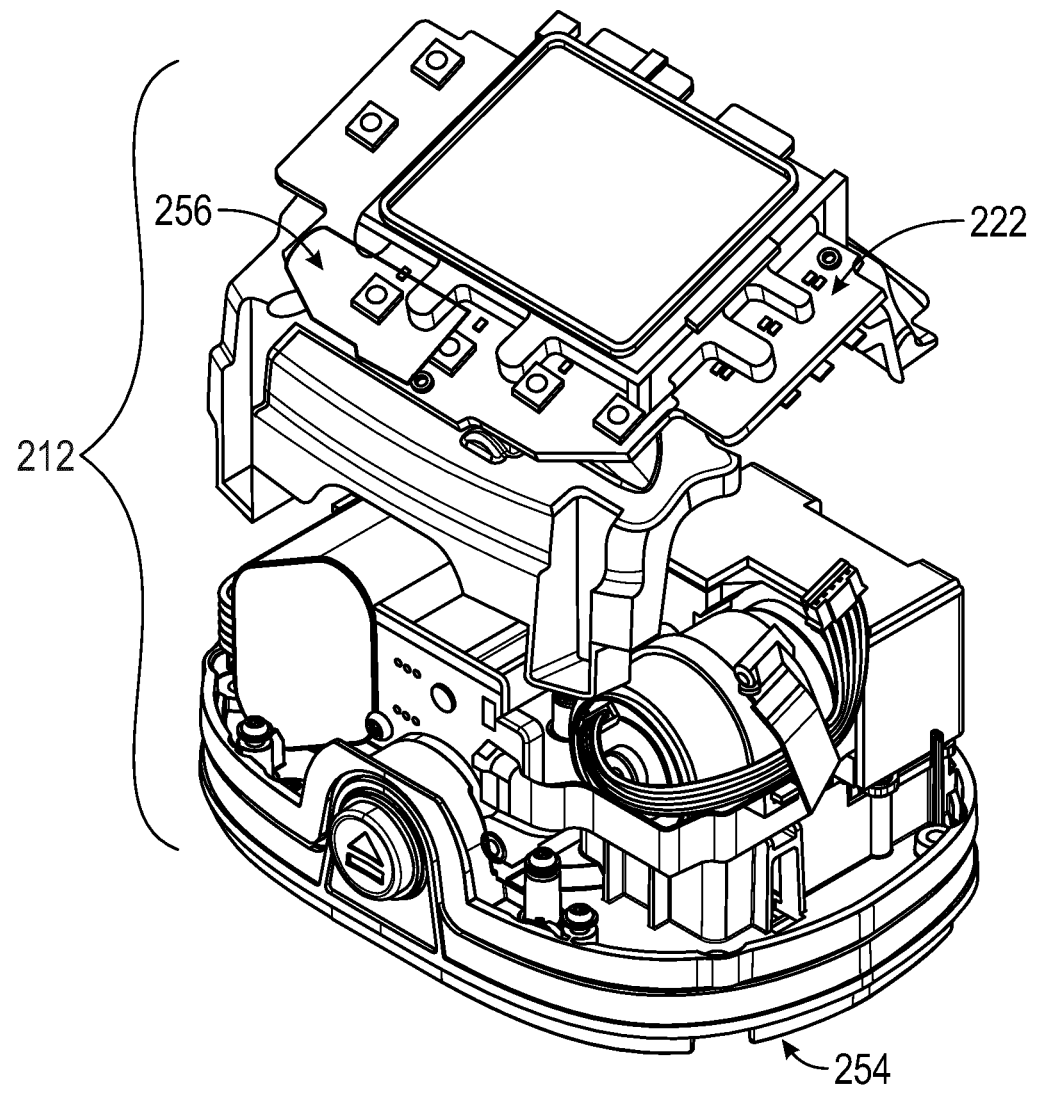
Figure 5C:
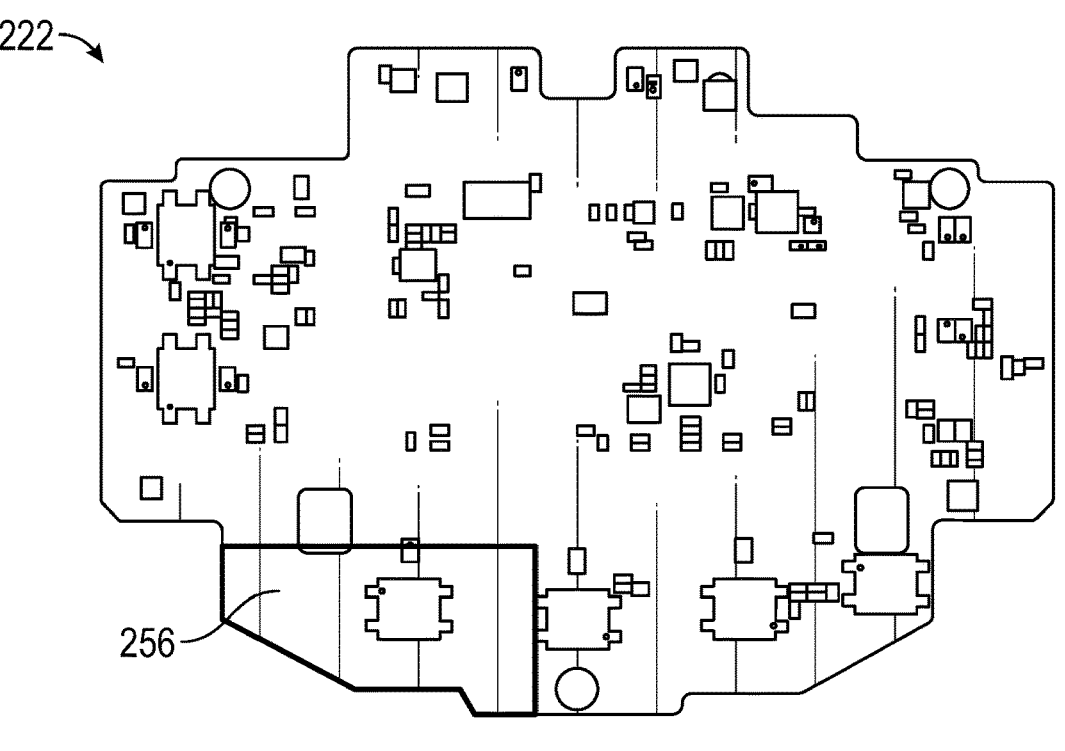
Figure 5D:
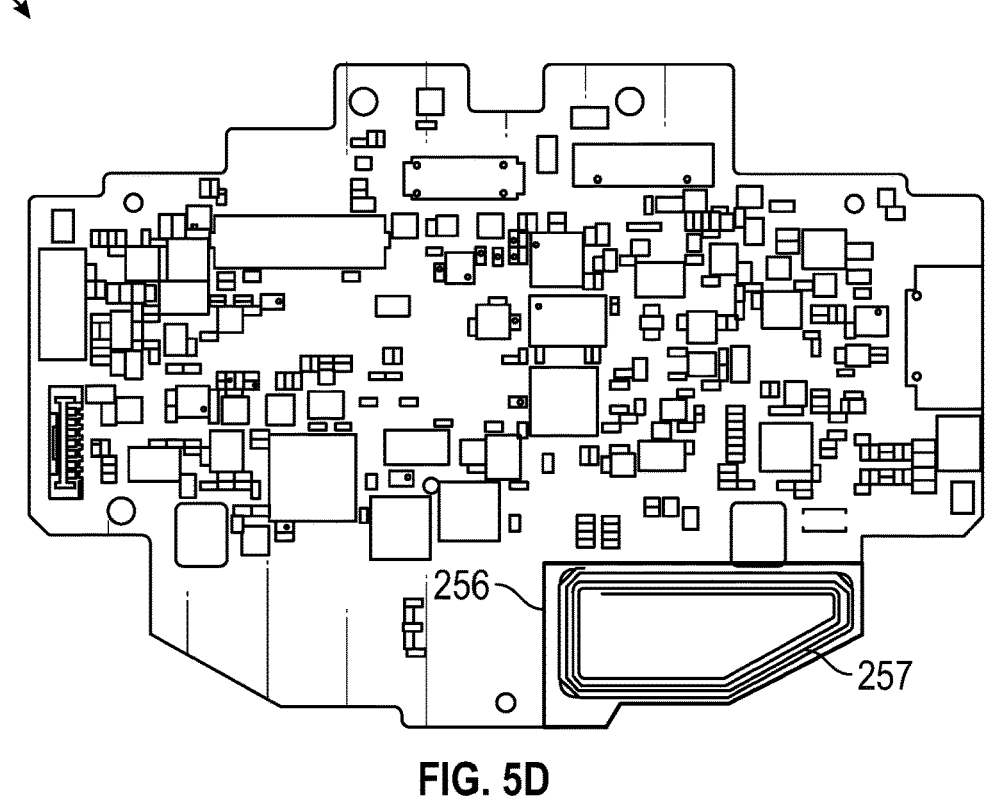

FIG. 5B illustrates the core assembly 212 and a lower core assembly 254. A printed circuit board (PCB) 222, which can be positioned on the top of the core assembly 212, can support a plurality of electronic components, such as one or more of the components of the control system 300 illustrated in FIG. 3. The PCB 222 can be single-sided (such as, include a single layer of conductive material, such as copper), double-sided (such as, include two layers of conductive material on the top and bottom sides), or multi-layered (such as, include more than two layers of conductive material). One or more antennas for facilitating wireless communications can be supported by or connected to the PCB 222 (such as, to a transceiver supported by the PCB). As described herein, an antenna can be positioned on the PCB 222. With reference to FIGS. 5C and 5D (as well as FIGS. 5G and 5H), which illustrate mirrored views of the top side (for instance, supporting the screen) and bottom side of the PCB 222 respectively, an antenna 257 can be positioned in the region 256. As is illustrated, the antenna 257 can be positioned on the bottom side (or the side facing toward the canister) of the PCB 222. The antenna 257 can facilitate NFC communication. As is illustrated, the antenna 257 can be a coil (or loop) antenna.

The region 256 can correspond to a location or area for pairing the pump assembly 160 with a remote computing device, as described herein. For example, pairing data (such as, a key) for communicating with the remote computing device 334 over a Bluetooth (or BLE) connection can be exchanged via an NFC connection facilitated by an antenna located in the region 256. To facilitate convenience and security, the region 256 can be located in a corner of the pump assembly 160, such as, in the bottom left corner. In some cases, the region 256 can be located in another corner or position.

The region 256 can correspond to coverage area(s) of one or more antennas configured to facilitate the pairing. Coverage area of an antenna, such as the antenna 257, can be associated with space in which the antenna is configured to receive and/or transmit radio frequency (RF) waves or signals. Coverage area of the antenna used for pairing can be limited to include the area enclosed by a portion of the housing 210 overlying the region 256 and/or volume extending a threshold distance away from such area. The threshold distance can be a small distance away from the surface of the housing 210, such as 0.5 cm or less, 1 cm or less, 2 cm or less or more, 3 cm or less or more, 4 cm or less or more, 5 cm or less or more, 10 cm or less or more, 15 cm or less or more. Unless a remote computing device is positioned within the coverage area of the antenna (such as, in contact with such area or within such volume), pairing will not be initiated. Limiting the coverage area of the one or more antennas can improve security (for example, by preventing hacking) and promote connection between the correct devices. In some cases, to further promote security, the one or more regions may not be marked by any indicia (such that, the user may need to a priori know the location(s) of the one or more regions to initiate the pairing). Additional approaches for limiting the coverage area are disclosed in International Patent Application No. PCT/EP2020/078551 (published as WO 2021/074052), which is incorporated by reference in its entirety.

Figure 5F:
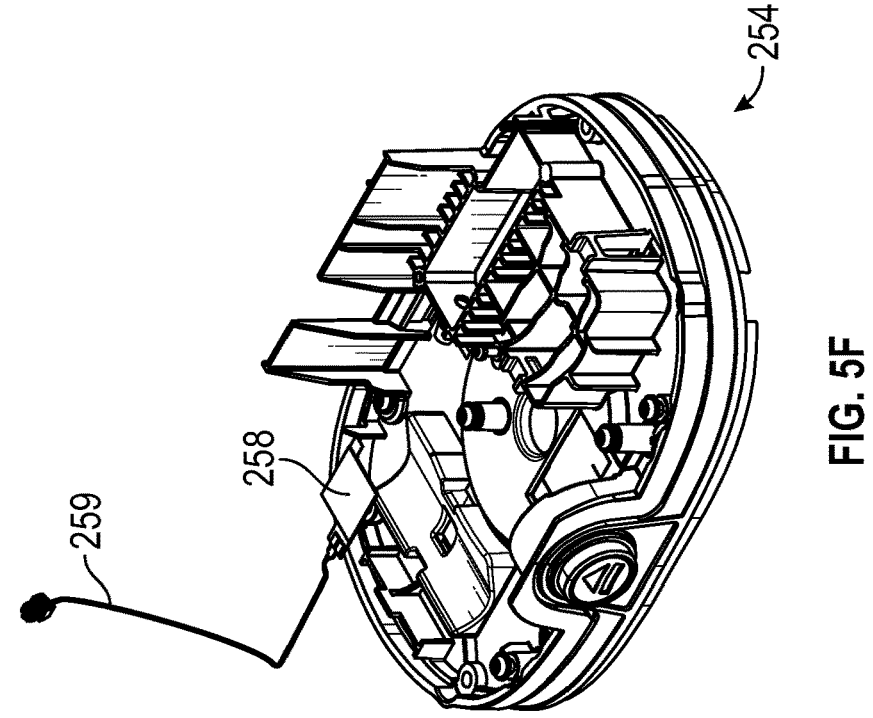
Figure 5E:
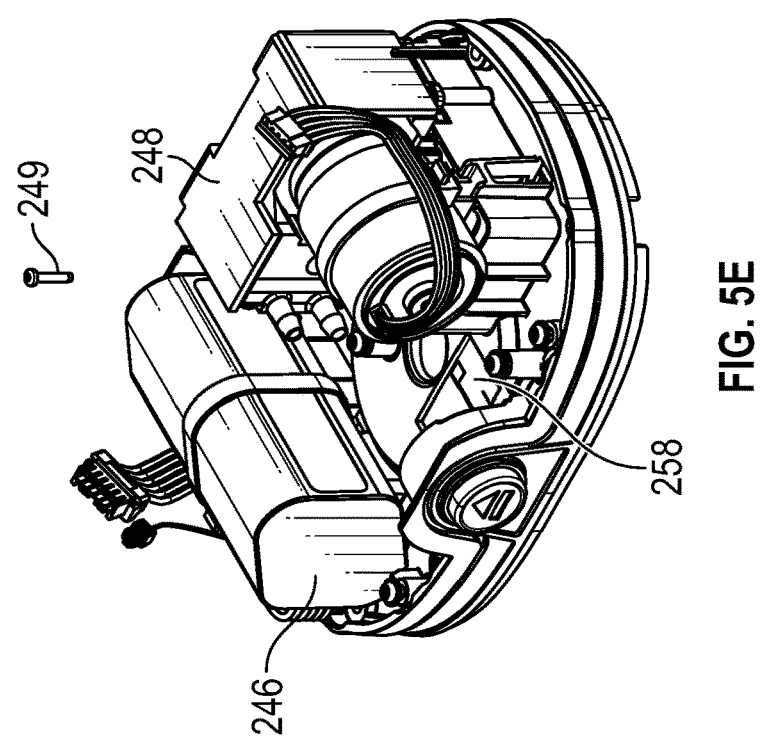

With reference to FIGS. 5E and 5F, the core assembly 212 can include a battery module 246 and a pump motor assembly 248. The pump motor assembly 248 can include a pump motor. The pump motor assembly 248 can include an inlet tubing connector and an outlet tubing connector to which tubing can be coupled. Some arrangements of the pump motor assembly 248 can include a pump controller, such as the pump controller 370. The battery module 246 can be any suitable battery pack and can include single use and rechargeable type batteries such as lithium ion batteries. Some arrangements of the battery can include lithium ion 18650 or 21600 cells, or any other type of battery that has plentiful power supply, has good power density for size, and/or is lightweight. The battery module can include a carefully designed charging circuitry with full redundancy due to the inherent risks of lithium ion battery technology, and can be configured to operate across a limited temperature range.

The pump motor assembly 248 can include a pump motor and a controller. The pump can be a diaphragm pump or any other desired or suitable type of pump, including a rotary pump, a peristaltic pump, a piezoelectric pump, or otherwise. Some arrangements of diaphragm pumps are well suited to the flow rates and pressures required, have a long maintenance-free service life, and are relatively efficient and quiet in operation.

The battery module 246 and/or the pump motor assembly 248 can be coupled with or supported by the lower core assembly 254. One or more fasteners 249 and/or cable ties can be used to couple the pump motor assembly 248 with the other components of the core assembly 212.

Figure 5G:
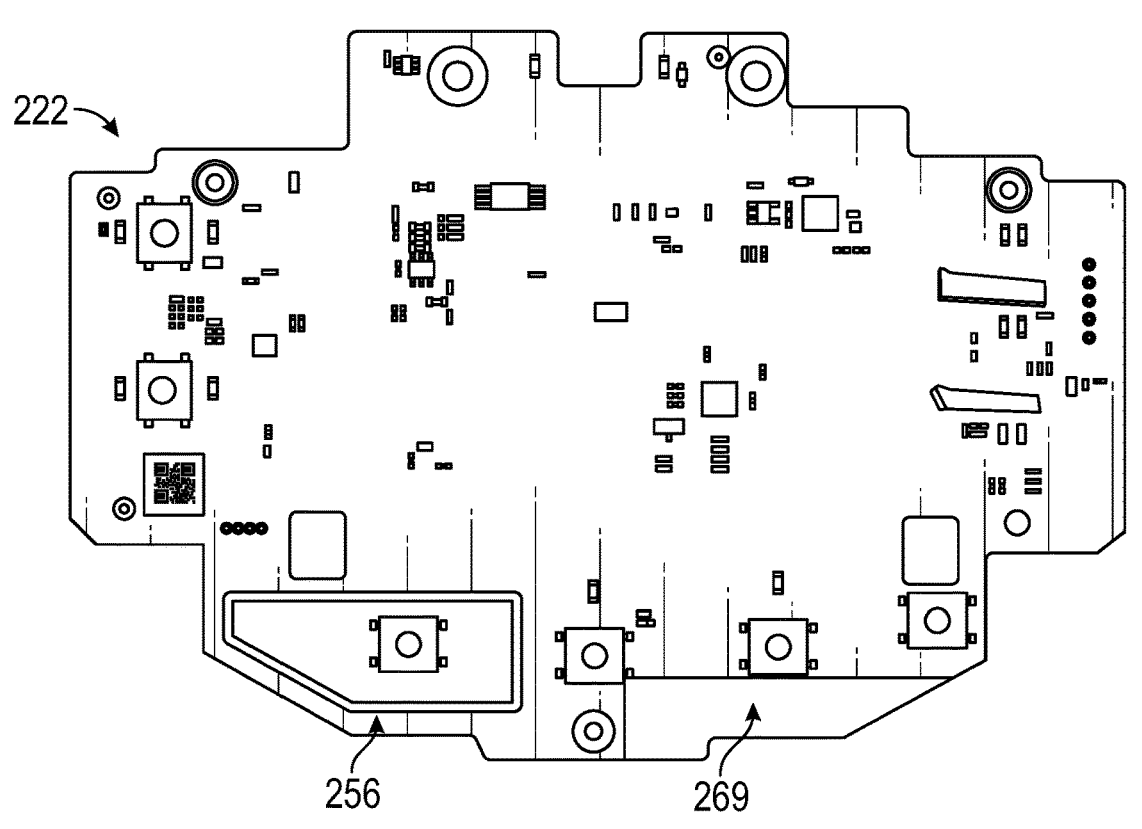
Figure 5H:
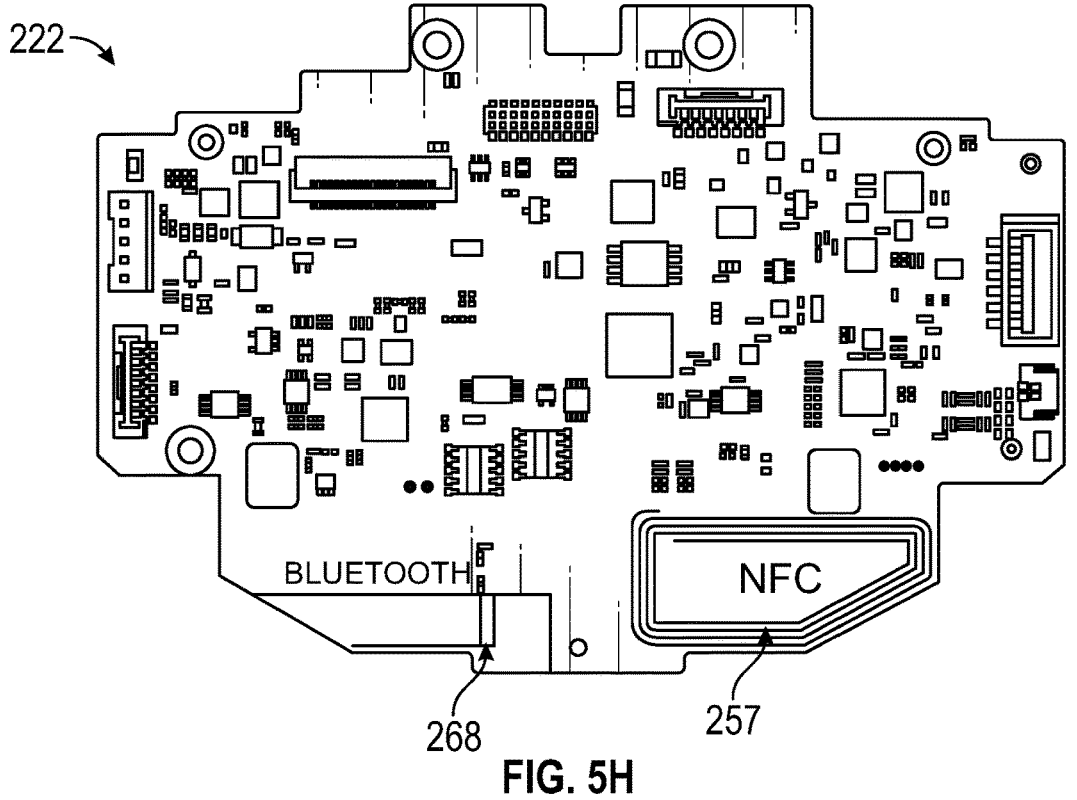
Figure 5I:
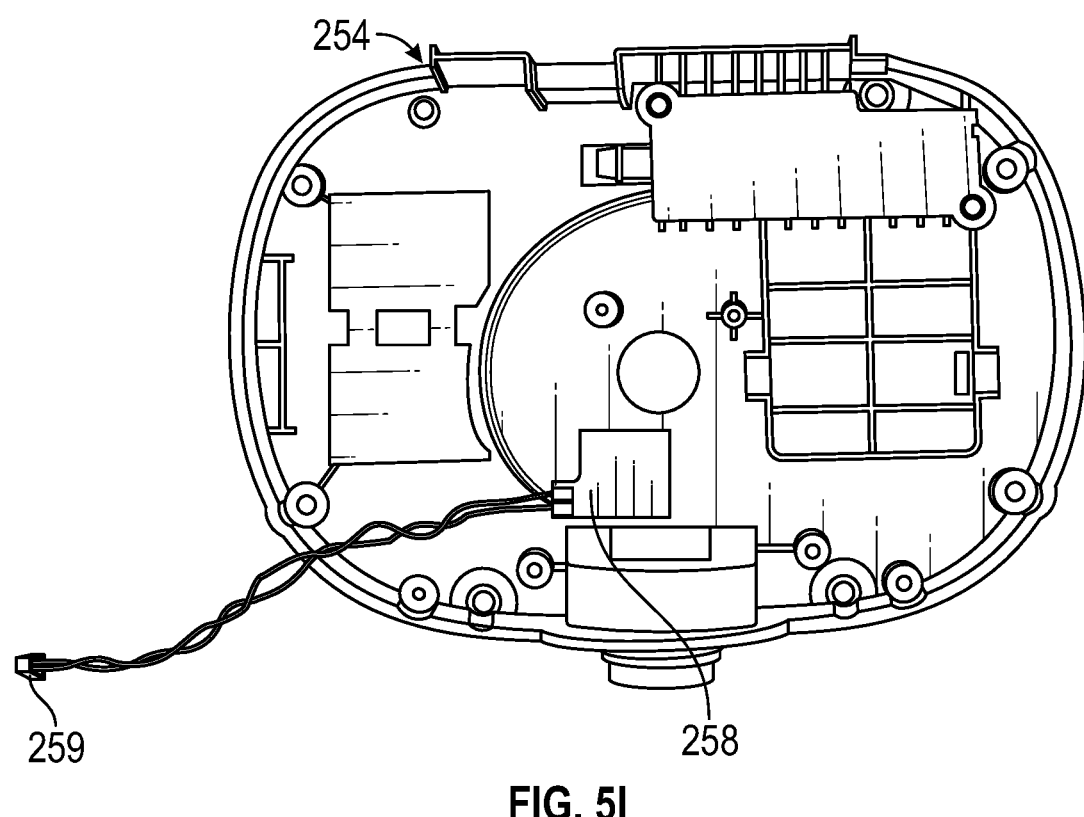

An antenna 258 can be provided as illustrated in FIGS. 5E, 5F, and 5I. The antenna 258 can be configured to facilitate communication with a canister, such as the canister 162. The pump assembly 160 can receive data relating to the status of the canister 162 (such as whether the canister is full or the level of fluid in the canister), configuration data (such as, canister capacity), identification data (such as, batch code or serial number of the canister), date of manufacture of the canister (which can be a timestamp), date of first use of the canister (which can be a timestamp), or the like. Such data can be individually or collectively referred to as canister data. In some implementations, exchange of canister data between the pump assembly 160 and the canister 162 (such as, using the antenna 258 and a corresponding antenna in the canister) can indicate presence or positioning of the canister. For instance, reading the canister identification data can provide indication of the canister being connected to the pump assembly 160 (such as, to the housing of the pump assembly 160 as illustrated in FIG. 2A). If it is determined that the canister is not connected and provision of negative pressure wound therapy is requested, an indication can be provided that the canister has not been detected. Provision of therapy (such as, activating the negative pressure source) may be disallowed until a canister has been connected and its presence has been detected.

In some cases, the antenna 258 can support communication using NFC, RFID, or the like. The antenna 258 can be a coil or loop antenna. To efficiently communicate with the canister, the antenna 258 can be positioned at the bottom of the core assembly 212. As illustrated in FIGS. 5F and 5I, the antenna 258 can be positioned near the inlet (located in the hole shown in FIGS. 5F and 5I) of the lower core assembly 254. The antenna 258 can be supported by or be adjacent to the lower core assembly 254. The antenna 258 can plug into the PCB 222 via a connector 259. NFC antenna of the canister can be positioned at or near the top portion of the canister, such as in the filter assembly 164 illustrated in FIG. 2A. Additional approaches for communicating the with the canister are disclosed in co-pending Patent Application No. EP 21382346.1 filed on Apr. 21, 2021, titled "Canister Status Determination for Negative Pressure Wound Therapy Devices," which is incorporated by reference in its entirety.

As described herein, the antenna 257 can be positioned at or near the top portion of the pump assembly 160 to facilitate communication with a remote computing device, such as the remote computing device 334. The antenna 257 can be used for exchanging pairing data with the remote computing device. In addition to pairing data, a uniform resource locator (URL) or similar information can be transmitted to the remote computing device. This additional information can be used to access a website for obtaining instructions related to the pump assembly 160, downloading an app or the like for communicating with the pump assembly 160, or the like. For instance, the antenna 257 can support a near-field protocol, which may function over a limited range or distance (such as, 4 cm or less). In some instances, the near-field protocol supported by the antenna 257 can include one or more of ISO/IEC 14443, ISO/IEC 15693, ISO/IEC 18092, or ISO/IEC 21481. The antenna 257 can be part of a passive NFC device (or a tag). A passive NFC tag may be configured to only send data. The passive tag can send the pairing data (such as, a key stored in the memory) to the remote computing device positioned in proximity of the tag (such as, within the coverage area of the antenna 257). Subsequent to pairing, communication with the remote computing device can be performed using another communication protocol than that provided by the antenna 257. Another communication protocol that facilitates exchange of data over a longer distance (such as, Bluetooth or BLE) can be utilized subsequent to pairing. The pump assembly 160 can include another antenna (such, as an antenna 268 illustrated in FIG. 5H) to support another communication protocol, such as a Bluetooth or BLE antenna. A Bluetooth or BLE antenna can be supported by the PCB 222 (such, as be a trace on the PCB 222) or positioned within the housing, as described herein. With reference to FIGS. 5G and 5H, the antenna 268 can be positioned on the bottom side of the PCB 222 in the region 269. The antenna 268 can be a planar inverted-F antenna (PIFA) as shown in FIG. 5H.

In some instances, one or more pressure sensors can be positioned in the fluid flow path remotely from the pump assembly 160. For example, one or more pressure sensors can be positioned at or near the wound (for example, in the dressing or the conduit connecting the dressing to the pump assembly 160). Further approaches to positioning the one or more pressure sensors are described in International Patent Application No. PCT/EP2020/072663 and U.S. Patent Publication No. 2021/0001019, each of which is incorporated by reference in its entirety. The one or more pressure sensors can communicate with the pump assembly 160 similarly to the remote computing device 334. For instance, the one or more pressure sensors can communicate with the pump assembly 160 using Bluetooth (or BLE). Pairing of the one or more pressure sensors can be performed similarly to pairing the remote computing device. Alternatively, in some instances, the pump assembly 160 can pair with a pressure sensor by varying provision of negative pressure, as described in International Patent Application No. PCT/EP2020/072663.

As described herein, a further antenna (such as, the antenna 258) can be positioned at or near the bottom portion of the pump assembly 160 to facilitate communication with a canister, such as the canister 162. The antenna 258 can be part of an active NFC device (or tag), which can be configured to both send and receive data. A passive NFC tag can be positioned in the canister 162 and send canister data. In some cases, the antennas 257 and 258 can support the same communication protocol, such as the same near-field protocol. In such case, only one of antennas 257 or 258 may be configured to operate (such as, receive or transmit data) at a given time in order to reduce or remove any interference resulting from both antennas operating simultaneously.

Figure 6A:
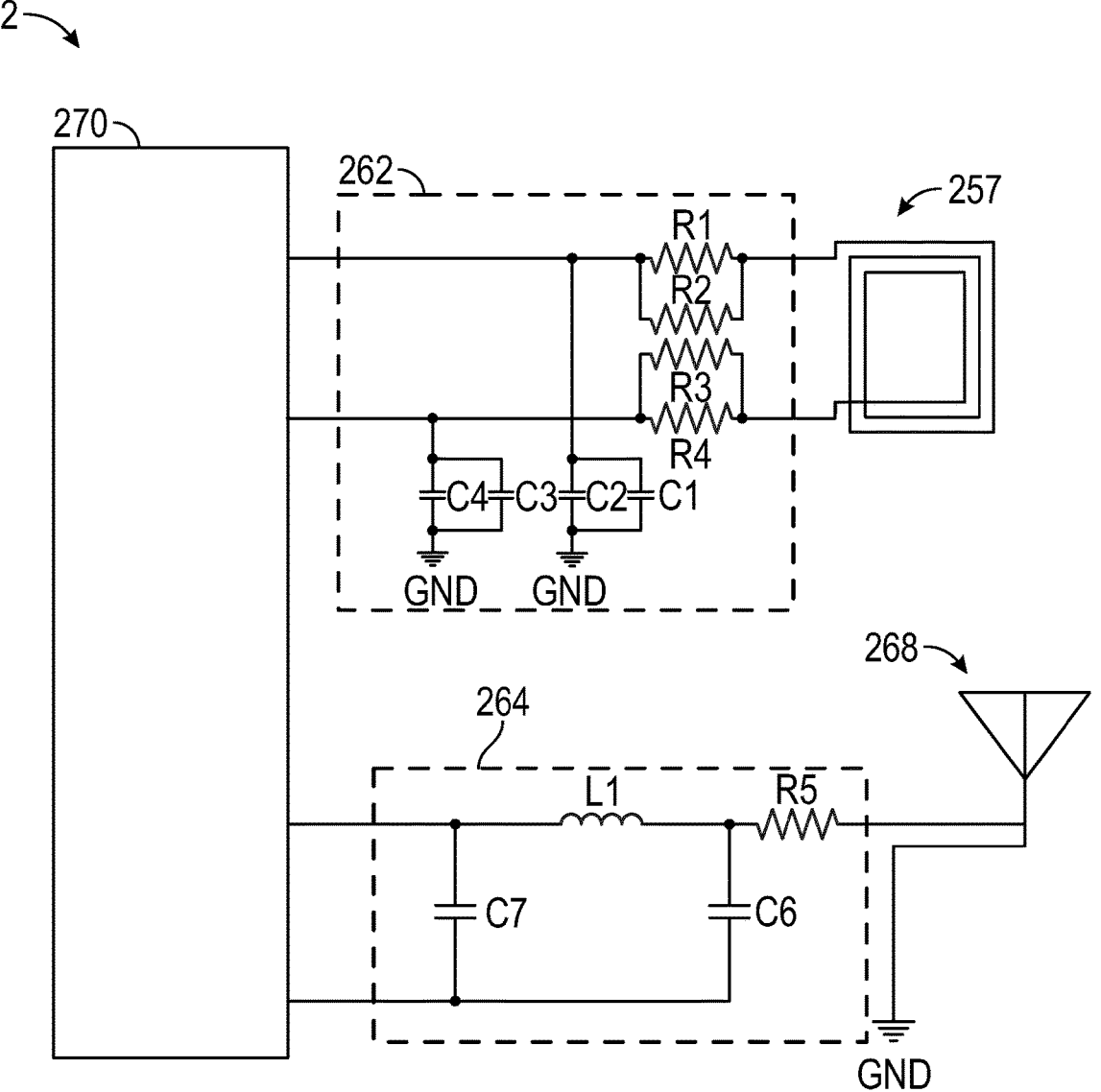
FIGS. 6A-6B illustrate schematics of electronic communications circuitry of the negative pressure wound therapy device of FIG. 2A.

FIG. 6A illustrates a schematic of an electronic communications circuitry 602 of the pump assembly 160. A communications controller (or transceiver) 270 can be connected to the antenna 257. A matching network 262 can be interposed between the communications controller 270 and the antenna 257. The matching network 262 can be configured to match the output impedance of the antenna 257 (which can vary as the RF frequency varies) to the input impedance of the communications controller 270 at the desired communication protocol frequency (such as, about 13.56 MHz). The matching network 262 can include two sets of resistor pairs connected in parallel (R1 and R2; R3 and R4) and two sets of capacitor pairs connected in parallel (C2 and C2; C3 and C4). The capacitors of the matching network 262 can be used to counter the inductance of the antenna 257.

FIG. 6A also illustrates the antenna 268, which can facilitate communication with a remote computing device via another communication protocol. The antenna 268 can be a Bluetooth (or BLE) antenna. As described herein, the antenna 268 can be supported by the PCB 222. The antenna 268 can be a PIFA antenna, which can be positioned on the PCB 222. A matching network 264 can be interposed between the communications controller 270 and the antenna 268. The matching network 264 can be configured to match the output impedance of the antenna 268 (which can vary as the RF frequency varies) to the input impedance of the communications controller 270 at the desired communication protocol frequency (such as, about 2.4 GHz). The matching network 262 can include a x-network that includes an inductor L1 and two capacitors C6 and C7. In some cases, capacitor C6 can be omitted (for example, during manufacturing), and the matching network 264 becomes an L-network. The matching network 262 can serves to create a non-reactive antenna load for the communications controller 270. In some cases, the communications controller 270 can be used to operate the antenna 257 (which can be part of the passive NFC tag) and the antenna 268. For instance, the communications controller 270 can include two transceivers (one for the antenna 257 and the other for the antenna 268) on a single chip or integrated circuit. This can be advantageous to using separate communications controller for each of the antennas 257 and 268. For example, one or more of space, circuit complexity, power consumption, or cost can be reduced. In some implementations, separate communication controllers may be used.

Figure 6B:
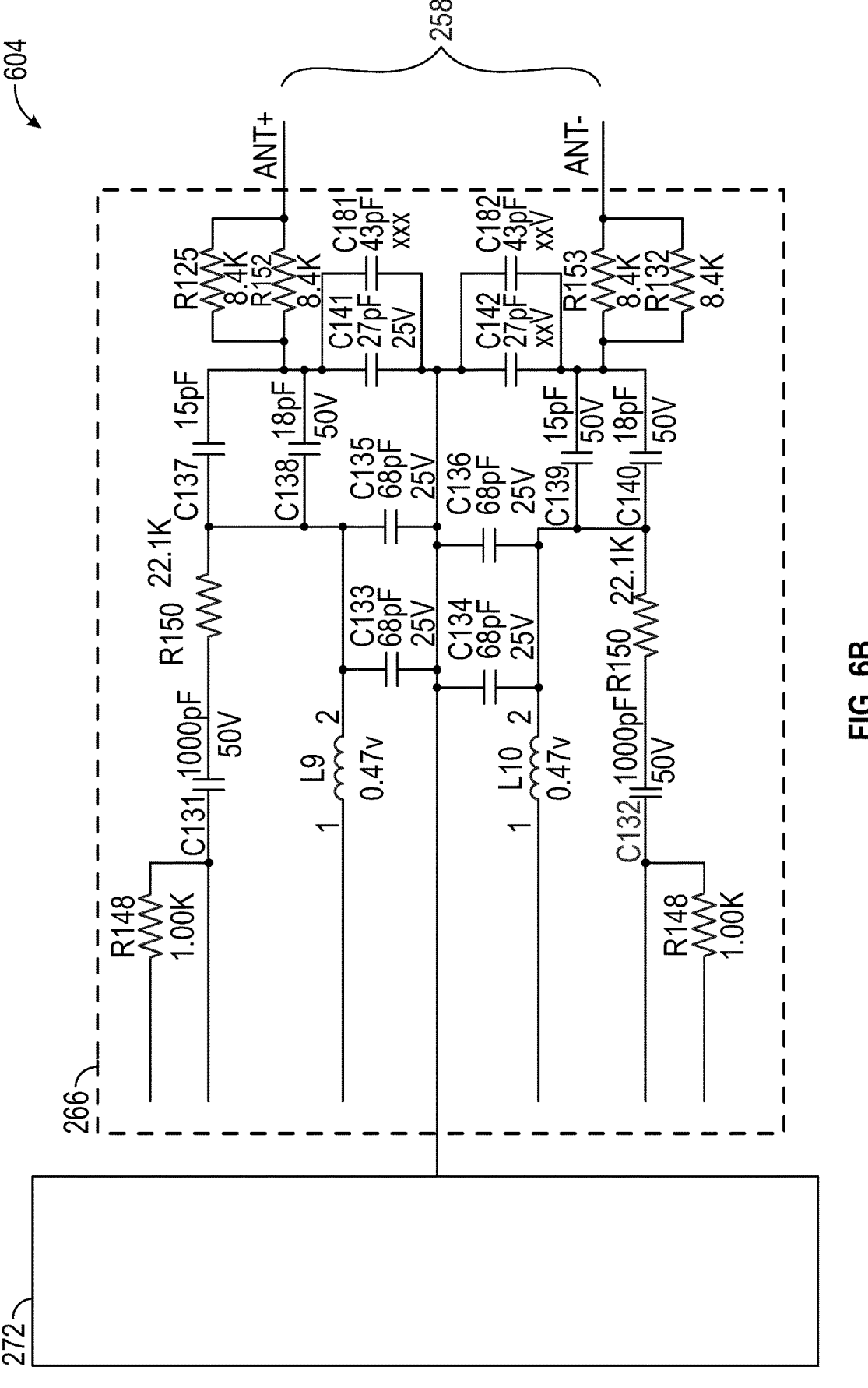

FIG. 6B illustrates a schematic of an electronic communications circuitry 604 of the pump assembly 160. A communications controller (or transceiver) 272 can be connected to the antenna 258. A matching network 266 can be interposed between the communications controller 272 and the antenna 258. The antenna 258 can be part of the active NFC tag. The matching network 266 can be configured to match the output impedance of the antenna 258 (which can vary as the RF frequency varies) to the input impedance of the communications controller 272 at the desired communication protocol frequency (such as, about 13.56 MHz). The matching network 266 may be more complex than the matching network 262 because the antenna 258 can be configured for transmitting and receiving data (to support the active NFC tag). As is illustrated in FIGS. 6A-6B, different communication controllers can be utilized for the antennas 257 and 258.

Cellular and GPS Connectivity

Any of the negative pressure wound therapy devices disclosed herein (such as, the pump assembly 160) can support one or more of cellular or GPS connectivity. Among other things, this can advantageously allow the device to send or receive data anywhere where cellular connectivity is present (irrespective of the range of the another communication protocol described herein) and allow tracking of the location of the device via GPS.

Figure 7A:
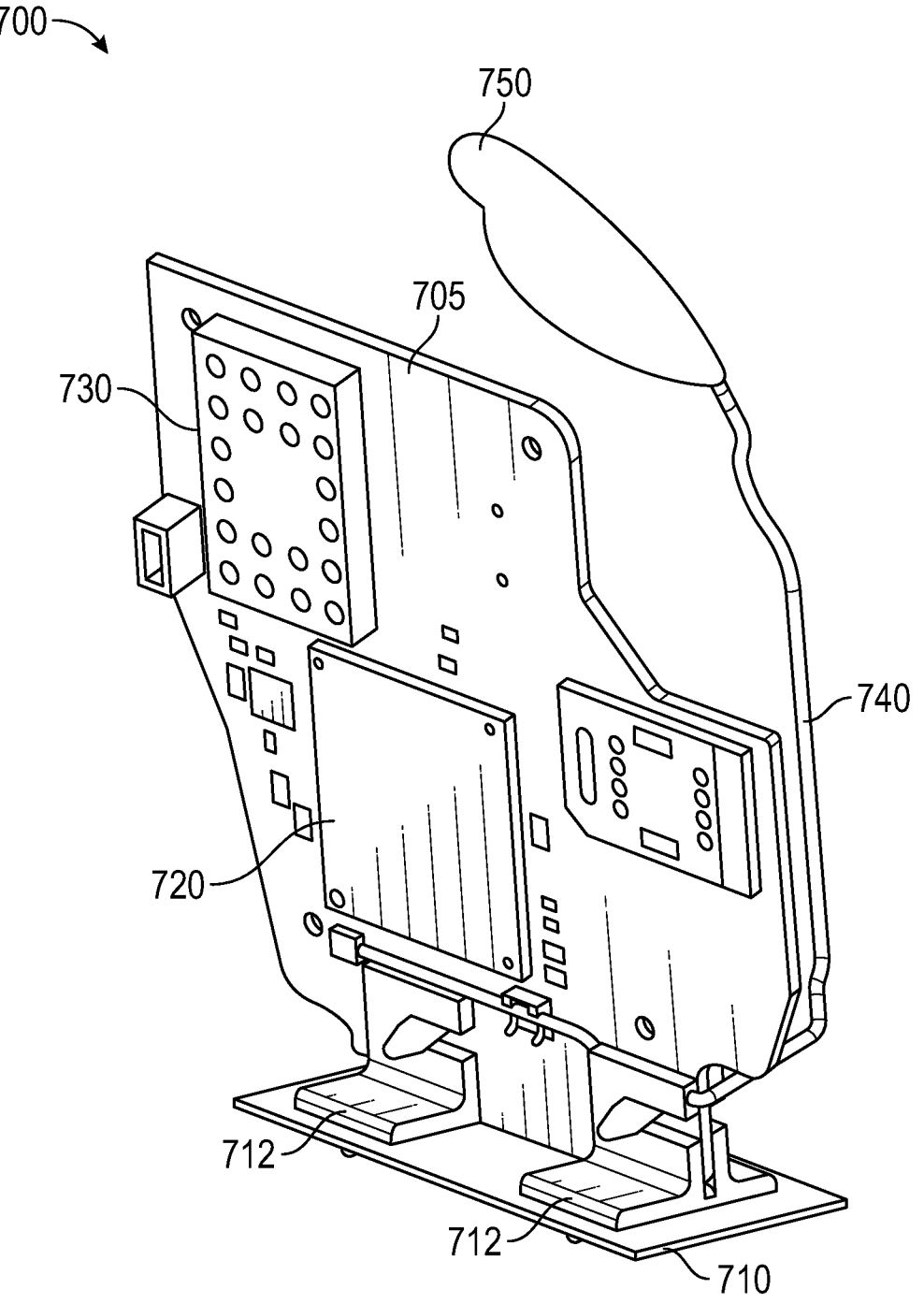
FIGS. 7A-7C illustrate a communications assembly for cellular and global positioning system (GPS) communications.

FIG. 7A illustrates a communications assembly 700 for cellular and GPS communications. The assembly 700 can be utilized by any of the negative pressure wound therapy devices disclosed herein, such as the pump assembly 160. The assembly 700 can include an antenna board 710 and a processor or communications board 705. One or more of the antenna board 710 or the communications board 705 can be a PCB. The communications board 705 can include a communications controller 720 (or transceiver). The communications board 705 can include a voltage regulator 730. One or more of the communications controller 720 or the voltage regulator 730 can be shielded.

The antenna board 710 can include wireless mobile communications antenna, such a single-, dual-, tri-, quad- or the like band antenna for communicating via 2G, 3G, LTE, 4G, 5G, or the like. The antenna can be referred to as a cellular antenna. The antenna board 710 can be mounted to the communications board 705 with mounting brackets 712. The communications assembly 700 can be electrically coupled via a path 740 to a GPS antenna 750. The antenna board 710 can be positioned in the bottom of the negative pressure wound therapy device (such as, the pump assembly 160). This positioning can advantageously shield the antenna board 710 (and the antenna) from interference (such as, electromagnetic interference) due to the presence and operation of internal electronic and electromechanical components (such as, the negative pressure source) and external noise (such as, electromagnetic interference, electrostatic discharge, or the like). Additionally or alternatively, such positioning may desirably afford additional space for increasing a size of the antenna to improve its performance (such as, improve the receive or transmit signal strength), as well as to enable the canister to function as a spacer to space the antenna from the ground or other surface on which the pump assembly is positioned. The antenna can be oriented to face downward (for example, toward the ground, floor, desk, bed, or other surface on which the pump assembly is positioned) rather than upward (for example, toward a ceiling or sky) or sideward (for example, toward side wall of a room) when the negative pressure wound therapy device is oriented for delivery of negative pressure therapy. This orientation can allow the antenna to reflect a communication signal (for example, a strongest signal or most of the energy of the signal received or output by the antenna) off the ground or another surface on which the device is positioned.

Figure 7B:
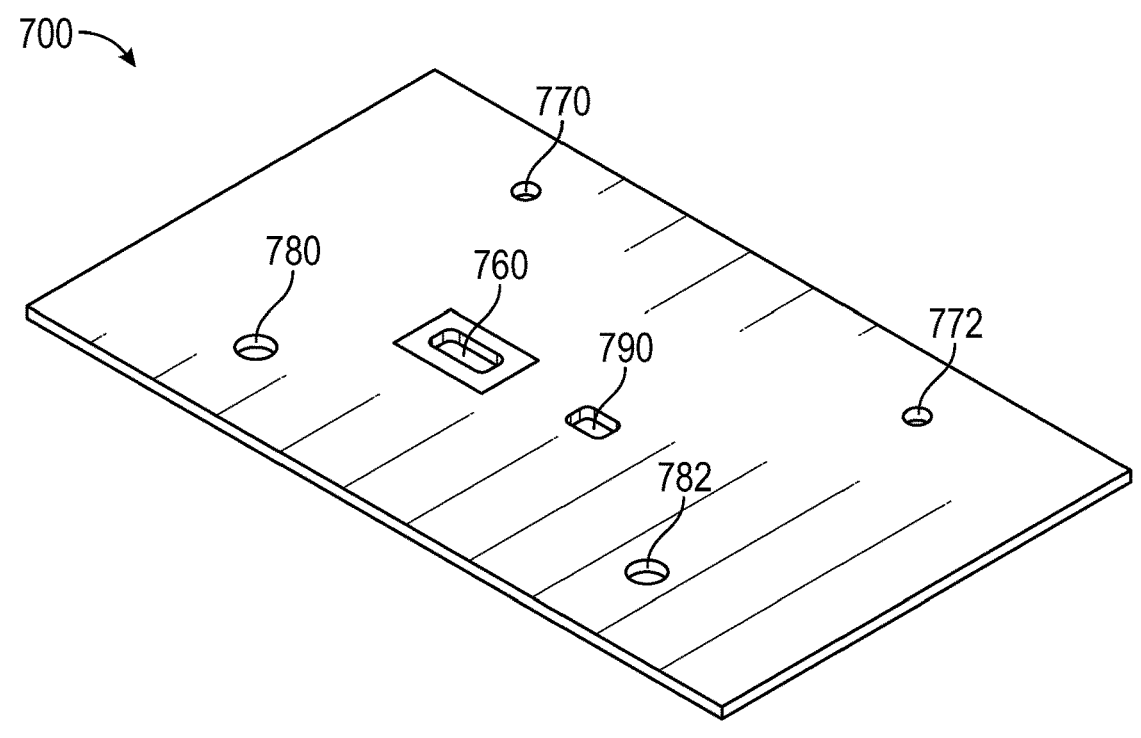
Figure 7C:
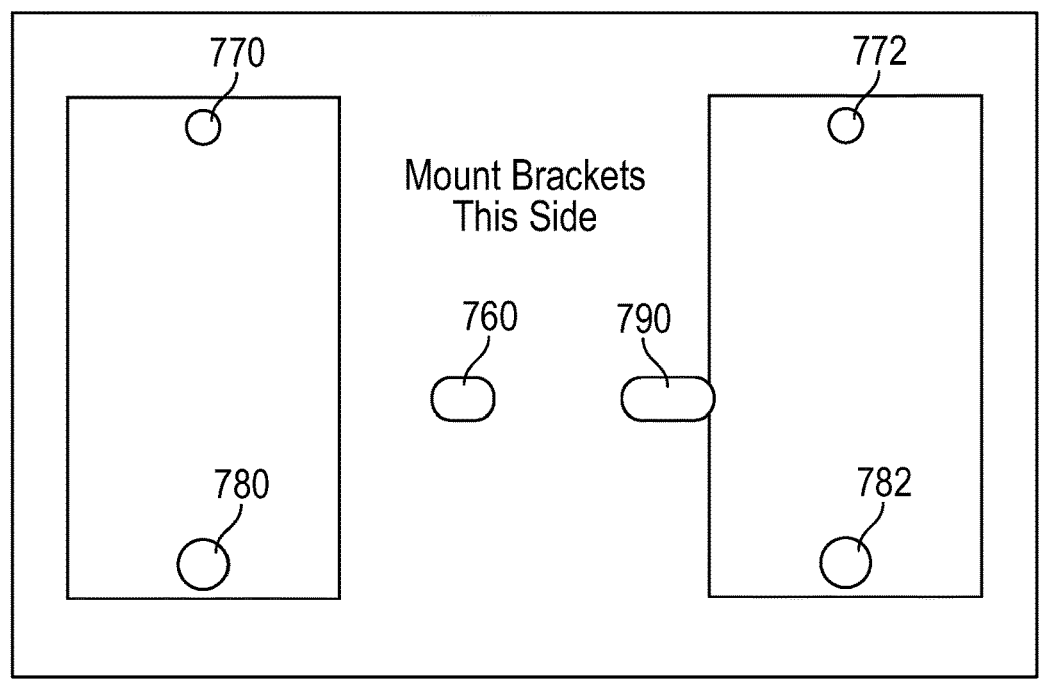

FIGS. 7B-7C illustrate the antenna board 710. FIG. 7B shows the top, perspective view of the board 710 illustrating holes 770, 772, 780, and 782 for aligning and attaching the mounting brackets and holes 760 and 790 for aligning and attaching the corresponding protrusions of the communications board 705. The hole 760 can includes a signal connector or connection between the antenna and a controller, such as the communications controller 720. FIG. 7C illustrates the bottom view of the antenna board 710. The mounting brackets 712 can be attached to the bottom side of the antenna board 710, which results in the top side of the antenna board 710 facing downward and away from the communications board 705 when the antenna board is attached or mounted to the communications board 705. In some cases, the mounting brackets 712 can be attached to the top side of the antenna board 710. The antenna can be oriented at any desired angle to the communications board 705, such as at 90 degrees, 80 degrees, 70 degrees, 60 degrees, and so on. In some implementations, desired orientation can be achieved by rotating or pivoting the mounting brackets 712.

In some implementations, the cellular antenna can be supported at least partially on an external surface of the pump assembly 160. This can overcome space restrictions inside the housing and allow the cellular antenna to be larger, allow multiple antennas to be used, or the like. Externally positioned cellular antenna can be supported by a portion of the exterior surface of the pump assembly 160 facing the canister. Advantageously, this can provide shielding from interference, as described herein. Externally positioned cellular antenna can be at least partially surrounded by an enclosure. The enclosure can include water resistant or waterproof material, such as rubber. Externally positioned cellular antenna can be connected to the communications circuit board located inside the housing (such as, the communications board 705) using a cable (for instance, a coaxial cable). In some cases, a bulkhead SMA connector can be used.

Figure 8A:
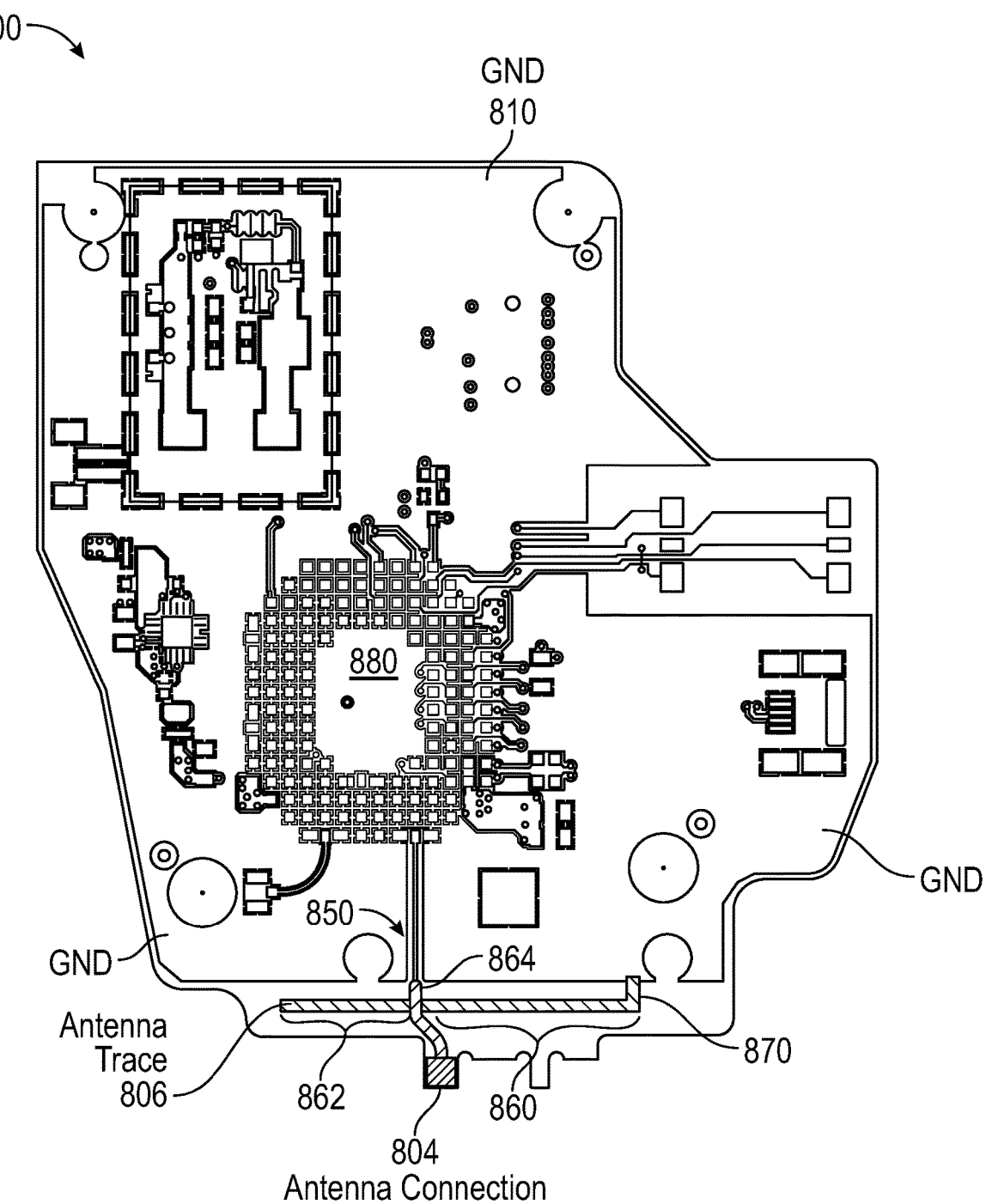
FIGS. 8A-8B illustrate a top layer and bottom layer of a communications circuit board for cellular communications.
Figure 8B:
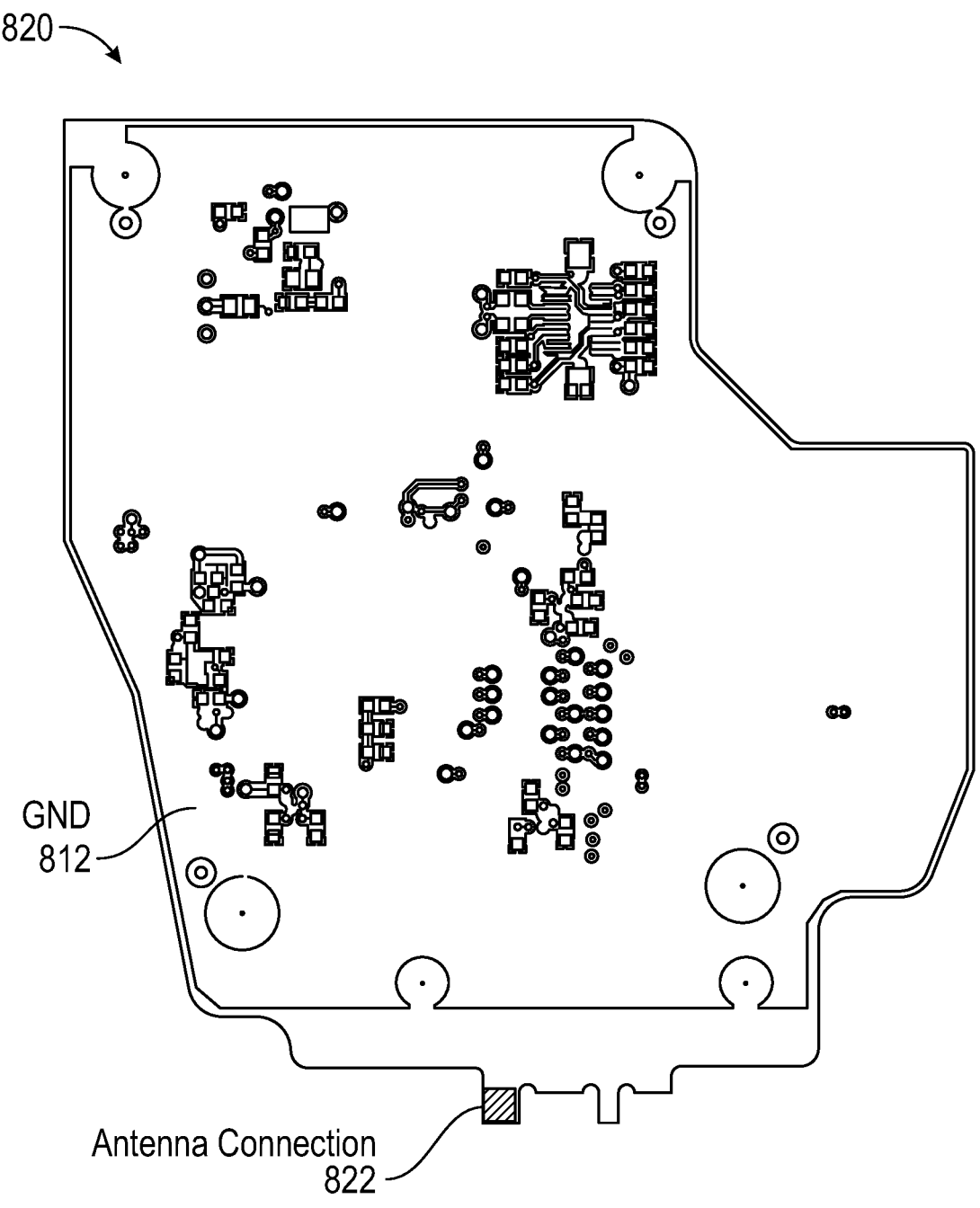

FIGS. 8A-8B illustrate a top layer or side 800 and bottom side 820 of a communications circuit board, such as the communications board 705. With reference to FIG. 8A, the top side 800 includes conductive portions (shown as darkened or shaded areas) and nonconductive portions or voids (shown as undarkened or white areas). The top side 800 can include a ground (GND) plane 810 and a connector or connection 804 between the antenna board 710 and the communications board 705. The connection 804 can provide a transmit signal feed from a controller (for example, the communication controller 720) and the antenna board 710 when antenna is transmitting (or is in a transmit mode). Connection 804 can provide a receive signal feed from the antenna board 710 to the controller when the antenna is receiving (or is in a receive mode). The connection 804 can, in some implementations, be the sole connection point for transmitting and receiving signals via the antenna board 710. Antenna trace 806, which includes first and second portions 860 and 862, is connected to the ground plane 810 at or near location 870. Location 870 can serve as shunt or ground connection of the antenna positioned on the antenna board 710. The trace 806 includes conductive material, such as copper, and can serve as a ground trace or ground plane for the antenna board 710. Connection between the trace 806 and the ground plane 810 of the communications board 705 can be accomplished with a shunt or another suitable component. Antenna trace 806 can be connected to the controller (located in area 880) via a feed path 850.

In certain implementations, the top side of the antenna board 710 (FIG. 7B) is placed facing down toward the ground and facing away from the communications board 705 when the antenna board is mounted to the communications board 705. Connection 760 can be located on the bottom side of the antenna board (FIG. 7C), which faces the communications board 705 when the antenna board is mounted to the communications board 705. In this configuration, the connection 804 on the communications board 705 faces connection 760 on the antenna board 710. A protrusion of the communications board 705 on which the connection 804 is positioned can be placed in the hole 760 of the antenna board 710. Electrical connection between the connection 804 and the hole 760 can be made, for example, using soldering or another suitable mechanism.

FIG. 8B illustrates a bottom side 820 of the communications circuit board of FIG. 8A. The bottom side 820 includes conductive portions (shown as darkened or shaded areas) and nonconductive portions or voids (shown as undarkened or white areas). The bottom side 820 can include a ground (GND) plane 812 and an antenna connector or connection 822. Connection 822 can be used as a mechanical connection for securing the antenna board 710. For instance, when the antenna board 710 is positioned top side facing downward as explained herein, because the connection 822 is positioned on the opposite side of the board with respect to the connection 804, more reliable or secure mechanical connection can be made by soldering, gluing, or using another suitable attachment a portion of the top surface of the antenna board (for example, area on the top side including and/or surrounding the hole 760) to the connection 822. In such instances, the connection 822 does not provide any electrical connectivity, but is used solely for mechanical support. As explained herein, the protrusion of the communications board 705 can be placed in the hole 760 of the antenna board 710 so that connection 822 is located proximal the top surface of the antenna board. Soldering the antenna board connection 760 on the opposite, bottom side of the antenna board 710 to the connection 804 can provide electrical connection and, optionally, additional mechanical support. In some cases, the locations of the antenna connection 822 and the connection 804 can be switched (for example, the antenna connection 822 can be placed on the top side 800) particularly when the antenna board is positioned top side facing upward away from the ground.

The antenna board 710 can be a PCB. The antenna board 710 can support the cellular antenna, which can be printed as one or more traces on the antenna board 710. For instance, the cellular antenna can be 4G/LTE or 5G antenna. In some cases, the cellular antenna can be a 4G antenna configured to transmit and receive in LTE frequency bands (such as, one or more of 1710-2155 MHz, 699-746 MHz, 824-294 MHZ, 699-960 MHz, or 1710-2200 MHz). The cellular antenna can be an inverted-F antenna, such as a planar inverted-F antenna (PIFA). Such cellular antenna can be printed on a PCB (for instance, as one or more traces). The cellular antenna can be a microstrip antenna. As a result, the cellular antenna can be compact and inexpensive to manufacture. The antenna can be a quarter-wave length antenna. In certain implementations the antenna can be a monopole antenna, patch antenna, inverted-L antenna, or another suitable type of antenna.

In some cases, the cellular antenna may be located off a PCB, such as the antenna board 710. In such case, the antenna board 710 may not be present. The cellular antenna can be made out of metal, such as stamped metal, or be a flexible antenna, such as a flex circuit PCB antenna. Such cellular antenna can be positioned on the communications board 705 (such as, be soldered to the communications board 705) or be attached (such as, adhered) to the housing. In the latter case, the electrical connection between the cellular antenna and the communications board 705 can be made by attaching the antenna feed using a connector (such as, a spring connector or coaxial connector). In some implementations, the cellular antenna can be formed in the housing using laser direct structuring (LDS). This can be advantageous to facilitate high volume, low cost manufacturing.

Figure 9:
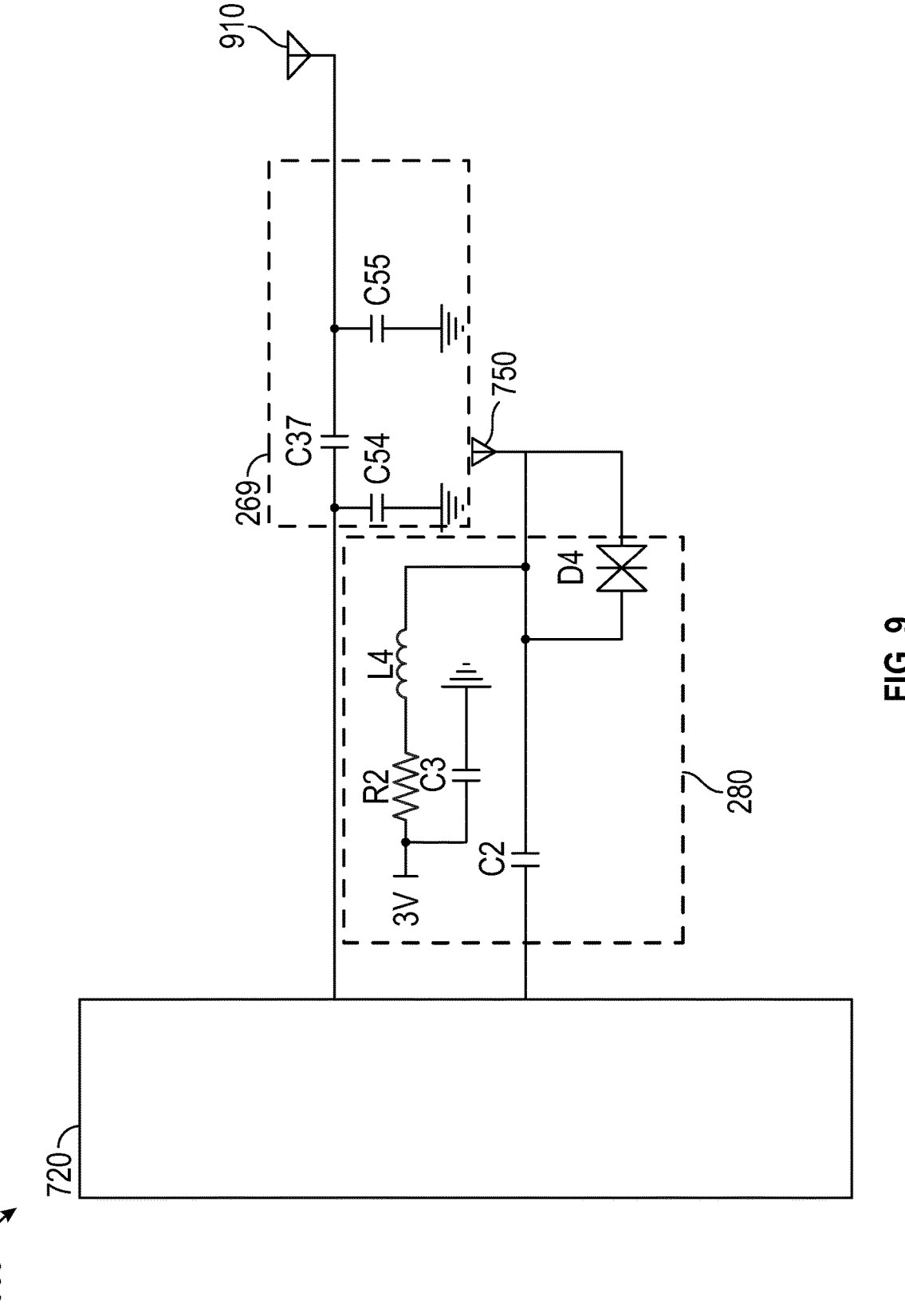
FIG. 9 illustrates a schematic of electronic communications circuitry for cellular communications.

A matching network can be interposed between the communications controller of the communications board 705 (such as, the controller 720) and the cellular antenna. The matching network can be configured to match the output impedance of the cellular antenna (which can vary as the RF frequency varies) to the input impedance of the communications controller 720. FIG. 9 illustrates a schematic of electronic communications circuitry 900 that includes a matching network 269 interposed between the controller 720 and the cellular antenna 910. The matching network 269 can include a x-network that includes capacitors C37, C55, and C54. In some cases, one or more of the capacitors C54 or C55 may be omitted (for example, during manufacturing). When one of the capacitors C54 or C55 is omitted, the matching network 269 becomes an L-network. The matching network 269, which includes capacitors, can counter the impedance of the antenna 910.

The matching network 269 can extend the operational bandwidth of the cellular antenna, which can be quite wide for a 4G/LTE or 5G antenna. For example, 4G/LTE antenna may be required to have an operational bandwidth of 699 MHz (or less) to 2200 MHz (or more). The parallel capacitance (C54 and C55) of the matching network 269 can extend the operational bandwidth of the cellular antenna in the high band (such as, 1710-2170 MHz). The series capacitance (C37) can of the matching network 269 can extend the operational bandwidth of the cellular antenna in the low band (such as, 699-960 MHz).

The GPS antenna 750 can be connected to the controller 720 as is illustrated in FIG. 9. The GPS antenna 750 can be an active antenna and include an amplifier. The amplifier can be a low noise amplifier (LNA). The amplifier can be positioned near the GPS antenna 750, such as integrated into the same package as the GPS antenna. This can help avoid losses due to the use of longer connectors, as such losses can be detrimental to the performance because the intensity of GPS signals is quite small. The circuitry 280 can be configured to provide power to the amplifier of the GPS antenna (such as, 3V as shown in FIG. 9). Because power can be provided on the same pin as the GPS data, the circuitry 280 can include an inductor L4 that decouples the power signal from the GPS data (which can be a purely alternating current (AC) signal). The capacitor C3 and resistor R2 can facilitate removal of noise from the power signal as such noise may not be blocked by the inductor and may interfere with the GPS data. Diode D4 can protect the electronics from any voltage spikes. The diode D4 can be a transient voltage suppression diode. Capacitor C2 on the GPS data line can filter out noise (such as, direct current (DC) noise).

Advantageously, the controller 720 can control both the cellular antenna 910 and the GPS antenna 750. This can be preferable to using a separate controller for each of the antennas 910 and 750. In some implementations, separate controllers may be used.

Further approaches to facilitating cellular and GPS communications are described in U.S. Patent Publication No. 2021/0030932, which is incorporated by reference in its entirety.

Figure 10A:
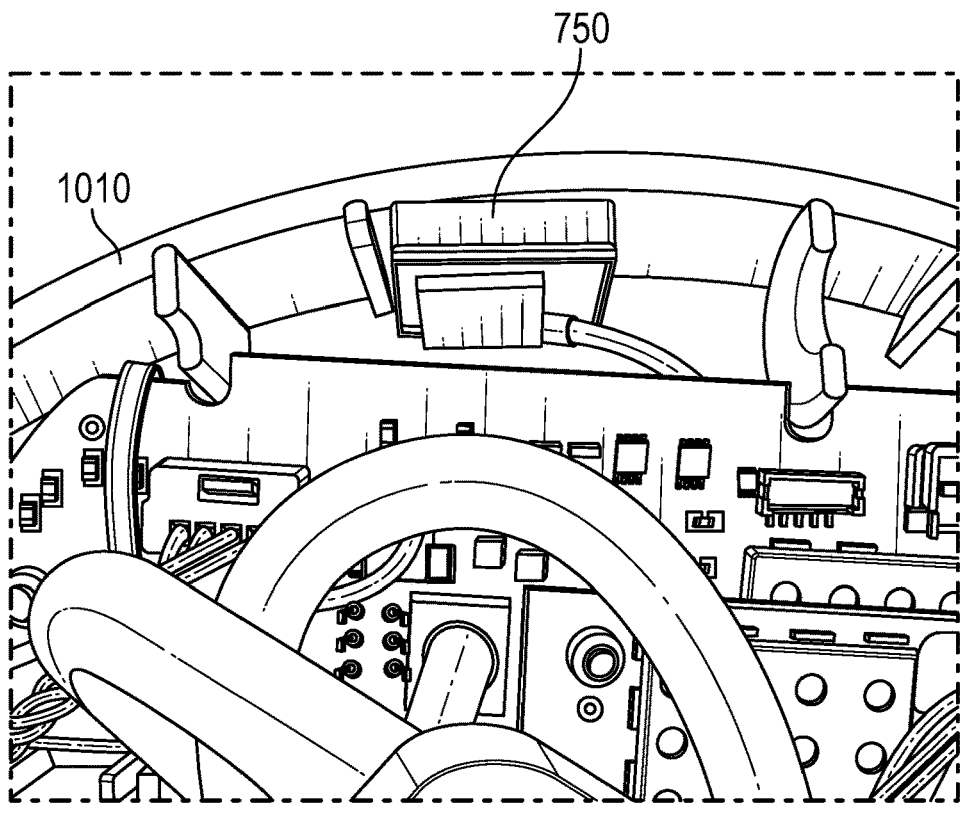
FIGS. 10A-10B illustrate integration of a GPS antenna into a negative pressure wound therapy device.
Figure 10B:
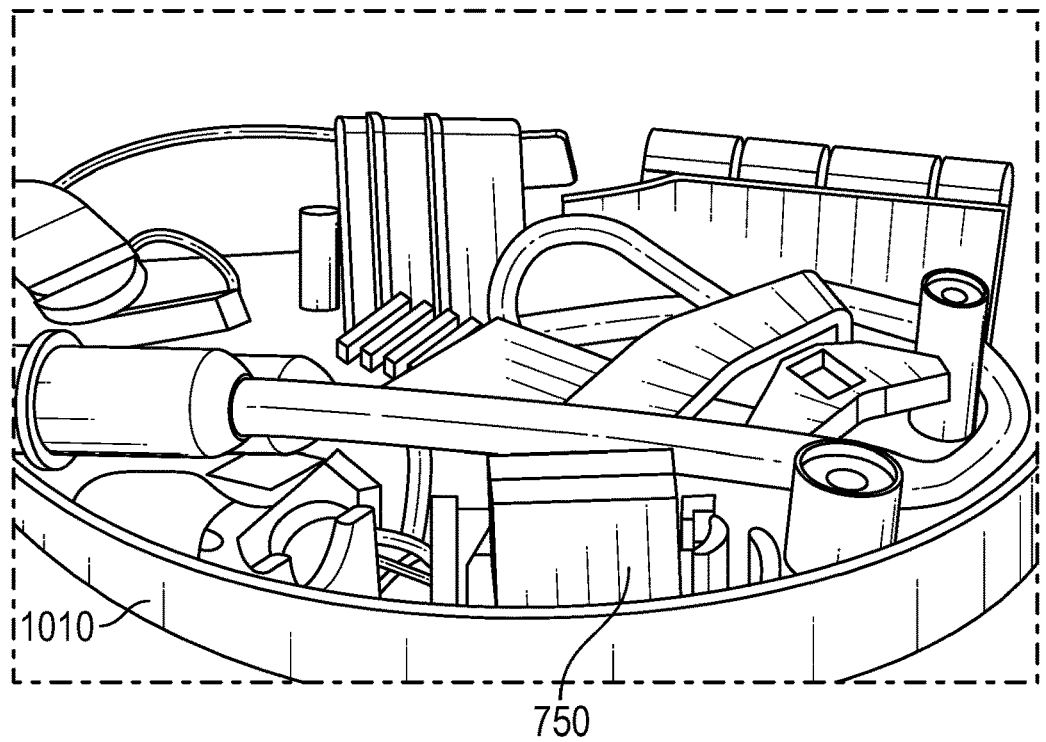

FIGS. 10A-10B illustrate integration of a GPS antenna, such as the GPS antenna 750, into a negative pressure wound therapy device, such as the pump assembly 160. The GPS antenna can be positioned off a communications board, such as the communications board 705 (or the PCB 222). To facilitate better performance, the GPS antenna 750 can be located away from the electronic and electromechanical components of the negative pressure wound therapy device (such as, the pump), which may be sources of interference for the GPS antenna 750. As is shown in FIG. 10A, the GPS antenna 750 can be positioned at or near the top of the device inside the housing 1010. As is shown in FIG. 10B, the GPS antenna 750 can be positioned at or near one of the sides of the device inside the housing 1010. The GPS antenna 750 can be attached to the housing 1010 (such as, the top portion or side portion of the housing). For example, an adhesive can be used (such as, double-sided adhesive tape).

Asset Management and Tracking

Any of the cellular antennas disclosed herein, such as the cellular antenna 910, can facilitate Internet of Things (IOT) or Machine-to-Machine (M2M) applications. In some instances, the cellular antenna can implement LTE Cat NB1, LTE Cat NB2, LTE Cat M1, LTE Cat 1, or 5G communications. Advantageously, the cellular antenna can provide support for applications requiring low power consumption (for instance, to allow operation for about 10 years (or less or more) without needing to replace or recharge the power supply). The cellular antenna can be used to provide efficient and effective asset management and tracking of negative pressure wound therapy devices and determination of the location of a patient. Additionally or alternatively, LTE can facilitate low latency (or rapid transmission), security, and privacy, provide backwards compatibility with 3G communications, provide forward compatibility with 5G communications, and facilitate making voice calls (which can allow the patient to contact the healthcare provider using the negative pressure wound therapy device).

These benefits can be realized with a cellular antenna that supports LTE (such as, LTE Cat 1, LTE Cat M1, LTE Cat NB1, or LTE Cat NB2) or 5G. Such antenna can facilitate IoT or M2M applications. Unlike GPS, which may not work well inside a structure (such as, a building), asset management and tracking as well as location determination can be accurately performed indoors and outdoors using IoT or M2M. Unlike other more complex technologies that work indoors, such as WiFi or mesh networks that may require additional hardware and consume a lot of power, using IoT or M2M can be more cost-effective and promote device longevity.

The negative pressure wound therapy device can utilize such cellular antenna to transmit information regarding the device. The information can include one or more of identification of the negative pressure wound therapy device, date and time of communication with a base station (such as, a cell tower), location (which can be determined using triangulation), power source capacity level, device maintenance data, device calibration data, negative pressure wound therapy time, device standby time, device alarm data, device temperature data, whether the device has been moved (which can be determined using a motion sensor, such as an accelerometer or a gyroscope), determination whether the device has been used, or the like. The information can be transmitted periodically (such as, once per day, several times per day, once per several days, or the like). For instance, to conserve power, the negative pressure wound therapy device can periodically wake up, transmit the information, and return to low power (or sleep) mode. This can facilitate asset management and tracking of devices that may not yet be in use to provide therapy to a patient and, as result, may not be powered on for provision of negative pressure wound therapy (such as, devices at the factory or other storage, in transit, or in storage at the healthcare facility). The negative pressure wound therapy device can include a primary power source configured to power the device for provision of therapy and a secondary power source configured to power the cellular communications circuitry. As described herein, IoT or M2M applications can consume little power so that the secondary power source may not need to be recharged or replaced for 5 years (or less or more) or 10 years (or less or more).

In some cases, when the negative pressure wound therapy device is in transit on an aircraft, it may not be desirable to initiate or maintain cellular communications. The device can be configured to detect being on the aircraft and, in response to the detection, disable cellular communications until it has been detected that the device is no longer on the aircraft. The detection of being on (or off) the aircraft can be performed using an altitude meter (or altimeter) or a vibration sensor (such as, an accelerometer or a strain gauge) that can detect aircraft vibration.

Additional details of asset management and tracking and location determination are described in U.S. Pat. Nos. 9,737, 649 and 10,744,239, each of which is incorporated by reference in its entirety.

Other Variations

Although some embodiments describe negative pressure wound therapy, the systems, devices, and/or methods disclosed herein can be applied to other types of therapies usable standalone or in addition to TNP therapy. Systems, devices, and/or methods disclosed herein can be extended to any medical device, and in particular any wound treatment device. For example, systems, devices, and/or methods disclosed herein can be used with devices that provide one or more of ultrasound therapy, oxygen therapy, neurostimulation, microwave therapy, active agents, antibiotics, antimicrobials, or the like. Such devices can in addition provide TNP therapy. The systems and methods disclosed herein are not limited to medical devices and can be utilized by any electronic device.

Any of transmission of data described herein can be performed securely. For example, one or more of encryption, https protocol, secure VPN connection, error checking, confirmation of delivery, or the like can be utilized.

Any value of a threshold, limit, duration, etc. provided herein is not intended to be absolute and, thereby, can be approximate. In addition, any threshold, limit, duration, etc. provided herein can be fixed or varied either automatically or by a user. Furthermore, as is used herein relative terminology such as exceeds, greater than, less than, etc. in relation to a reference value is intended to also encompass being equal to the reference value. For example, exceeding a reference value that is positive can encompass being equal to or greater than the reference value. In addition, as is used herein relative terminology such as exceeds, greater than, less than, etc. in relation to a reference value is intended to also encompass an inverse of the disclosed relationship, such as below, less than, greater than, etc. in relations to the reference value.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), and/or all of the steps of any method or process so disclosed, can be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated and/or disclosed may differ from those shown in the figures. Depending on the embodiment, certain of the steps described above may be removed, others may be added. For example, the actual steps and/or order of steps taken in the disclosed processes may differ from those shown in the figure. Depending on the embodiment, certain of the steps described above may be removed, others may be added. For instance, the various components illustrated in the figures or described herein may be implemented as software and/or firmware on a processor, controller, ASIC, FPGA, and/or dedicated hardware. The software or firmware can include instructions stored in a non-transitory computer-readable memory. The instructions can be executed by a processor, controller, ASIC, FPGA, or dedicated hardware. Hardware components, such as controllers, processors, ASICs, FPGAs, and the like, can include logic circuitry. Furthermore, the features and attributes of the specific embodiments disclosed above may be combined in different ways to form additional embodiments, all of which fall within the scope of the present disclosure.

User interface screens illustrated and described herein can include additional and/or alternative components. These components can include menus, lists, buttons, text boxes, labels, radio buttons, scroll bars, sliders, checkboxes, combo boxes, status bars, dialog boxes, windows, and the like. User interface screens can include additional and/or alternative information. Components can be arranged, grouped, displayed in any suitable order.

Conditional language used herein, such as, among others, "can," "could", "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied. Additionally, the words "herein," "above," "below," and words of similar import, when used in this application, refer to this application as a whole and not to any particular portions of this application.

Conjunctive language, such as the phrase "at least one of X, Y and Z," unless specifically stated otherwise, is to be understood with the context as used in general to convey that an item, term, etc. may be either X, Y, or Z, or a combination thereof. Thus, such conjunctive language is not generally intended to imply that certain embodiments require at least one of X, at least one of Y and at least one of Z to each be present.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations.

Although the present disclosure includes certain embodiments, examples and applications, it will be understood by those skilled in the art that the present disclosure extends beyond the specifically disclosed embodiments to other alternative embodiments and/or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

What is claimed is:

1. A negative pressure wound therapy device comprising:
   a housing;
   a negative pressure source supported by the housing, the negative pressure source configured to provide negative pressure to a wound covered by a wound dressing, the negative pressure source being further configured to provide negative pressure in accordance with a set of negative pressure wound therapy parameters;
   an electronic control circuitry supported by the housing, the electronic control circuitry configured to operate the negative pressure source to provide negative pressure in accordance with the set of negative pressure wound therapy parameters;
   a first antenna positioned in first portion of the housing that comprises a top portion of the housing or a side portion of the housing, the first antenna configured to facilitate wireless communications with a remote computing device, the electronic control circuitry configured to utilize the first antenna to exchange pairing data with the remote computing device using a first communication protocol to allow exchange of data between the remote computing device and the negative pressure wound therapy device using a second communication protocol;

a second antenna positioned in a second portion of the housing configured to support a canister that is configured to store exudate aspirated from the wound by the negative pressure source, the second portion of the housing different from the first portion of the housing, the second antenna configured to facilitate wireless communications with the canister using the first communication protocol when the canister is removably attached to the second portion of the housing, the electronic control circuitry configured to utilize the second antenna to receive canister data from the canister, the canister data comprising one or more of a fill status of the canister, an indication that the canister is full, identification data, configuration data, date of manufacture of the canister, or date of first use of the canister, and the electronic control circuitry further configured to use the canister data to control provision of negative pressure by the negative pressure source based on the canister data; and a third antenna configured to facilitate wireless communications with the remote computing device using the second communication protocol that is different from the first communication protocol, the electronic control circuitry configured to utilize the third antenna to transmit first data comprising at least one of a location of the housing, logs corresponding to provision of negative pressure, or alarms caused by provision of negative pressure and receive second data comprising at least one of data for tracking the location of the housing, data for adjusting the set of negative pressure wound therapy parameters, or data for upgrading software or firmware.

2. The negative pressure wound therapy device of claim 1, wherein the second communication protocol permits communication over a longer distance than the first communication protocol.

3. The negative pressure wound therapy device of claim 1, wherein the first communication protocol comprises a near-field protocol and the second communication protocol comprises Bluetooth or Bluetooth low energy (BLE) protocol.

4. The negative pressure wound therapy device of claim 1, wherein the electronic control circuitry is configured to non-simultaneously transmit or receive data using the first or second antenna.

5. The negative pressure wound therapy device of claim 1, wherein the electronic control circuitry is configured to determine that the canister is connected to the housing responsive to receiving the canister data.

6. The negative pressure wound therapy device of claim 5, wherein the electronic control circuitry is configured to disallow activation of the negative pressure source responsive to determining that the canister is not connected to the housing.

7. The negative pressure wound therapy device of claim 1, wherein the electronic control circuitry further comprises a first transceiver connected to the first and third antennas and a second transceiver connected to the second antenna.

8. The negative pressure wound therapy device of claim 7, wherein the electronic control circuitry further comprises:

a first matching circuitry interposed between the first transceiver and the first antenna, the first matching circuitry configured to match impedance of the first antenna with a first input impedance of the first transceiver;

a second matching circuitry interposed between the first transceiver and the second antenna, the second matching circuitry configured to match impedance of the second antenna with a second input impedance of the first transceiver; and a third matching circuitry interposed between the second transceiver and the third antenna, the third matching circuitry configured to match impedance of the third antenna with an input impedance of the second transceiver.

9. The negative pressure wound therapy device of claim 8, wherein the first matching circuitry comprises at least one capacitor and at least one resistor, and wherein the third matching circuitry comprises at least one capacitor, at least one inductor, and at least one resistor.

10. The negative pressure wound therapy device of claim 1, wherein the third antenna is positioned in the top portion of the housing proximate to the first antenna.

11. The negative pressure wound therapy device of claim 1, wherein the first and third antennas are positioned on a circuit board.

12. The negative pressure wound therapy device of claim 1, wherein the third antenna comprises a planar inverted-F antenna.

13. The negative pressure wound therapy device of claim 1, wherein the second portion of the housing comprises a bottom portion of the housing.

* * * * *